US010463728B2

(12) United States Patent
Schrader

(10) Patent No.: US 10,463,728 B2
(45) Date of Patent: *Nov. 5, 2019

(54) CROSS-PROTECTIVE PATHOGEN PROTECTION, METHODS AND COMPOSITIONS THEREOF

(71) Applicant: John W. Schrader, West Vancouver (CA)

(72) Inventor: John W. Schrader, West Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/616,226

(22) Filed: Jun. 7, 2017

(65) Prior Publication Data

US 2017/0327565 A1    Nov. 16, 2017

Related U.S. Application Data

(63) Continuation of application No. 13/811,467, filed as application No. PCT/CA2011/000817 on Jul. 22, 2011, now Pat. No. 9,707,288.

(60) Provisional application No. 61/366,747, filed on Jul. 22, 2010.

(51) Int. Cl.
| | |
|---|---|
| C07K 16/10 | (2006.01) |
| G01N 33/569 | (2006.01) |
| C12N 7/00 | (2006.01) |
| C07K 14/005 | (2006.01) |
| A61K 39/145 | (2006.01) |
| A61K 39/12 | (2006.01) |
| A61K 39/00 | (2006.01) |

(52) U.S. Cl.
CPC ............ *A61K 39/145* (2013.01); *A61K 39/12* (2013.01); *C07K 16/1018* (2013.01); *A61K 2039/5252* (2013.01); *A61K 2039/545* (2013.01); *A61K 2039/575* (2013.01); *C07K 2317/21* (2013.01); *C07K 2317/33* (2013.01); *C07K 2317/565* (2013.01); *C07K 2317/622* (2013.01); *C07K 2317/76* (2013.01); *C12N 2760/16134* (2013.01)

(58) Field of Classification Search
CPC .................. A61K 39/12; A61K 39/145; C12N 2760/16134; C12N 7/00; C07K 14/005
See application file for complete search history.

(56) References Cited

U.S. PATENT DOCUMENTS

| | | | |
|---|---|---|---|
| 6,720,409 B2 | 4/2004 | Okuno et al. | |
| 7,112,661 B1 | 9/2006 | Miller et al. | |
| 7,473,423 B2 | 1/2009 | Rodriguez et al. | |
| 7,601,500 B2 | 10/2009 | van de Zande | |
| 7,601,502 B2 | 10/2009 | van de Zande | |
| 2007/0224627 A1 | 9/2007 | Horowitz et al. | |
| 2009/0214428 A1 | 8/2009 | Dimitrov et al. | |
| 2009/0311265 A1 | 12/2009 | Van Den Brink et al. | |

FOREIGN PATENT DOCUMENTS

| | | |
|---|---|---|
| EP | 0366239 A1 | 5/1990 |
| WO | 2006/017538 A2 | 2/2006 |
| WO | 2006/068953 A2 | 6/2006 |
| WO | 2006/124269 A2 | 11/2006 |
| WO | 2007/052057 A2 | 5/2007 |
| WO | WO2007052057 * | 5/2007 |
| WO | 2008/152422 A2 | 12/2008 |
| WO | 2009/068992 A1 | 6/2009 |
| WO | 2010/036948 A2 | 4/2010 |
| WO | 2010/130636 A1 | 11/2010 |

OTHER PUBLICATIONS

Webster et al., Ann N Y Acad Sci., 2014, 1323(1):pdf pp. 1-38.*
Jang et al., Viruses, 2014, 6:3159-3180.*
Schwarz et al., "Single dose vaccination with AS03-adjuvanted H5N1 vaccines in a randomized trial induces strong and broad immune responsiveness to booster vaccination in adults", 2009, Vaccine, 27:6284-6290.*
Roberts, Michelle, "Swine Flu offers 'extraordinary super immunity'", BBC News Health, Jan. 10, 2011.
Schwarz, T.F. et al., "Single dose vaccination with AS03-adjuvanted H5N1 vaccines in a randomized trial induces strong and broad immune responsiveness to booster vaccination in adults", Vaccine, 2009, vol. 27, No. 45, pp. 6284-6290, ISSN: 0264-410X.
Corti, D. et al., "Heterosubtypic neutralizing antibodies are produced by individuals immunized with a seasonal influenza vaccine", Journal of Clinical Investigation, May 2010, vol. 120, No. 5, pp. 1663-1673, ISSN: 0021-9738.
Chen, Y. et al., "Broad cross-protection against H5N1 avian influenza virus infection by means of monoclonal antibodies that map to conserved viral epitopes", Journal of Infectious Diseases, Jan. 1, 2009, vol. 199, No. 1, pp. 49-58, ISSN: 0022-1899.
Wei, Chih-Jen et al., "Induction of Broadly Neutralizing H1N1 Influenza Antibodies by Vaccination", Science, Aug. 27, 2010, vol. 329, No. 5995, pp. 1060-1064. Published online Jul. 15, 2010.
Thompson, Christy A. et al., "Pandemic H1N1 influenza infection and vaccination in humans induces cross-protective antibodies that target the hemagglutinin stem", Frontiers in Immunology, May 2012, vol. 3, Article 87, pp. 1-19.
Sagawa, Hiroaki et al., "The Immunological Activity of a Deletion Mutant of Influenza Virus Haemagglutinin Lacking Globular Region", Journal of General Virology (1996), 77, 1483-1487.

(Continued)

*Primary Examiner* — Barry A Chestnut
(74) *Attorney, Agent, or Firm* — Bereskin & Parr LLP; Melanie Szweras

(57) ABSTRACT

The present disclosure provides a method of inducing a cross-protective immune response in a subject against a pathogen, such as influenza, comprising administering a first unique pathogen antigen to the subject; and administering a second unique pathogen antigen 3-52 weeks after a); wherein the second unique pathogen antigen and the first unique pathogen antigen are immunologically distinct but share conserved sites that are not normally immunogenic for antibodies. Also disclosed herein are assays for detecting cross-protective antibodies, methods of generating novel cross-protective antibodies. Further provided are novel antibodies against influenza.

10 Claims, 16 Drawing Sheets

Specification includes a Sequence Listing.

(56) References Cited

OTHER PUBLICATIONS

Steel, John et al., "Influenza Virus Vaccine Based on the Conserved Hemagglutinin Stalk Domain", mBio, Apr. 2010, vol. 1, Issue 1, pp. 1-9.
Settembre, Ethan C. et al. "Learning from the 2009 H1N1 Pandemic: Prospects for More Broadly Effective Influenza Vaccines", Journal of Molecular Cell Biology (2011), 1-3.
Wrammert, Jens et al. "Broadly Cross-Reactive Antibodies Dominate the Human B Cell Response Against 2009 Pandemic H1N1 Influenza Virus Infection", J. Exp. Med., vol. 208, No. 1, pp. 181-193.
Shwarz et al., "Single dose vaccination with AS03-adjuvanted H5H1 vaccines in a randomized trial induces strong and broad immune responsiveness to booster vaccination in adults", 2009, Vaccine, 27: 6284-6290.
Van Maurik A et al: "Seasonal influenza vaccine elicits heterosubtypic immunity against H5N1 that can be further poosted by H5N1 vaccination", Vaccine, Elsevier Ltd, GB, vol. 28, No. 7, Feb. 17, 2010 (Feb. 17, 2010), pp. 1778-1785.
Sabarth N et al: "Comparison of single, homologous prime-boost and heterologous prime-boost immunization strategies against H5N1 influenza virus in a mouse challenge model", Vaccine, Elsevier Ltd, GB, vol. 28, No. 3, Jan. 8, 2010 (Jan. 8, 2010), pp. 650-656.
Ekiert Damian C et al: "Antibody Recognition of a Highly Conserved Influenza Virus Epitope", Science, American Association for the Advancement of Science, Washington, DC; US, vol. 324, No. 5924, Apr. 1, 2009 (Apr. 1, 2009), pp. 246-251.
Leroux-Roels I et al: "Priming with AS03A-adjuvanted H5N1 influenza vaccine improves the kinetics, magnitude and durability of the immune response after a heterologous booster vaccination: An open non-randomised extension of a double-blind randomised primary study", Vaccine, Elsevier Ltd, GB, vol. 28, No. 3, Jan. 8, 2010 (Jan. 8, 2010), pp. 849-857.
Ikeno D et al: "A prime-boost vaccination of mice with heterologous H5N1 strains", Vaccine, Elsevier Ltd, GB, vol. 27, No. 23, May 18, 2009 (May 18, 2009), pp. 3121-3125.
Ekiert Damian C et al: "A Highly Conserved Neutralizing Epitope on Group 2 Influenza A Viruses", Science, American Association for the Advancement of Science, Washington, DC; US, vol. 333, No. 6044, Aug. 12, 2011 (Aug. 12, 2011), pp. 843-850.
Steel et al., "Influenza Virus Vaccine Based on the Conserved Hemagglutinin Stalk Somain", 2010, mBIO, 1(1), p. 1-9.
Webster et al., "Continuing challenges in influenza", Ann N Y Acad Sci., Sep. 2014, 1323(1), pp. 1-38.
Jang et al., "Options and Obstacles for Designing a Universal Influenza Vaccine", Viruses, 2014, 6, pp. 3159-3180.

\* cited by examiner

A

B

A

Antibody Concentration (ug/ml)

Binding of Antibodies to H5N1 HA

E Binding to H5 hemagglutinin no mAB          I4-128

F  Binding to H5 hemagglutinin expressed on A549 cells

I4-128    I8-B6    I4-G8    V4-17    V3-2G6

Antibody concentration (ug/ml)

V2                    I14

10 30 90 270        10 30 90 270

Plasma titres

A

B

Antibody concentration (ug/ml)     Plasma

Titres no Ab

Prophylaxis of H5N1 infection by mAb, V3-2G6

Prophylaxis of H5N1 infection by plasma from a vaccinated subject

Figure 10

CROSS-PROTECTIVE PATHOGEN PROTECTION, METHODS AND COMPOSITIONS THEREOF

CROSS REFERENCE TO RELATED APPLICATIONS

This application is a continuation of U.S. patent application Ser. No. 13/811,467 filed Jan. 22, 2013 (now allowed), which is a national phase entry of PCT/CA2011/000817, filed Jul. 22, 2011 (which designated the U.S.), which claims priority from U.S. Provisional Patent Application No. 61/366,747 filed Jul. 22, 2010, all of which are incorporated herein by reference in their entirety.

INCORPORATION OF SEQUENCE LISTING

A computer readable form of the Sequence Listing "14636-P37132US02_SequenceListing.txt" (32,768 bytes), submitted via EFS-WEB and created on May 19, 2017, is herein incorporated by reference.

FIELD OF THE DISCLOSURE

The disclosure relates to cross-protective and novel immunological compositions and vaccines for pathogen protection, in particular, viral protection such as influenza protection. The disclosure also relates to methods of inducing an immune response that protects against a broad spectrum of pathogenic strains and subtypes and methods of vaccination thereof.

BACKGROUND OF THE DISCLOSURE

Protruding from the membrane of the influenza A viruses are two proteins, the hemagglutinin (HA) and the neuraminidase (N). The hemagglutinins are subject to extreme variation through mutation and selection by the antibodies of the host animal. The hemagglutinins of influenza A viruses circulating in different animals fall into one of 16 evolutionarily related families called subtypes (called H1, H2 . . . H16). The hemagglutinins are further divided according to phylogeny between two related groups, Group 1 (H1, H2, H5, H6, H8, H9, H11, H12, H13 and H16) and Group 2 (H3, H4, H7, H10, H14 and H15). The neuraminidase likewise falls into 9 families. Influenza A viruses are classified by the subtype of hemagglutinin (HA) and the neuraminidase (N) they exhibit. The influenza A viruses currently circulating in humans (H1N1 and H3N2) are respectively of the H1 and H3 subtypes of hemagglutinin and N1 and N2 subtypes of neuraminidase. The protective immune response to seasonal influenza viruses is dominated by isolate-specific, subtype-specific, neutralizing antibodies that bind strongly to the head of the HA, thereby blocking the function of the HA proteins in attaching the virus to the host-cell receptors (Wiley et al. 1987). "Antigenic drift", the selection of strains of viruses with mutations on the surface of the HA head that decrease binding of neutralizing antibodies so that they do not protect against the new mutated ("drifted") strain of virus, creates the regular need for updated seasonal influenza vaccines. The HA head of the novel 2009 (H1N1) pandemic influenza A virus of swine origin (nH1N1) was antigenically distinct ("antigenic shift") from H1N1 seasonal influenza viruses that had been circulating in humans (Xu et al. 2010) and thus most humans lacked protective antibodies (Itoh et al. 2009).

The hemagglutinin protein mediates infectivity of the influenza virus, first binding the virion to the host cells, and second, fusing the membrane of the virus to the host cell membrane, enabling the viral genome to enter the cells (Wiley et al. 1987). The hemagglutinin protein has a globular head and a stem: the head of the hemagglutinin mediates the attachment of the virus to the host cells, whereas the stem of the hemagglutinin mediates the fusion of the membrane of the virus to the host cell membrane. Antibodies against the head of the hemagglutinin that only bind to the hemagglutinin of one strain or isolate of influenza virus (isolate/strain-specific) predominate in the usual human immune response to the seasonal influenza. If antibodies against the head of the hemagglutinin are of sufficient affinity/avidity and they sterically inhibit the receptor-binding site, they block infectivity of that strain/isolate of a sub-type of virus by inhibiting binding of the virus to the host cell.

Antibodies to the head of the hemagglutinin give protection from being infected twice by the same strain of influenza virus but these protective antibodies are very specific for a given isolate/strain of a subtype of influenza virus and thus only neutralize and protect against specific isolate/strains of influenza viruses (Wiley et al. 1987). As the replication of the influenza virus genome is very prone to errors, mutants of the virus readily arise. Those mutants that escape neutralization by antibodies against the head of the hemagglutinin of the original strain of virus tend to be selected to replicate because the new, mutant hemagglutinin has so low affinity for the protective antibodies against the original isolate/strain, that the antibodies can no longer neutralize the mutant virus. The mutant virus can then re-infect people immune to the original influenza virus giving rise to a new isolate of seasonal influenza. This process is called "antigenic drift" and explains why a new seasonal influenza vaccine, made up of the most dominant mutant strains of the circulating strains of influenza virus to induce neutralizing antibodies to the new mutant virus, is needed recurrently. Many mutations in the head of the hemagglutinin around the receptor-binding site that disrupt binding of neutralizing antibodies to the original isolate/strain of the virus are well-tolerated by the virus because they do not interfere with receptor binding.

There is another, more drastic change in the antigenicity of the hemagglutinin termed "antigenic shift", that is characteristic of the viruses that cause influenza pandemics. The Spanish H1N1 influenza 1918 pandemic is estimated to have killed 50 million humans. Many subtypes of influenza virus circulate in animals, mainly aquatic birds, and infection of humans with these animal viruses can cause serious human infections, with highly pathogenic avian H5N1 influenza having a mortality of over 50% (Yen and Webster, 2009). Antigenic shift can occur when different strains of influenza, circulating in birds, swine and humans, infect the same host, enabling reassortment of genetic material, which is present on 8 pieces of RNA. Alternatively it can occur when viruses that are circulating in another species other than humans, infect humans and replicate in humans and transmit between humans. In the case of the 1918 "Spanish" H1N1 influenza pandemic, the influenza virus may have obtained all its 8 gene segments from avian species (Yen and Webster, 2009). In the case of the 1957 H2N2 influenza pandemic and the 1963 H3N2 influenza pandemic, reassortment between human influenza strains and H2 or H3 from avian species was involved (Yen and Webster, 2009). The 2009 pandemic influenza A H1N1 virus (pdmH1N1) was generated by reassortment between two swine influenza viruses, each with genes from avian, swine and human influenza viruses (Ding et al, 2009, Garten et al, 2009). Thus the HA of the 1918 H1N1, 1957 H2N2, 1968 H3N2 and 2009 pandemic influenza viruses ultimately originated from avian influenza. The HA of pdmH1N1 is distantly related to the 1918 pandemic influenza H1N1 virus (Xu et al, 2010). The 2009 pandemic influenza A H1N1 virus (pdmH1N1) was generated by reassortment between two swine influenza viruses, each with genes from avian, swine and human influenza viruses (Ding et al, 2009, Garten et al, 2009). The next pandemic may have genetic contributions from the highly pathogenic H5N1 avian influenza (H5N1) (Yen and Webster, 2009). Moreover, if the highly pathogenic H5N1 avian influenza (H5N1) undergoes genetic changes that make it readily transmissible in humans, it may become a pandemic.

The differences between the amino acid sequences of the ectodomain of the hemagglutinin of pandemic influenza viruses and the current circulating seasonal influenza viruses are substantial ("antigenic shift"). For example in the hemagglutinin of the 2009 pandemic H1N1 influenza, 21% of the amino-acid sequence of the ectodomain was non-identical with the corresponding sequence in seasonal H1N1 virus and ~50% in the key epitopes on the HA head were non-identical (Xu et al, 2010). In addition, mutations in the hemagglutinin of human seasonal H1N1 influenza viruses (but not the HA of the 2009 pandemic H1N1 influenza virus that was derived from a swine H1N1 influenza virus) had introduced glycosylation sites in the head, blocking the access of neutralizing antibodies to the hemagglutinin head (Wei et al 2010a). The 2009 H1N1 virus spread so quickly it became a pandemic because the human population at that time, especially young people, had no circulating protective antibodies that could neutralize it (Itoh et al, 2009). Although there can be up to 20% amino acid differences in hemagglutinins within subtypes there can be 30-70% differences between the sequences of different subtypes of hemagglutinins (Karlsson Hedestam et al 2008). For example, the ectodomain of the hemagglutinin of an isolate of highly pathogenic avian influenza H5N1 exhibits ~36% non-identical amino acids in the corresponding sequence in seasonal H1N1 influenza or the pandemic 2009 H1N1 influenza virus.

In contrast to mutations in the head of the hemagglutinin, mutations in the stem region of hemagglutinin are not well-tolerated because most mutations in the stem disrupt its structurally constrained role in mediating the fusion of the viral membrane to the host cell membrane, which is essential for infectivity. Thus different isolates and even subtypes of influenza virus exhibit little variation in the regions of the hemagglutinin stem that control fusion (Sui et al, 2009). Rare antibodies that bind to the hemagglutinin stem can neutralize influenza viral infectivity by inhibiting the conformational change in the stalk and thus the fusion of the viral membrane and the host cells membrane (Throsby et al, 2008, Sui et al, 2009, Ekiert et al, 2009). Because the stalk is conserved over many subtypes of influenza virus, the "heterosubtypic" antibodies that target the conserved sites of the hemagglutinin stem can neutralize multiple isolates and subtypes of influenza virus (Throsby et al, 2008, Sui et al, 2009, Ekiert et al, 2009).

However, for reasons that are not understood by those skilled in the art, antibodies against the hemagglutinin stem that can bind to the hemagglutinin stem of many isolates/strains and subtypes of influenza viruses ("cross-protective or "heterosubtypic" antibodies) are not induced at high frequency in normal infections or vaccinations with seasonal influenza. Corti et al. 2010) reported that heterosubtypic memory B cells were undetectable in normal humans but after seasonal influenza vaccination they could be detected in some individuals, although the frequency after seasonal influenza vaccination was very low and variable. They generated monoclonal antibodies from these rare heterosubtypic memory B cells and all but one bound to the hemagglutinin stem. However, the frequency of the heterosubtypic memory B cells after seasonal influenza vaccination was 26-200 fold less than that of memory B cells making antibodies specific for the seasonal influenza vaccine. The question of whether these heterosubtypic memory B cells actually gave rise to plasmablasts that secreted antibodies in response to seasonal influenza vaccine was not addressed in Corti et al (2010). Corti et al. (2010) did report that they detected, using a very sensitive assay, a small amount of heterosubtypic antibody in the serum that was insufficient to neutralize the H5N1 influenza virus. Corti et al. (2010) acknowledged that the magnitude of the response they saw was not useful for protection and finished their paper with "even in high responder individuals, heterosubtypic antibodies hardly reach effective neutralizing concentration in the serum." Wrammert et al (2011) reported that they had generated monoclonal antibodies from newly generated blood plasmablasts shortly after seasonal influenza vaccination and found that none of the monoclonal antibodies were heterosubtypic antibodies targeted to the hemagglutinin stem.

The extremely low levels of cross-protective antibodies that bind with high affinity to the hemagglutinin of different isolates/strains and subtypes of virus ("cross-reactive or "heterosubtypic" antibodies) induced by infection (Wiley at al 1987) or vaccination (Corti et al, 2010) with seasonal influenza, explains why infection or vaccination with a given strain of seasonal influenza virus does not protect against other isolates/strains or subtypes of influenza virus. The lack of cross-protective and heterosubtypic antibodies is surprising given that most humans have been infected or vaccinated multiple times with different isolates/subtypes, with at least two subtypes of seasonal influenza (H1N1 and H3N2) and in some older individuals, also with the H2N2 virus.

Artificially engineered antibodies have been generated against the conserved region of the HA stem and they have been shown to neutralize multiple strains and subtypes of influenza (Throsby et al. 2008, Sui et al, 2009). They were generated by shuffling a library of human immunoglobulin heavy-chain and light-chain genes expressed in bacteriophages and selecting the resultant antibody fragments that bound to the H5 hemagglutinin of avian influenza (H5N1). These antibodies bound not only to H5 hemagglutinin but also to hemagglutinins from numerous other influenza subtypes, with the notable exception of H3 and H7 hemagglutinins from Group 2. Most of these artificial antibodies used one IGHV1-69 gene, and two studies showed by X-ray crystallography that the CDR1 and CDR2 encoded by this germline gene made the key contacts by these antibodies with the stem region of the H5 hemagglutinin (Ekiert et al. 2009; Sui et al. 2009). The light chain made minimal or no contacts with the hemagglutinin. This gene IGHV1-69 is expressed by most humans and therefore these heterosubtypic antibodies using IGHV1-69 would be expected to be made by most humans in large quantities given the recurrent antigenic stimulation with infections or vaccinations with seasonal H1N1 influenza. One group looked at the donor of the immunoglobulin gene library that yielded these artificially generated cross-reactive antibodies, and found that the donor did not have any circulating cross-reactive antibodies. Moreover Sui et al. (2009) concluded that such antibodies were not found amongst a large number of anti-influenza monoclonal antibodies cloned out of donors who had been vaccinated against seasonal influenza (Wrammert et al. 2008), and that some mechanism in the human immune system prevented these cross-reactive antibodies against the stem of hemagglutinin being produced in humans. There has been considerable interest in designing vaccines based on these observations (Chen et al. 2009). Corti et al. 2010 speculated that a new vaccine with an engineered immunogen that better exposed the stem region of the HA to achieve optimal presentation to B cells might result in heterosubtypic, cross-protective antibody responses. These attempts at producing a broad spectrum influenza vaccine have involved constructing artificial versions of the stem region of the hemagglutinin (Sagawa et al. 1996 and Steel et al. 2010) and have been based on the thesis that the stem of the hemagglutinin was masked by the bulky head domain, which was thus immunodominant (Steel et al. 2010; Wang et al 2010). However, although there was some protection induced by immunization with the "headless" HA, these researchers found no evidence (Sagawa et al. 1996) or very marginal evidence (Steel et al. 2010) that the protection was due to heterosubtypic neutralizing antibodies that could be transferred by serum from vaccinated mice. Another approach tried recently was to alter the presentation of the hemagglutinin by using DNA vaccination followed by a protein or viral vector boost (Wei et al, 2010b) which induced antibodies against the HA stem. However it was not shown by transfer of serum from vaccinated animals that the antibodies provided protection. These experiments were only done in naïve animals that had no previous experience of influenza vaccination or infection. The authors acknowledged that they might find different results, with human populations that had been previously exposed to influenza hemagglutinin.

Karlsson Hedestam et al (2008) and Kwong and Wilson (2009) drew a parallel with influenza virus and HIV-1 with respect that both viruses are extremely variable and both elicit isolate/strain-specific neutralizing antibodies against epitopes on peptide loops that both viruses can readily mutate and thus escape from the neutralizing antibodies induced by the original strain. In both diseases rare monoclonal antibodies have been generated that can neutralize a broad range of isolates and strains of viruses. Karlsson Hedestam et al (2008) and Kwong and Wilson (2009) pose the challenge to induce these broadly neutralizing antibodies by vaccination and contemplate new immunogens.

Antibodies are proteins that circulate in the bloodstream and have the ability to bind to and neutralize viruses and toxins and other pathogens. Antibodies come in billions of configurations and, given this structural diversity, it is likely that one or more of the antibodies in an individual will bind to any foreign substance or virus. The cells of the blood and immune system that make antibodies are termed "B cells". Each B cell makes only one of the billions of different types of antibodies and has samples of that antibody displayed on its surface. When foreign substances (termed "antigens"), like the influenza virus, enter the body, they bind to those rare B cells that make a specific antibody that binds that foreign substance and stimulate those B cells to multiply. The multiplying B cells then undergo a process called "affinity maturation" in a structure called a germinal centre that develops in a lymph node. In this affinity maturation process, the genes encoding antibodies in the B cells accumulate somatic mutations. In the germinal centre, those B cells that make a mutated antibody that binds tightly to the antigen are selected. To undergo this "affinity maturation" process, B cells need the help of a related cell in the immune system called the "T cell" and the process of selection of the B cells that make the highest affinity antibodies is intimately involved with the mutual interactions between B cells and T cells (Allen et al, 2007, Victora, et al 2010, Schwickert et al 2011). Those B cells that make antibodies that bind to the hemagglutinin of an influenza virus can bind to the hemagglutinin or more likely to the virion and then internalize the protein or the virus (Russell et al, 1979). The B cells digest the hemagglutinin or virus and present small parts of the proteins (peptides) to the helper T cells. B cells need to present the peptide antigen to T cells in order to form a tight conjugate that will ensure that the T cell stimulates the B cell to proliferate and enter the germinal centre (Schwickert et al 2011) and then to proliferate and survive in the germinal centre (Allen et al, 2007, Victora, et al 2010).

The mechanism of this "affinity maturation" process involves two steps, first the induction of mutations in the antibody genes in B cells, and second, the survival of those B cells that make a more tightly binding ("higher-affinity") antibody. The advantage that B cells that make the relatively higher affinity antibodies have over B cells that make lesser affinity antibodies results from them being better able to present peptide antigens to T helper cells. There is a limiting number of T cells that have receptors specific for the hemagglutinin or the proteins in the influenza virion and they form conjugates preferably with the B cells that make relatively higher affinity antibodies. These antigen-specific T cells become activated and stay in contact with the B cells while they induce them to proliferate and enter the germinal centres. When the B cells have entered the germinal centre, they need to present peptide antigens to the helper T cells to proliferate and survive. It has been recently established by elegant experiments that the relative affinity/avidity of the antibody expressed by a B cell determines its relative ability to compete with other B cells for presenting antigen to T helper cells (Victora et al 2010, Schwickert et al 2011). Thus B cells with higher affinity for the antigen will monopolize the T cell help.

The B cells that make the highest affinity antibodies and that thus survive the process of affinity maturation, become two types of specialized cells that leave the germinal centre and enter the blood, one specialized to secrete large amounts of antibodies ("antibody-secreting cells" or "plasma cells"), and one specialized to circulate in the blood for very long durations termed a "memory B cell". If the memory B cell re-encounters the same foreign substance or antigen that induced it, it responds by rapidly producing antibodies specific to the antigen, making the individual "immune" to that antigen.

Memory B cells can live for decades in the body. Indeed circulating antibodies persisted in elderly humans for over 90 years after the 1918 pandemic. Similarly, neutralizing high-affinity monoclonal antibodies have been cloned from memory B cells binding to the head of the hemagglutinin of the 1918 pandemic H1N1 influenza virus from elderly humans, from people who were born before the pandemic meaning that the memory B cells had persisted for over 90 years (Yu et al, 2008). This exemplifies the longstanding, selective pressure that human influenza viruses are under by high-affinity, neutralizing antibodies against the hemagglutinin head. Moreover it indicates that memory B cells against the hemagglutinin head are a constant feature of the human immune system and their presence and specificity and affinity must be taken into account if it is contemplated to undertake influenza vaccination. If memory B cells re-encounter their specific antigen they can respond quickly in two ways. If they bind tightly to the antigen (ie the antibody the memory B cell makes is of high-affinity), they transform into a plasmablast, a cell specialized for secreting large amounts of their specific antibody (Paus et al 2006). If they bind more weakly to an antigen, for example a mutated version of the original antigen like an escape mutant of hemagglutinin from an "antigen-drifted" influenza virus, they re-enter the affinity-maturation process and undergo selection to bind more tightly to the new antigen (Paus et al 2006). Memory B cells that make antibodies that bind relatively weakly to the hemagglutinin of an influenza virus can still bind to the hemagglutinin or to the virion and ingest the protein or the viral proteins (Schwickert et al, 2011). Thus memory B cells that make antibodies that neutralize an original isolate of seasonal influenza but that do not neutralize a "drifted" isolate of seasonal influenza, can still readily bind hemagglutinin and present peptides from the hemagglutinin or an influenza virion to helper T cells. There are many shared T cell epitopes between different isolates and subtypes of influenza viruses (Doherty et al, 2008). Moreover T cell epitopes can come from all parts of the primary sequence of the protein, even the internal parts of the protein that are not displayed on the surface. Moreover if a B cell is making an antibody that binds to hemagglutinin, that B cell can bind and internalize a virion or a fragment of it. That B cell can then present to a T cell and get help from many T cells specific for individual peptides from the internal, conserved proteins of the virion (Russell et al, 1979).

SUMMARY OF THE DISCLOSURE

The present inventor has provided evidence that serial immunization of humans previously exposed to influenza infections or vaccinations with compositions comprising antigenically distinct and unique hemagglutinin molecules, encompassing the whole or part of the ectodomain, provides for the dominance of a minor subset of B cells that make heterosubtypic or cross-reactive antibodies that bind regions of the HA that are conserved or shared between different isolates/strains and subtypes of influenza A virus. The fact that the subject to be vaccinated has not previously encountered the unique, distinct antigenic nature of these two (or more) specified hemagglutinins is critical as it avoids the activation of dominant memory B cells induced by previous seasonal influenza vaccinations or infections. The fact that there is a very low frequency of memory B cells to the unique hemagglutinin in the population to be vaccinated (for example, undetectable or less than 1 per million, or at least less than 0.01% of IgG-expressing memory B cells circulating in the blood making antibodies reacting strongly to the unique antigen) can be readily ascertained using the methods of Wen et al 1987 or Corti et al 2010. The disclosure thus provides a means to avoid activation of the memory B cells which, in a normal vaccination or infection with seasonal influenza would successfully outcompete for T cell help that minor subset of B cells that make cross-reactive, cross-protective antibodies that bind to conserved regions of the HA. Because T cells recognise T-cell epitopes shared between viral subtypes (Doherty et al 2008), the use of unique hemagglutinins or inactivated viruses or attenuated influenza viruses ensures that there is ample T cell help for the B cells making heterosubtypic, cross-protective antibodies, in contrast with using designed immunogens comprising the hemagglutinin stem (Sagawa et al. 1996, Steel et al. 2010).

Accordingly, the present disclosure provides a method of inducing a cross-protective antibody response in a subject against a pathogen comprising:
(a) administering a first unique pathogen antigen to the subject;
(b) administering a second unique pathogen antigen 3-52 weeks after a);
wherein the second unique pathogen antigen and the first unique pathogen antigen are immunologically distinct but share conserved sites that are not normally immunogenic for antibodies.

In another embodiment, the disclosure provides a use of a second unique pathogen antigen for inducing a cross-protective antibody response in a subject that has been previously subjected to a first unique pathogen antigen 3-52 weeks prior, wherein the second unique pathogen antigen and the first unique pathogen antigen are immunologically distinct but share conserved sites that are not normally immunogenic for antibodies.

Also provided herein is a second unique pathogen antigen for use in inducing a cross-protective antibody response in a subject that has been previously subjected to a first unique pathogen antigen 3-52 weeks prior, wherein the second unique pathogen antigen and the first unique pathogen antigen are immunologically distinct but share conserved sites that are not normally immunogenic for antibodies.

Further provided herein is a use of a second unique pathogen antigen for preparing a boost vaccine for vaccinating a subject that has been vaccinated with a priming vaccine comprising a first unique pathogen antigen 3-52 weeks prior, wherein the second unique pathogen antigen and the first unique pathogen antigen are immunologically distinct but share conserved sites that are not normally immunogenic for antibodies.

In one embodiment, the pathogen antigen is a hemagglutinin (HA) protein of influenza, a gB protein of human cytomegalovirus (HCMV), or a gp140 or gp160 protein of human immunodeficiency virus (HIV) or a fragment thereof.

In another embodiment, the method further comprises c) administering a third unique pathogen antigen 3-52 weeks after b), wherein the third unique pathogen antigen and the first and second unique pathogen antigens are immunologically distinct but share conserved sites that are not normally immunogenic for antibodies.

In one embodiment, one or more additional unique pathogen antigens are used as a mixture or concurrently with the first and/or second unique pathogen antigen.

Also provided herein is a method of inducing a cross-protective antibody response in a subject against influenza comprising:
(a) administering a first unique hemagglutinin (HA) protein to the subject; and
(b) administering a second unique HA protein 3-52 weeks after a), wherein the second unique HA protein and the first unique HA protein are immunologically distinct but share conserved sites that are not normally immunogenic for antibodies.

In another embodiment, the disclosure provides a use of a second unique HA protein for inducing a cross-protective antibody response in a subject that has been previously subjected to a first unique HA protein 3-52 weeks prior, wherein the second unique HA protein and the first unique HA protein are immunologically distinct but share conserved sites that are not normally immunogenic for antibodies. The disclosure also provides a second unique HA protein for use in inducing a cross-protective antibody response in a subject that has been previously subjected to a first unique HA protein 3-52 weeks prior, wherein the second unique HA protein and the first unique HA protein are immunologically distinct but share conserved sites that are not normally immunogenic for antibodies. In yet another embodiment, the disclosure provides a use of a second unique HA protein for preparing a boost vaccine for vaccinating a subject that has been vaccinated with a priming vaccine comprising a first unique HA protein 3-52 weeks prior, wherein the second unique HA protein and the first unique HA protein are immunologically distinct but share conserved sites that are not normally immunogenic for antibodies.

In one embodiment, the second unique HA protein comprises a head that is substantially antigenically unrelated to the first unique HA protein but comprises conserved antigenic sites in the stem or on the head that are normally not immunogenic for antibodies.

In an embodiment, the first and/or second unique HA protein is part of an attenuated virus or inactivated virus. In another embodiment, the first or second unique HA protein is from a pandemic virus or a virus that normally infects a different species of host. In one embodiment, the virus that infects a different host is a virus that infects an avian species or a virus that infects swine. In yet another embodiment, the first and/or second unique HA protein is an artificial HA protein having mutations in the head that make it antigenically unrelated to HA that the population to be vaccinated has been exposed to or a chimeric HA protein comprising a conserved stem coupled to a unique head.

In one embodiment, the first unique HA antigen is derived from an isolate of an H5N1 influenza A virus and the second unique HA antigen is derived from another avian influenza virus with a hemagglutinin of Group 1, such as H1, H2, H5 (with the distinction that it should be an H5 of a substantially different antigenicity) H6, H8, H9, H11, H12, H13, or H16 optionally from a subtype of H2N9, H2N2, H6N1, H6N2, H8N4, and H9N2 influenza A viruses.

Also provided herein is a method of inducing a cross-protective antibody response in a subject against influenza comprising:
a) administering a first unique hemagglutinin (HA) protein that is derived from an isolate of an H5N1 influenza A virus; and
b) administering a second unique HA protein to the subject 3-52 weeks after a), wherein the second unique HA protein derives from another avian influenza virus with a hemagglutinin of Group 1, such as H1, H2, H5, H6, H8, H9, H11, H12, H13, or H16 optionally from a subtype of H2N9, H2N2, H6N1, H6N2, H8N4, and H9N2 influenza A viruses.

In yet another embodiment, the first unique HA protein is derived from a strain or an isolate of H5N1 influenza A virus and the second unique HA protein is derived from another mammalian influenza virus with a hemagglutinin of Group 1.

Also provided herein, is a method of inducing a cross-protective antibody response in a subject against influenza comprising:
(a) administering a first unique hemagglutinin (HA) protein to the subject, wherein the first unique HA protein is from a strain or an isolate of H5N1 influenza A virus; and
(b) administering a second unique HA protein to the subject 3-52 weeks after a), wherein the second unique HA protein is from another mammalian influenza virus with a hemagglutinin of Group 1. In one embodiment, the influenza virus with a hemagglutinin of Group 1 comprises a subtype of influenza A virus circulating in pigs or horses.

In a further embodiment, the first unique HA protein is derived from a strain or an isolate of the 2009 H1N1 influenza A virus and the second unique HA protein is derived from an isolate of an H5N1 influenza A virus. Further provided herein is a method of inducing a cross-protective antibody response in a subject against influenza comprising:
(a) administering a first unique hemagglutinin (HA) protein to the subject, wherein the first unique HA protein is from a strain or an isolate of the 2009 H1N1 influenza A virus; and
(b) administering a second unique HA protein to the subject 3-52 weeks after a), wherein the second unique HA protein is from an isolate of an H5N1 influenza A virus.

Also provided herein is a method of inducing a cross-protective antibody response against influenza in a subject that has been vaccinated or infected with an influenza virus that contains a first unique hemagglutinin (HA) comprising administering to the subject a second unique HA protein 3-52 weeks after the vaccination or infection, wherein the second unique HA comprises a head that is substantially antigenically unrelated to the first unique HA, but exhibits conserved antigenic sites on the stem or conserved sites on the head that are not normally immunogenic. Further provided is use of a second unique HA protein for inducing a cross-protective antibody response against influenza in a subject that has been vaccinated or infected with an influenza virus that contains a first unique hemagglutinin 3-52 weeks prior, wherein the second unique HA comprises a head that is substantially antigenically unrelated to the first unique HA, but exhibits conserved antigenic sites on the stem or conserved sites on the head that are not normally immunogenic. Even further provided is a second unique HA protein for use in inducing a cross-protective antibody response against influenza in a subject that has been vaccinated or infected with an influenza virus that contains a first unique hemagglutinin 3-52 weeks prior, wherein the second unique HA comprises a head that is substantially antigenically unrelated to the first unique HA, but exhibits conserved antigenic sites on the stem or conserved sites on the head that are not normally immunogenic. Also provided is use of a second unique HA protein in the manufacture of a medicament for inducing a cross-protective antibody response against influenza in a subject that has been vaccinated or infected with an influenza virus that contains a first unique hemagglutinin 3-52 weeks prior, wherein the second unique HA comprises a head that is substantially antigenically unrelated to the first unique HA, but exhibits conserved antigenic sites on the stem or conserved sites on the head that are not normally immunogenic.

In one embodiment, the first unique HA protein is derived from the 2009 H1N1 influenza A virus and the second unique HA protein is derived from an isolate of an H5N1 influenza A virus. Also provided herein is a method of inducing a cross-protective immune response in a subject against influenza that has been vaccinated or infected with the 2009 H1N1 influenza A virus by administering to the subject, 3-52 weeks after the vaccination or infection a hemagglutinin (HA) that derives from an isolate of an H5N1 influenza A virus.

In another embodiment, the first unique hemagglutinin protein is a Group 1 HA protein and the second unique hemagglutinin is a Group 2 HA protein or the first unique hemagglutinin protein is a Group 2 HA protein and the second unique hemagglutinin is a Group 1 HA protein.

In one embodiment, one or more additional unique HA proteins are used as a mixture or concurrently with the first and/or second unique HA protein.

In yet a further embodiment, the unique first and/or second hemagglutinin is coupled, such as by fusion, chemically or physically, to a T-cell peptide epitope that the subject has been previously immunized against. Such T-cell peptide epitopes are well-known to those skilled in the art, for example, the epitope from tetanus toxoid.

Also provided herein is a kit comprising a first unique hemagglutinin (HA) protein as disclosed herein and a second unique hemagglutinin (HA) protein as disclosed herein, wherein the first unique HA protein and the second unique HA protein are immunologically distinct but share conserved sites that are not normally immunogenic for antibodies.

In another embodiment, the present disclosure provides a method of inducing a cross-protective antibody response in a subject against a human cytomegalovirus (HCMV) comprising:
(a) administering a gB glycoprotein or a fragment thereof comprising the gB ectodomain to the subject; and
(b) administering a modified gB glycoprotein 3-52 weeks after a);
wherein the modified gB glycoprotein lacks the AD-1 epitope.

In another embodiment, the disclosure provides a use of a modified gB glycoprotein for inducing a cross-protective antibody response in a subject that has been previously subjected to immunization with a gB glycoprotein or its ectodomain 3-52 weeks prior, wherein the modified gB glycoprotein lacks the AD-1 epitope.

The disclosure also provides a modified gB glycoprotein for use in inducing a cross-protective antibody response in a subject that has been previously subjected to a first immunization with gB glycoprotein or its ectodomain 3-52 weeks prior, wherein the modified gB glycoprotein lacks the AD-1 epitope.

In yet another embodiment, the disclosure provides a use of a modified gB glycoprotein for preparing a boost vaccine for vaccinating a subject that has been vaccinated with a priming vaccine comprising a gB glycoprotein or its ectodomain 3-52 weeks prior, wherein the modified gB glycoprotein lacks the AD-1 epitope.

In yet another embodiment the present disclosure provides a method of inducing a cross-protective neutralizing antibody response in a subject against HIV-1 comprising:
(a) administering a first unique gp140 or gp160 glycoprotein to the subject; and
(b) administering a second unique gp140 or gp160 protein, 3-52 weeks after a);
wherein the second unique gp140 or gp160 glycoprotein and the first unique gp140 or gp160 glycoprotein are immunologically distinct but share conserved sites that are not normally immunogenic for antibodies.

In another embodiment, the disclosure provides a use of a second unique gp140 or gp160 glycoprotein for inducing a cross-protective antibody response in a subject that has been previously subjected to immunization with a first unique gp140 or gp160 glycoprotein 3-52 weeks prior; wherein the second unique gp140 or gp160 glycoprotein and the first unique gp140 or gp160 glycoprotein are immunologically distinct but share conserved sites that are not normally immunogenic for antibodies.

The disclosure also provides second unique gp140 or gp160 glycoprotein for use in inducing a cross-protective antibody response in a subject that has been previously subjected to immunization with a first unique gp140 or gp160 glycoprotein 3-52 weeks prior; wherein the second unique gp140 or gp160 glycoprotein and the first unique gp140 or gp160 glycoprotein are immunologically distinct but share conserved sites that are not normally immunogenic for antibodies.

In yet another embodiment, the disclosure provides a use of a second unique gp140 or gp160 glycoprotein for preparing a boost vaccine for vaccinating a subject that has been vaccinated with a priming vaccine comprising a first unique gp140 or gp160 glycoprotein 3-52 weeks prior, wherein the second unique gp140 or gp160 glycoprotein and the first unique gp140 or gp160 glycoprotein are immunologically distinct but share conserved sites that are not normally immunogenic for antibodies.

Further provided herein is an assay for detecting cross-protective antibodies in serum or plasma against an influenza virus comprising:
(a) incubating cells with the influenza virus and test serum sample for 1-5 days; wherein the cells express a protease that cleaves hemagglutinin of the influenza; and
(b) detecting viral infectivity compared to a control without sample;
wherein a decrease in viral infectivity at 1-5 days indicates the presence of cross-protective antibodies.

In one embodiment, the cells are from a mammalian cell line derived from the lung, airways or epithelial cells from the intestine.

Also provided herein are novel isolated complementarity determining regions, light chain variable regions, heavy chain variable regions and antibodies and fragments thereof and methods and uses thereof for cross-protection against influenza infection or for treating infection with influenza.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

The disclosure will now be described in relation to the drawings in which:

FIG. 8 shows therapeutic efficacy of a human monoclonal heterosubtypic antibody generated from a human vaccinated with the pandemic H1N1 vaccine in a lethal infection of BALB/c mice with heterologous H5N1 influenza/A virus. A. Groups of 5 mice were infected intranasally with $2 \times 10^5$ PFU of A/Hong Kong/213/2003 (H5N1) on the PR8/34 virus backbone, and treated after 24 hrs with 150 or 300 µg of V3-2G6 or after 48 hrs with 300 µg or 600 µg of V3-2G6. Controls were treated with Phosphate-buffered saline (PBS). Survival and weight-loss was monitored. B. Further reduction of the therapeutic dose of V3-2G6 to enable mice to survive from a lethal infection with H5N1. Groups of 5 mice were infected intranasally with $3 \times 10^5$ PFU of A/Hong Kong/213/2003 (H5N1) on the PR8/34 virus backbone, and treated after 24 hrs with 150 µg, 75 µg or 37.5 µg of V3-2G6. Note that all treated mice survived but there was a prolonged weight loss in the group treated with the least dose.

FIG. 9 shows cross-protection against heterologous lethal infection in mice by H5N1 influenza virus conferred by a heterosubtypic monoclonal antibody generated from a human vaccinated with the pandemic nH1N1 vaccine. Twenty-four hours before intranasal infection with $2 \times 10^5$ PFU of A/Hong Kong/213/2003 (H5N1) virus, 3 groups of 5 BALB/c mice were injected intraperitoneally with PBS as a control, or 15 ug or 5 µg of V3-2G6 generated from a subject vaccinated with the pdmH1N1 vaccine. Data shows survival rates and average weight at over 14 days.

FIG. 10 shows cross-protection against heterologous lethal infection in mice by H5N1 influenza virus conferred by plasma from a human collected at two weeks and a year after vaccination with the pandemic H1N1 vaccine. Twenty-four hours before intranasal infection with $2 \times 10^5$ PFU of A/Hong Kong/213/2003 (H5N1) virus, groups of BALB/c mice were treated with a 400 µl intraperitoneal injection of PBS as a control or plasma collected from subject V3 either 14 days post pdmH1N1 vaccination or 1 year post pdmH1N1 vaccination and as a control, plasma from a young individual collected before 2009 and thus unvaccinated and uninfected with the pandemic H1N1 influenza virus. Another group of mice were pre-treated 72, 48 and 24 hrs prior to infection with 400 µl of plasma from V3 collected 1 year after vaccination with the pandemic H1N1 vaccine.

DETAILED DESCRIPTION OF THE DISCLOSURE

Figure 1:
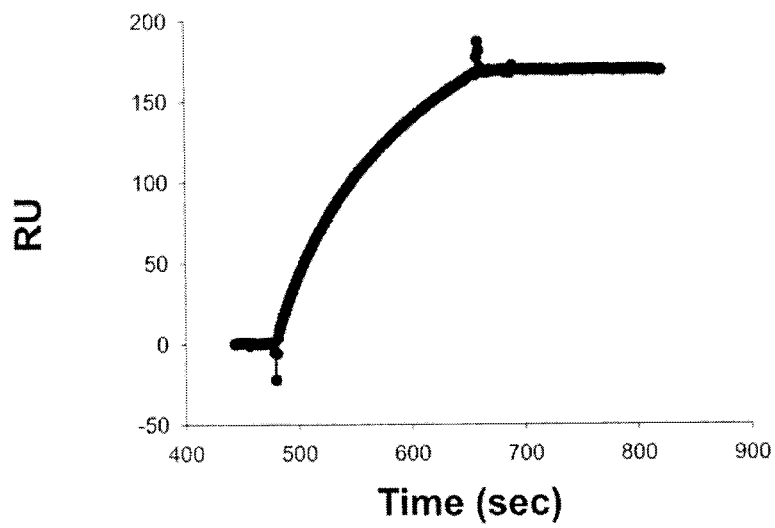
FIG. 1 shows Biacore analysis of a human monoclonal antibody (mAb) binding to the recombinant ectodomain of the HA of the 2009 pandemic H1N1 influenza virus (snH1 HA). Anti-human IgG FC was covalently coupled to a Biacore Sensor Chip CM5 via primary amine groups. Purified mAbs I4-128 (A) and I4-1G8 (B) were diluted in HBS-P (10 mM HEPES, pH 7.4, 150 mM NaCl, 0.01% Surfactant P-20) to 5 µg/ml and 750-800 RU of each captured. Purified, recombinant ectodomain of the HA of nH1N1 (snH1 HA) was diluted in HBSP to 10 µg/ml and subsequently injected. The sensorgram response (RU) shows the interaction of recombinant nH1 HA with the captured antibodies. The snH1 HA was simultaneously injected over a reference surface containing anti-human IgG FC and baseline subtracted to give the resultant sensorgram.
Figure 1:
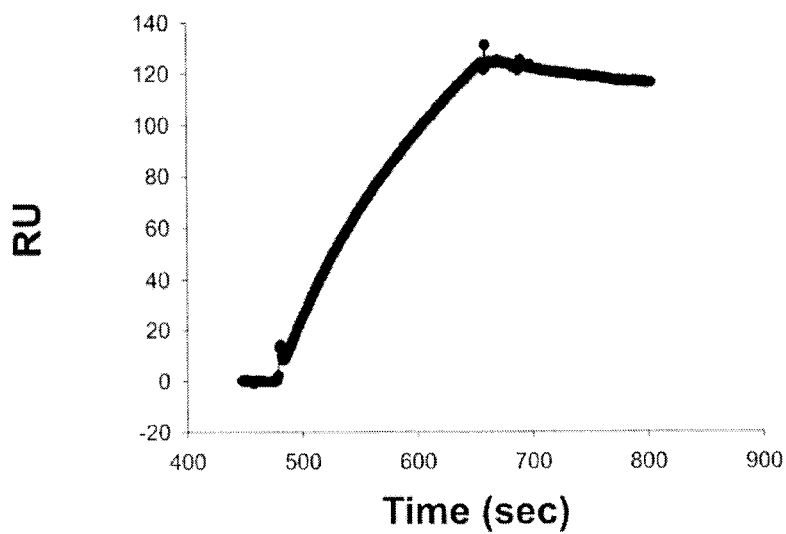

Methods and Uses for Protecting Against Pathogen Infection

The present inventor has demonstrated that a protective antibody response can be induced against a desired, conserved, functional site on a pathogen or pathogen antigen, where that site is not normally immunogenic or is minimally immunogenic because of competition in the immune response for T cell help from B cells making antibodies against other sites on the pathogen antigen. For example, the protective human antibody response to influenza is normally very isolate/strain-specific because the human immune response does not normally make a vigorous protective antibody response against sites on the virus that are conserved between strains. The present inventor has shown that this is because, in the antibody response, many memory B cells specific for other sites on the antigen, compete for T-cell help. The methods disclosed herein avoid re-stimulating the memory B cells making antibodies to readily immunogenic parts of the immunogen and thus avoid the competition between B cells that normally impedes the development of an antibody response to the conserved site, providing cross-protection against different strains and subtypes of influenza viruses.

In contrast to immune focusing by practising on naïve animals with sequential immunizations with four hemagglutinins of the same subtype H3, where a small percentage of 120 monoclonal antibodies were shown to protect against multiple H3N2 viruses circulating in humans (Wang et al 2010), the present disclosure provides methods and uses designed to elicit protective levels of cross-protective heterosubtypic antibodies in individuals who already have immunity to an influenza. The present methods/uses of sequences of unique hemagglutinins avoids stimulating memory B-cells against sites that the virus can readily vary and enables heterosubtypic antibodies that reach protective levels.

For the purpose of vaccinating a naïve human or animal to a variable pathogen to induce broadly protective antibodies, after the first immunization (which will be by definition with a unique antigen since the animal is naïve), the second and subsequent immunizations should be all with further distinct unique antigens, such that the subject to be vaccinated had undetectable or very few memory B cell making antibodies that bind tightly to these further unique antigens.

In particular, the present disclosure is based on the present demonstration that antibodies that bind to a particular site on an antigen, for example an epitope on a protein, can be difficult to raise because of competition by the relatively greater number of memory B lymphocytes that make antibodies specific for other sites on the antigen. This arises because the B lymphocytes that make the antibodies against the desired site on the antigen are less numerous than the total number of B lymphocytes that make antibodies against other sites on the antigen. These more numerous B lymphocytes specific for other epitopes on the antigen will outcompete the B lymphocytes specific for the desired epitope for resources in the lymph node and germinal centre, in particular the helper T lymphocytes specific for epitopes carried by the antigen or proteins associated with it (Allen et al, 2007, Victora, et al 2010, Schwickert et al 2011). For example, in humans, due to repeated encounters with seasonal influenza, there is a great number and frequency of B lymphocytes that make antibodies against the head of the seasonal influenza hemagglutinin molecule (Corti et al, 2010 and Wrammert et al, 2008, 2011) out-compete the less numerous B lymphocytes that make antibodies against the stem of the hemagglutinin that, unlike most of those against the head, cross-react with and neutralize many strains of influenza. Extremely low affinities are sufficient to activate memory B cells and prepare them to enter the germinal centre (Schwickert et al, 2011). In an infection or vaccination with a seasonal influenza virus that has undergone "antigenic drift", there will be many memory B cells induced by the HA head of the original virus that would still have low affinity for and be activated by the HA of the "drifted" virus. This means that the memory B cells against the original HA head would enter the germinal centres and undergo another round of affinity maturation and acquire somatic mutations that will increase the affinity for the stimulating "drifted" HA. Those memory B cells activated by low affinity interactions with the drifted HA would outcompete for T cell help those rare memory B cells against the HA stem. In contrast with the low affinity required for B cells to acquire antigen and present antigen to T cells, the affinity/avidity of antibodies against the HA head needed to block viral attachment to the host cell and thus neutralize infectivity is relatively high (Knossow et al, 2002). This means that although viruses or vaccines with drifted HA can still activate memory B cells and enter germinal centres (Wrammert et al 2008), they are not neutralized by the antibodies induced by the original virus.

In addition, memory B cells have advantages over naïve B cells in competing for T cell help. Thus memory B cells are more easily activated by antigen because they signal more efficiently than naïve B cells. They also express more proteins that co-stimulate T cells than naïve B cells and also have different migration patterns. For these reasons memory B cells, even those that cross-react weakly with an antigen on a pathogen that has been mutated to avoid neutralization by existing antibodies, can still have a competitive advantage over naïve B cells that make an antibody specific for the mutation.

Accordingly, the present disclosure provides a method of inducing a cross-protective antibody response in a subject against a pathogen comprising:
(a) administering a first unique pathogen antigen to the subject; and
(b) administering a second unique pathogen antigen 3-52 weeks, optionally 4-16 weeks, after a), wherein the second unique pathogen antigen and the first unique pathogen antigen are immunologically distinct but share conserved sites that are not normally immunogenic for antibodies.

In another embodiment, the disclosure provides a use of a second unique pathogen antigen for inducing a cross-protective antibody response in a subject that has been previously subjected to a first unique pathogen antigen 3-52 weeks, optionally 4-16 weeks, prior, wherein the second unique pathogen antigen and the first unique pathogen antigen are immunologically distinct but share conserved sites that are not normally immunogenic for antibodies.

Also provided herein is a second unique pathogen antigen for use in inducing a cross-protective antibody response in a subject that has been previously subjected to a first unique pathogen antigen 3-52 weeks, optionally 4-16 weeks, prior, wherein the second unique pathogen antigen and the first unique pathogen antigen are immunologically distinct but share conserved sites that are not normally immunogenic for antibodies.

Further provided herein is a use of a second unique pathogen antigen for preparing a boost vaccine for vaccinating a subject that has been vaccinated with a priming vaccine comprising a first unique pathogen antigen 3-52 weeks, optionally 4-16 weeks, prior, wherein the second unique pathogen antigen and the first unique pathogen antigen are immunologically distinct but share conserved sites that are not normally immunogenic for antibodies.

The term "pathogen" as used herein refers to a microorganism that causes a disease, including without limitation, a virus, bacterium, fungus or parasite.

In one embodiment, the pathogen antigen is a hemagglutinin (HA) protein of the influenza virus or a fragment thereof. In another embodiment, the pathogen antigen is a HCMV protein, for example, the gB glycoprotein, or a fragment thereof. In yet another embodiment, the pathogen antigen is an HIV protein, for example, the gp140 ectodomain of the gp160 glycoprotein. Methods and uses related to these pathogen antigens are further described herein.

In another embodiment, where there is existing immunity against the conserved sites on the pathogen, the administration of (a) the first unique antigen is unnecessary and only a single administration, as in (b), is used. In one embodiment, there is provided a use of a unique pathogen antigen for inducing a cross-protective antibody response in a subject that has existing immunity against the conserved sites on the pathogen. Also provided is a unique pathogen antigen for use in inducing a cross-protective antibody response in a subject that has existing immunity against the conserved sites on the pathogen. Further provided is a use of a unique pathogen antigen in the manufacture of a medicament for inducing a cross-protective antibody response in a subject that has existing immunity against the conserved sites on the pathogen.

In yet another embodiment, the method further comprises: (c) administering a third unique pathogen antigen 3-52 weeks, optionally 4-16 weeks, after b), wherein the third unique pathogen antigen and the first and second unique pathogen antigens are immunologically distinct but share conserved sites that are not normally immunogenic for antibodies. Also provided herein is a use of a third unique pathogen antigen for inducing a cross-protective antibody response in a subject that has been previously subjected to a second unique pathogen antigen 3-52 weeks, optionally 4-16 weeks, prior and previously has been subjected to a first unique pathogen 3-52 weeks, optionally 4-16 weeks, prior to the second unique pathogen antigen, wherein the third unique pathogen antigen and the first and second unique pathogen antigens are immunologically distinct but share conserved sites that are not normally immunogenic for antibodies. Further provided is a third unique pathogen antigen for use in inducing a cross-protective antibody response in a subject that has been previously subjected to a second unique pathogen antigen 3-52 weeks, optionally 4-16 weeks, prior, and previously has been subjected to a first unique pathogen 3-52 weeks, optionally 4-16 weeks, prior to the second unique pathogen antigen, wherein the third unique pathogen antigen and the first and second unique pathogen antigens are immunologically distinct but share conserved sites that are not normally immunogenic for antibodies. Further provided herein is a use of a third unique pathogen antigen for preparing a boost vaccine for vaccinating a subject that has been vaccinated with a priming vaccine comprising a second unique pathogen antigen 3-52 weeks, optionally 4-16 week, and previously has been subjected to a first unique pathogen 3-52 weeks, optionally 4-16 weeks, prior to the second unique pathogen antigen, wherein the third unique pathogen antigen and the first and second unique pathogen antigens are immunologically distinct but share conserved sites that are not normally immunogenic for antibodies.

The phrase "wherein the first and second unique pathogen antigens are immunologically distinct but share conserved sites that are not normally immunogenic for antibodies" as used herein means that the first unique pathogen antigen elicits antibodies that do not generally bind strongly to the second unique pathogen antigen except for conserved sites that are shared between the antigens that are not normally immunogenic or are minimally immunogenic due to competition for T cell help by the more numerous B cells stimulated by the sites that are normally immunogenic. Similarly if a third unique pathogen antigen is used, it is immunologically distinct from the first and second unique pathogen antigen but shares conserved sites that are not normally immunogenic for antibodies.

The term "unique pathogen antigen" or "unique protein" as used herein refers to a pathogen antigen or fragment thereof that is unique or unfamiliar to the subject it is desired to vaccinate, so that there are no or few memory B cells activated by contact with the "unique pathogen antigen" and there are no or low levels of antibodies circulating in the subject that bind to the unique pathogen antigen. In the "unique pathogen antigen", epitopes that typically elicit a strong antibody response in the subject are different, for example, due to mutation or deletion of amino acids or different glycosylation, from epitopes on related pathogen antigens previously encountered by the subject, whether by natural infection or vaccination. However, the "unique pathogen antigen" shares common B-cell epitopes that are the target of protective antibodies in the subject but that are normally not immunogenic because of competition for T cell help by the more numerous B cells stimulated by immunogenic parts of the pathogen antigen. The low frequency of memory B cells in the population to be vaccinated induced by the unique hemagglutinin that make antibodies that bind tightly to the putative unique antigen can be readily ascertained using the methods of Wen et al 1987 or Corti et al 2010. In the population to be vaccinated, the frequency of memory B cells making antibodies reacting strongly to the unique antigen is undetectable or less than 1 per million, or at least less than 0.01% of IgG-expressing memory B cells circulating in the blood, as ascertained using the methods of Wen et al 1987 or Corti et al 2010.

The term "pathogen antigen" as used herein refers to a pathogen or component thereof that elicits an immune response in the subject and includes, without limitation, proteins or sugars or lipids or fragments thereof or combinations thereof, expressed by the pathogen.

The phrase "sites that are not normally immunogenic" as used herein refers to sites that do not elicit a strong antibody response due to competition for T cell help by the more numerous B cells that are activated by other sites on the pathogen or pathogen antigen and includes sites that are minimally immunogenic in subjects that have been repeatedly exposed to strains of the pathogen and account for less than 5% of the antibody response against that pathogen antigen.

The term "induces a cross-protective antibody response" as used herein means that administration of an effective dose of the first unique pathogen antigen, followed by the second unique pathogen antigen as described herein, results in the production of antibodies that inhibit or reduce the severity of infection by multiple different pathogen strains or subtypes, for example, by avoiding the activation of an immunodominant population of memory B cells that make antibodies against another site on the pathogen that do not cross-protect.

To minimize competition by memory B cells activated by immunogenic sites in the first pathogen antigen that still persist in the lymph-nodes from the first administration at the time of the second administration, the second pathogen antigen optionally is administered or used at a different site.

Administration at a different site is also useful to stimulate cross-reactive, cross-protective antibody responses to various strains of a pathogen and, at the same time, to increase the levels of strain-specific antibodies to a particular strain of a pathogen. For example in the aged, the response to seasonal influenza vaccine is diminished. In this case, the present methods are useful for increasing the levels of cross-reactive, heterosubtypic cross-protective antibody levels to influenza by exploiting the cross-reactive heterosubtypic memory B cells built up by years of contact with influenza. However it may also be advantageous to also stimulate at the same time, the strain-specific antibody response to a particular strain or subtype of an influenza virus, for example the currently circulating H3N2 influenza virus. In this case the particular pathogen antigen that will induce strain-specific antibodies should be administered in a different site from the specified, unfamiliar or unique antigen designed to induce cross-protective antibodies—for example the first administration in one shoulder and the second administration in the opposite shoulder.

Accordingly, in another embodiment, the administration in b) is at a different anatomical site from the administration in a).

Administration of a pathogen antigen includes, without limitation, administration of a fragment of the pathogen antigen, or administration of the pathogen antigen as a component of a virus, optionally inactivated by methods known to those skilled in the state of the art such as a "split" vaccine plus or minus a suitable adjuvant known to those skilled in the state of the art, or a virus comprising the unique pathogen antigen that has been attenuated by methods known to those skilled in the state of the art or a viral-like particle comprising the unique pathogen antigen generated by methods known to those skilled in the state of the art or a DNA or RNA vector encoding the unique pathogen antigen using methods known to those skilled in the state of the art.

In yet another embodiment, one or more additional unique pathogen antigens are used as a mixture or concurrently with the first and/or second unique pathogen antigen. For example, the first unique pathogen antigen could be mixed with an additional unique pathogen antigen or the first unique pathogen antigen could be administered at one anatomical site and the additional unique pathogen antigen could be administered at a second anatomical site concurrently (i.e. at the same time or close together, e.g. within 24 hours). The second unique pathogen antigen would then be administered 3-52 weeks after the first administration and could also be mixed with one or more additional unique pathogen antigens or administered concurrently with one or more additional unique pathogen antigens.

Influenza Viruses

Figure 5:
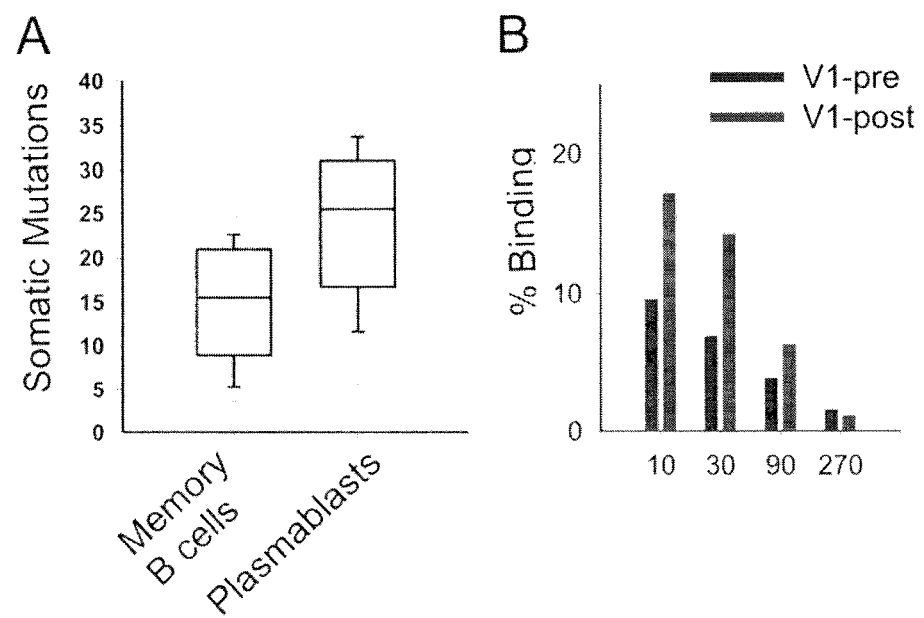
FIG. 5 shows evidence that some of the cross-reactive/heterosubtypic mAbs originated from memory B cells that were activated by nH1N1. A, Numbers of somatic mutations in IGHV-genes of mAbs generated from plasmablasts and B memory cells. Mann-Whitney Rank Sum Test of the number of somatic mutations in IGHV genes of mAbs generated from memory B cells (N=22) versus plasmablasts (N=22) demonstrates a significant difference (P=0.001). Whiskers show the ⅚sth percentile. B, Pre-existing titres of antibodies binding to cells expressing the HA of influenza A/Hong Kong/156/197 (H5N1), quantified as in FIGS. 1D and 1E, increase in the plasma of a subject 7 days after vaccination with nH1N1.

The present inventor has demonstrated that the immune response to the HA protein in humans infected or vaccinated with nH1N1, unlike the response to seasonal influenza, was dominated by antibodies that cross-reacted with the HA of other strains or sub-types of influenza virus ("cross-reactive" or "heterosubtypic"), including highly pathogenic H5N1 avian influenza, and could neutralize their infectivity. Moreover, antibodies that bound exclusively to the HA of nH1N1 were rare and only one out of 48 mAbs that bound the HA of nH1N1, failed to react with seasonal influenza vaccine (Table 1). About half (52%) of the cross-reactive or heterosubtypic antibodies used the IGHV1-69 gene (FIG. 2), which encodes the major features of a binding site for a region on the HA stem that is conserved in many subtypes of influenza virus (Ekiert et al. 2009; Sui et al. 2009). Moreover, there were 6% more heterosubtypic antibodies against the HA stem that did not use IGHV1-69. The large numbers of somatic mutations in many of these antibodies (Table 1, FIG. 5) indicated that their origin was in memory B cells, presumably induced by seasonal influenza. While most of the cross-reactive or heterosubtypic antibodies generated against the unique HA of the nH1N1 virus bound to the stem of the HA, most antibodies from one particular vaccinated individual (V2) were directed against the head of the HA as shown by the fact that they inhibited hemagglutination (e.g. V2-36, FIG. 2). The absence of memory B cells that could be activated by the antigenically unique HA head of nH1N1 enabled the relatively rare memory B cells against conserved sites on the nH1N1 HA to effectively compete for T-cell help against naïve B cells and to dominate the response. The demonstration that the nH1N1 influenza induces the production of cross-protective antibodies, establishes the feasibility of vaccination strategies for broad-spectrum protection against influenza.

Accordingly, in an embodiment, the present disclosure provides a method of inducing a cross-protective antibody response in a subject against influenza comprising:

(a) administering a first unique hemagglutinin (HA) protein to the subject; and (b) administering a second unique HA protein 3-52 weeks, optionally 4-16 weeks after a), wherein the first and second unique HA proteins are immunologically distinct but share conserved sites that are not normally immunogenic for antibodies.

In another embodiment, the disclosure provides a use of a second unique HA protein for inducing a cross-protective antibody response in a subject that has been previously subjected to a first unique HA protein 3-52 weeks, optionally 4-16 weeks prior, wherein the first and second unique HA proteins are immunologically distinct but share conserved sites that are not normally immunogenic for antibodies. The disclosure also provides a second unique HA protein for use in inducing a cross-protective antibody response in a subject that has been previously subjected to a first unique HA protein 3-52 weeks, optionally 4-16 weeks prior, wherein the first and second unique HA proteins are immunologically distinct but share conserved sites that are not normally immunogenic for antibodies. In yet another embodiment, the disclosure provides a use of a second unique HA protein for preparing a boost vaccine for vaccinating a subject that has been vaccinated with a priming vaccine comprising a first unique HA protein 3-52 weeks, optionally 4-16 weeks prior, wherein the first and second unique HA proteins are immunologically distinct but share conserved sites that are not normally immunogenic for antibodies.

The term "hemagglutinin protein" or "HA protein" as used herein refers to a protein found on the surface of influenza viruses that helps the viruses attach to receptors. A hemagglutinin protein has both a head region and a stem region. The term "hemagglutinin protein" also refers to fragments or components of the HA protein that are capable of eliciting the desired antibody response, such as the ectodomain of HA, and includes, without limitation, both protein and sugar components that are able to elicit or modify an antibody response.

The term "unique HA protein" as used herein refers to an HA protein that is unfamiliar or unique to the subject it is desired to vaccinate or induce a cross-protective antibody response in, so that there are no or few memory B cells activated by contact with the "unique HA protein" and there are no or low levels of antibodies circulating in the subject that bind to the unique HA protein. In the "unique HA protein" epitopes that typically elicit a strong antibody response in the subject are different, for example, due to mutation or deletion of amino acids or different glycosylation, from epitopes on related HA proteins previously encountered by the subject, whether by natural infection or vaccination. However, the "unique HA protein" shares common B-cell epitopes that are the target of protective antibodies but that are normally not immunogenic because of competition for T cell help by the more numerous B cells stimulated by immunogenic parts of the HA protein.

Unique hemagglutinins thus include, without limitation, the hemagglutinins of influenza virus strains that do not normally infect the species of the subject, for example like that of the H5N1 avian influenza virus for human subjects, or for example, in humans, hemagglutinins that are antigenically distinct and have little reactivity with antibodies against the strains of H1N1 and H3N2 seasonal influenza viruses which have been circulating in humans. An example of a unique HA in most of the human population is the HA of the 2009 pandemic influenza H1N1 strain as many humans had no circulating antibodies that could bind to it and neutralize its infectivity (Itoh et al. 2009) and thus lacked the memory B cells that could be activated by the hemagglutinin head or made antibodies of low affinity with the head of the hemagglutinin of the nH1N1 such that they could not compete against rare memory B cells making cross-protective antibodies against a conserved site on the hemagglutinin stem.

The published literature indicates that the cross-reactive antibodies against the H5 HA stem region fail to cross-react with H3 or H7 hemagglutinins (Sui et al. 2009). However there is evidence that antibodies can be induced in mice, which cross-react with a variety of H3 influenza viruses (Wang et al. 2010). Therefore the methods and uses disclosed herein can be practiced to induce antibodies which cross-react with a variety of H3 influenza by ensuring that subjects are administered an H3 HA that is novel to that population. Unique H3 HA include, without limitation, an H3 influenza virus that circulated many years ago and which sera from the population does not display reactivity to, an H3 influenza virus that was circulating in another species independent of human contact, and a mutated or chimeric HA that exhibited the stem of the H3 HA but that lacked epitopes on the head that the sera from the population to be vaccinated reacted with.

Also the literature indicates that there are conserved epitopes on the hemagglutinin head that can cross neutralize influenza A viruses from different subtypes and across group 1 and Group 2 subtypes of hemagglutinin (Yoshida et al, 2009). Therefore by sequentially immunizing with unique hemagglutinins from Group 1 and/or Group 2 of hemagglutinins, broadly cross-protective antibodies will be induced.

In all cases, these hemagglutinins are "unique" in the sense that they lack B cell epitopes that are strongly immunogenic in the subject to be vaccinated because they cannot activate many memory B cells in the subjects to be vaccinated and do not bind, or bind to only low levels with low affinity to antibodies circulating in the subjects to be vaccinated. Nevertheless they exhibit conserved epitopes that are critical for function, for example on the HA stem that support fusion. Optionally these unique hemagglutinins preserve the trimeric structure.

The term "cross-protective antibody response" as used herein refers to eliciting an antibody response to multiple strains of pathogens, such as influenza, strains and/or subtypes.

The term "antigenic sites" as used herein refers to sites on the HA protein capable of eliciting an immune response. Thus, "conserved antigenic sites" refers to sites present in both the first and second unique HA protein.

Administration of a hemagglutinin (HA) includes without limitation, administration of at least the ectodomain of the hemagglutinin, or administration of the hemagglutinin as a component of a virus, optionally inactivated by methods known to those skilled in the state of the art such as a "split" vaccine plus or minus a suitable adjuvant known to those skilled in the state of the art, or a virus comprising the unique HA that has been attenuated by methods known to those skilled in the state of the art or a viral-like particle comprising the unique HA generated by methods known to those skilled in the state of the art or a DNA or RNA vector encoding the unique HA using methods known to those skilled in the state of the art.

Accordingly, in one embodiment, the first and/or second unique HA protein is from a pandemic virus or a virus that normally infects a different host species. In one embodiment, the virus that infects a different host species is a virus that infects an avian species or a virus that infects swine.

In another embodiment, the first and/or second unique HA protein is part of an attenuated or inactivated influenza virus strain.

The term "inactivated influenza virus strain" as used herein refers to an influenza virus strain that is not infectious. For example, an influenza virus can be inactivated by dilute formaldehyde or beta-propiolactone followed by a detergent treatment called splitting (Bardiya and Bae, 2005).

The term "attenuated influenza virus strain" as used herein refers to a virus that is live but has reduced virulence. Methods of rendering a live virus less virulent are known in the art and involve cold adaptation or other methods (Bardiya and Bae, 2005). An advantage of live viruses is that they can be administered via nasal insufflation and/or at lower concentrations of virus rendering large-scale inoculations less expensive. Live virus for example elicits diverse and/or heightened immune responses in the recipient of the HA protein, including for example systemic, local, humoral and cell-mediated immune responses.

Alternatively, the first and/or second unique HA protein is an artificial HA protein, optionally in a form that preserves the trimeric ectodomain of HA. Artificial HA proteins are designed to include mutations in the surface of the HA head that make it antigenically unrelated to HA that the population to be vaccinated has been exposed to. Such proteins may be expressed by a vector comprising DNA sequences that encode the HA protein.

One method of artificially generating a unique hemagglutinin is to mutate surface exposed residues on the head of the hemagglutinin of a seasonal influenza virus strain to disrupt the existing B cell epitopes, while maintaining the antigenic sites on the stem.

In yet another embodiment, the first and/or second unique HA protein is a chimeric protein, which comprises a conserved stem coupled to a head of a unique HA protein.

In one embodiment, artificial or chimeric HA proteins comprise T-cell epitopes, optionally linked to the HA protein by fusion, chemically or physically, that the subject has been immunized against, for example, a peptide from tetanus toxoid. In another embodiment, where the whole virus, inactivated or attenuated, is administered, the T cell help is provided by epitopes on other proteins in the virion.

In yet a further embodiment, the second unique HA protein comprises a head that is substantially antigenically unrelated to the first unique HA protein but comprises conserved antigenic sites in the stem or head that are normally not immunogenic for antibodies. The term "substantially antigenically unrelated" as used herein means that sites or epitopes on the first and second unique HA protein that normally elicit a strong antibody response in the subject are different for example of a different HA subtype from the first unique antigen such that subjects to be vaccinated or subjects vaccinated with step a) have sera that do not neutralize in vitro the infectivity of an influenza virus exhibiting the unique hemagglutinin by the WHO standard assay, or have an hemagglutination inhibition assay titre against an influenza virus exhibiting the unique hemagglutinin of less than 40. The antigens are designed so that the second unique antigen does not activate many memory B cells against the head induced by the first unique antigen. The low frequency of memory B cells induced by the first the unique hemagglutinin that make antibodies that bind tightly to the second putative unique antigen can be readily ascertained using the methods of Wen et al 1987 or Corti et al 2010.

In another embodiment, the first unique hemagglutinin protein is a member of Group 1 subtypes of HA protein and the second unique hemagglutinin is a member of a Group 2 subtypes of HA protein or the first unique hemagglutinin protein is a Group 2 HA protein and the second unique hemagglutinin is a Group 1 HA protein. The term "Group 1 HA" as used herein refers to the hemagglutinins of the subtypes H1, H2, H5, H6, H8, H9, H11, H12, H13 and H16. The term "Group 2 HA" as used herein refers to the hemagglutinins of the subtypes H3, H4, H7, H10, H14 and H15.

In yet another embodiment, one or more additional unique HA proteins are used as a mixture or concurrently with the first and/or second unique HA protein. For example, the first unique hemagglutinin protein could be a Group 1 HA protein and could be mixed with a Group 2 HA protein or the Group 1 HA protein could be administered at one anatomical site and the Group 2 HA protein at a second anatomical site concurrently (i.e. at the same time or close together, e.g. within 24 hours). The second unique hemagglutinin protein would then be administered 3-52 weeks after the first administration and could also be mixed with one or more additional unique HA proteins or administered concurrently with one or more additional unique HA proteins.

Also provided herein is a kit comprising a first unique hemagglutinin (HA) protein as disclosed herein and second hemagglutinin (HA) protein as disclosed herein, wherein the first HA protein and the second HA protein are immunologically distinct but share conserved sites that are not normally immunogenic for antibodies. In one embodiment, the first HA protein comprises a head that is different from the second HA protein and the first HA protein and the second HA protein comprise a stem having conserved antigenic sites that are not normally immunogenic.

In one embodiment the kit is used for inducing a cross-protective antibody response in a subject.

In an embodiment, the kit further comprises an instrument for administering the HA proteins and/or instructions for use and/or a container.

Human Cytomegaloviruses (HCMV)

There is also a great need for a vaccine that will protect against HCMV. Antibodies against a linear epitope on the gB glycoprotein termed the AD-2 epitope can neutralize infectivity of multiple strains of HCMV. However, antibodies against AD-2 are generated in only a minority of humans vaccinated with previous vaccines and are not generated even in many infected humans. The present inventor has shown that human antibodies against AD-2 have to have a very specific structure and are usually derived from a single pair of immunoglobulin V-genes (McLean et al. 2005; McLean et al. 2006; Thomson et al. 2008); these structural constraints mean that B lymphocytes specific for AD-2 are relatively infrequent as compared with B lymphocytes that are specific for another epitope on the ectodomain of the gB protein, AD-1. The methods described herein allow for decreased competition from AD-1 specific B lymphocytes.

Accordingly, in another embodiment, the present disclosure provides a method of inducing a cross-protective antibody response in a subject against human cytomegalovirus (HCMV) comprising:

(a) administering a gB glycoprotein or a fragment thereof comprising the gB ectodomain to the subject; and
(b) administering a modified gB glycoprotein 3-52 weeks, optionally 4-16 weeks, after a), wherein the modified gB glycoprotein lacks the AD-1 epitope.

In another embodiment, the disclosure provides a use of a modified gB glycoprotein for inducing a cross-protective antibody response in a subject that has been previously subjected to a gB glycoprotein or its ectodomain 3-52 weeks, optionally 4-16 weeks prior, wherein the modified gB glycoprotein lacks the AD-1 epitope. The disclosure also provides a modified gB glycoprotein for use in inducing a cross-protective antibody response in a subject that has been previously subjected to a gB glycoprotein or its ectodomain 3-52 weeks, optionally 4-16 weeks prior, wherein the modified gB glycoprotein lacks the AD-1 epitope. In yet another embodiment, the disclosure provides a use of a modified gB glycoprotein for preparing a boost vaccine for vaccinating a subject that has been vaccinated with a priming vaccine comprising a gB glycoprotein or its ectodomain 3-52 weeks, optionally 4-16 weeks prior, wherein the modified gB glycoprotein lacks the AD-1 epitope.

The phrase "lacks the AD-1 epitope" as used herein refers to a protein or virus containing the gB protein wherein the AD-1 epitope is mutated or absent. This allows expansion of the levels of relatively rare memory B lymphocytes or naïve B cells that make high affinity antibodies against the AD-2 epitope. In one embodiment, a fragment of gB that lacks the AD-1 epitope but preserves AD-2 is used. Such a fragment may be made up of the N-terminal ~70-100 amino acids of the gB protein. This fragment does not include the amino acids that comprise the AD-1 epitope (Wagner et al 1992). It has been demonstrated that neutralizing antibodies that bind to the AD-2 epitope bind more tightly to this N-terminal fragment of gB than they bind to the AD-2 linear peptide, indicating that in this fragment the AD-2 peptide adopts the configuration it does in the native gB (Thomson et al. 2008).

Also provided herein is a kit comprising a gB protein as disclosed herein and a modified gB protein as disclosed herein, wherein the modified gB glycoprotein lacks the AD-1 epitope.

In one embodiment the kit is used for inducing a cross-protective antibody response in a subject.

In an embodiment, the kit further comprises an instrument for administering the gB proteins and/or instructions for use and/or a container.

Human Immune-Deficiency Virus (HIV)

It will be evident to those skilled in the art, that the presently disclosed methodology is also useful for eliciting broadly neutralizing antibodies against the envelope protein of HIV-1 gp160 or the ectodomain gp140 (Karlsson Hehestam et al 2008, and Kwong and Wilson 2009).

Accordingly, in yet another embodiment the present disclosure provides a method of inducing a cross-protective neutralizing antibody response in a subject against HIV-1 comprising:
(a) administering a first unique gp140 or gp160 glycoprotein to the subject; and
(b) administering a second unique gp140 or gp160 protein, 3-52 weeks after a);
wherein the second unique gp140 or gp160 glycoprotein and the first unique gp140 or gp160 glycoprotein are immunologically distinct but share conserved sites that are not normally immunogenic for antibodies.

In another embodiment, the disclosure provides a use of a second unique gp140 or gp160 glycoprotein for inducing a cross-protective antibody response in a subject that has been previously subjected to immunization with a first unique gp140 or gp160 glycoprotein 3-52 weeks prior; wherein the second unique gp140 or gp160 glycoprotein and the first unique gp140 or gp160 glycoprotein are immunologically distinct but share conserved sites that are not normally immunogenic for antibodies.

The disclosure also provides second unique gp140 or gp160 glycoprotein for use in inducing a cross-protective antibody response in a subject that has been previously subjected to immunization with a first unique gp140 or gp160 glycoprotein 3-52 weeks prior; wherein the second unique gp140 or gp160 glycoprotein and the first unique gp140 or gp160 glycoprotein are immunologically distinct but share conserved sites that are not normally immunogenic for antibodies.

In yet another embodiment, the disclosure provides a use of a second unique gp140 or gp160 glycoprotein for preparing a boost vaccine for vaccinating a subject that has been vaccinated with a priming vaccine comprising a first unique gp140 or gp160 glycoprotein 3-52 weeks prior, wherein the second unique gp140 or gp160 glycoprotein and the first unique gp140 or gp160 glycoprotein are immunologically distinct but share conserved sites that are not normally immunogenic for antibodies.

The term "unique gp140 or gp160 glycoprotein" as used herein refers to a gp140 or gp160 glycoprotein or fragment thereof that is unique or unfamiliar to the subject it is desired to vaccinate, so that there are no or few memory B cells activated by contact with the "unique gp140 or gp160 glycoprotein" and there are no or low levels of antibodies circulating in the subject that bind to the unique gp140 or gp160 glycoprotein. In the "unique gp 140 or gp160 glycoprotein", epitopes that typically elicit a strong antibody response in the subject are different, for example, due to mutation or deletion of amino acids or different glycosylation, from epitopes on related gp140 or gp160 glycoproteins previously encountered by the subject, whether by natural infection or vaccination. However, the "unique gp140 or gp160 glycoprotein" shares common B-cell epitopes that are the target of protective antibodies in the subject but that are normally not immunogenic because of competition for T cell help by the more numerous B cells stimulated by immunogenic parts of the pathogen antigen.

The low frequency of memory B cells in the population to be vaccinated induced by the unique glycoprotein that make antibodies that bind tightly to the putative unique protein can be readily ascertained using the methods of Wen et al 1987 or Corti et al 2010.

Also provided herein is a kit comprising a first unique gp140 or gp160 glycoprotein as disclosed herein and a second gp140 or gp160 glycoprotein as disclosed herein, wherein the first gp140 or gp160 glycoprotein and the second gp140 or gp160 glycoprotein are immunologically distinct but share conserved sites that are not normally immunogenic for antibodies.

In one embodiment the kit is used for inducing a cross-protective antibody response in a subject.

In an embodiment, the kit further comprises an instrument for administering the gp140 or gp160 glycoproteins and/or instructions for use and/or a container.

The term "subject" as used herein refers to any member of the animal kingdom, optionally humans. For example, a subject that is susceptible to influenza infection, includes, without limitation, birds, pigs, horses and humans.

In an embodiment, the methods and/or uses described herein further comprise administration of an adjuvant with the first and/or second pathogen antigen and/or third pathogen antigen or unique proteins disclosed herein. The term "adjuvant" as used herein refers to a substance that is able to enhance the immunostimulatory effects of the pathogen antigens described herein but does not have any specific antigenic effect itself. Typical adjuvants include, without limitation, Freund's adjuvant, aluminium salts, squalene, poly I:C, GM-CSF, SB-AS2, Ribi adjuvant system, Gerbu adjuvant, CpG and monophosphoryl Lipid A and approved proprietary adjuvants such as AS03 adjuvant system, an emulsion composed of DL-a-tocopherol, squalene and polysorbate 8 developed by GlaxoSmithKline (GSK).

The immunologically effective amount will, as a person of skill in the art will understand, vary with the formulation, the route of administration, the host being treated and the like but can nevertheless be routinely determined by one skilled in the art.

The pathogen antigens or proteins disclosed herein in an embodiment are suitably formulated as a liquid formulation, a solid formulation or a spray formulation.

In an embodiment, the pathogen antigens or proteins disclosed herein are suitably formulated for oral, for example via drinking water and/or combined with food; intranasal, for example via spray; eye drop; intramuscular; intradermal; subcutaneous; intravenous and/or intraperitoneal administration.

In one embodiment, the first and/or second pathogen antigen or proteins disclosed herein are administered subcutaneously, intramuscularly, intraperitoneally or intranasally. In an embodiment, the method of administration is the same for the first and second pathogen antigen or protein disclosed herein. In an alternate embodiment, the method of administration is different for the first and second pathogen antigen or protein disclosed herein.

Suitable carriers and/or pharmaceutically acceptable carriers include for example water, including sterile water, saline, ethanol, ethylene glycol, glycerol, water in oil emulsions, oil in water emulsions, saponins and alum based carriers etc and coformulants may be added. Pharmaceutically acceptable carriers include for example suitable carriers that are suitable for animal administration, for example which have been filtered for sterility. Suitable vehicles are described, for example, in Remington's Pharmaceutical Sciences (Remington's Pharmaceutical Sciences, 20th ed., Mack Publishing Company, Easton, Pa., USA, 2000).

Assays for Detecting Cross-Protective Antibodies

In order to detect heterosubtypic antibodies that neutralize infectivity and are thus likely to be protective—for the purposes of assessing vaccination regimens or for screening for therapeutic or prophylactic monoclonal antibodies, an assay must be sensitive to all inhibitory antibodies, whether they neutralize by blocking binding of the virus to the host cells or whether they block at a later step by blocking the conformational change in the HA stem that is necessary for the fusion of the membranes of the virus and the endosome and thus entry of the viral genome into the cytosol.

The standard WHO microneutralization assay only allows the mixture of the antibodies under test and the challenge virus to be in contact with the host cells for only a few hours after which the antibodies and virus are removed and then cells are incubated for 1-5 days to allow the infection to develop. Thus, the antibodies have to act in the first few hours of the infection. For conventional neutralizing antibodies that bind to the HA head and block the attachment of the HA of the virus to its receptor on the host cell, this does not matter. However, for antibodies that block infectivity by binding to the HA stem and inhibit fusion of the virus to the endosomal membrane, they may have to be present in higher concentrations for longer time periods to block infectivity. Assays where antibodies are present for the entire 1-5 day assay, allow antibodies to bind to the HA stem and neutralize, while they do not in the standard assay.

Accordingly, also provided herein is an assay for detecting cross-protective antibodies against an influenza virus comprising:
 (a) incubating cells with the influenza virus and test serum sample for 1-5 days; wherein the cells express a protease that cleaves hemagglutinin of the influenza virus; and
 (b) detecting viral infectivity compared to a control without sample;
 wherein a decrease in viral infectivity at 1-5 days indicates the presence of cross-protective antibodies.

The term "viral infectivity" as used herein refers to the ability of the virus to infect the host cells and can be evaluated by the amount of viral proteins present or by the amount of cell survival. Thus, detecting viral infectivity includes, without limitation, detecting the amount of viral proteins and/or detecting cell survival.

In one embodiment, detecting viral infectivity comprises detecting cell survival and a decrease in viral infectivity comprises an increase in cell survival.

The term "control" as used herein refers to a sample from a subject or a group of subjects who have not been infected or vaccinated with novel or unique influenza. The term also includes a predetermined standard.

Cleavage of hemagglutinin is necessary for the hemagglutinin to undergo the conformational change that is necessary for fusion of the viral membrane with that of the host cell. Some avian influenza viruses for example are readily cleaved by enzymes prevalent in many cells. However for human and mammalian influenza viruses the enzymes that cleave the hemagglutinin are only present in a restricted set of cells which include, without limitation, the cells that line the lungs. Therefore for many years the assay that was used to detect neutralizing antibodies that are likely to be protective used mammalian cells (usually canine MDCK cells) and relied on including in the medium a proteolytic enzyme such as TCPK-trypsin. For this reason, in the standard WHO microneutralization assay, the serum and virus mixture is incubated with the MDCK cells for 2-3 hours and then removed lest it inhibit TCPK-trypsin.

Accordingly, in one embodiment, the cell line is a mammalian cell-line derived from the lung, airways or epithelial cells of the intestine. For example one human cell line that originates from the human airway is A549, which expresses proteolytic enzymes, which normally cleave influenza hemagglutinin such as TMPRSS2 and HAT.

In another embodiment, the hemagglutinin of the influenza virus against which it is desired to detect neutralizing antibodies against the stem may be mutated at the cleavage site making it readily cleavable intracellularly like the hemagglutinin of avian influenza viruses.

Method for Generating Monoclonal Antibodies Cross-Protective Against Influenza

The present demonstration that cross-reactive antibodies are produced are dominant in the response to an unfamiliar hemagglutinin allows for the generation of monoclonal antibodies that cross-react with multiple influenza strains and/or subtypes. Accordingly also provided herein is a method of generating monoclonal antibodies, optionally human, cross-protective against influenza comprising:
 (a) isolating cells from a sample of blood or other tissue containing cells of the immune system from a subject that has been infected or vaccinated with an influenza strain that exhibits a unique hemagglutinin;
 (b) preparing monoclonal antibodies using the cells of (a); and
 (c) selecting monoclonal antibodies that cross-react with different strains and subtypes of viruses or that bind to the stem of the hemagglutinin.

In one embodiment, the subject has been vaccinated using one of the methods or uses described herein for inducing a cross-protective antibody response to influenza.

The method for deriving immune cells that contain cells making antibodies that cross-react with and neutralize many types of influenza viruses, will be useful for the generation of monoclonal antibodies produced by a variety of methods well known to those skilled in the art, including display-based library techniques, immortalization or hybridoma techniques, or methods that rely on cloning or sequencing cDNA or RNA that encode immunoglobulins from selected single cells that make the desired antibodies. Mixtures of monoclonal antibodies cross-reactive against multiple strains generated by this method may be combined to minimize the emergence of mutant strains that escape the neutralization by these antibodies.

To produce human monoclonal antibodies, antibody producing cells (lymphocytes) can be harvested from a human infected with influenza and fused with myeloma cells by standard somatic cell fusion procedures thus immortalizing these cells and yielding hybridoma cells. Such techniques are well known in the art, (e.g. the hybridoma technique originally developed by Kohler and Milstein (*Nature* 256: 495-497 (1975)) as well as other techniques such as the human B-cell hybridoma technique (Kozbor et al., *Immunol. Today* 4:72 (1983)), the EBV-hybridoma technique to produce human monoclonal antibodies (Cole et al., *Methods Enzymol,* 121:140-67 (1986)) or EBV immortalization of activated B cells (Pinna et al. 2009), and screening of combinatorial antibody libraries (Huse et al., *Science* 246: 1275 (1989)). Monoclonal antibodies can be screened immunochemically for production of antibodies specifically reactive with hemagglutinin and the monoclonal antibodies can be isolated. Optional methods are described in patent application PCT/CA 2006/001074.

Cross-Protective and/or Novel Monoclonal Antibodies to Influenza

The present inventor has obtained and sequenced ten human monoclonal antibodies cross-protective and/or novel to influenza using methods described in patent application PCT/CA2006/001074, incorporated herein by reference. The human monoclonal antibodies were developed from exposure of the human immune system to a unique hemagglutinin that was immunologically distinct from the HA of other influenza viruses that humans in general had been exposed to. In the present case, the HA of the 2009 (H1N1) pandemic influenza virus of swine origin is antigenically unrelated to the hemagglutinin of any strain of influenza virus to which most humans had been previously exposed to through infections or vaccinations, such that few humans had neutralizing antibodies against it (Itoh et al, 2009). The exposure to the unique HA meant that there were very few memory B cells that made antibodies that cross-react with the head of nH1N1 HA and thus could be activated by it. This circumstance allowed the relatively rare memory B cells that recognized regions of the HA that were conserved with seasonal influenza viruses that the humans had been exposed to be activated by the HA of the nH1N1 and to access T-cell help and undergo affinity maturation. These memory B cells include those making antibodies against the conserved region of the stem and also some making antibodies against conserved regions of the head of the HA.

The inventor has obtained ten monoclonal antibodies, V2-36, V2-7, V3-2G6, I8-1B6, V3-3D2, V3-1G10, I5-24, I4-128, V4-17 and V3-2C3, and determined the sequence of the light and heavy chain variable regions and complementarity determining regions 1, 2 and 3 of the antibodies (Table 2).

Given the disclosure of the sequence of the heavy chain and light chain variable region that determine the binding characteristics of a given antibody, a person skilled in the art would readily be able to determine sequences of nucleotides that specify the synthesis of the antibody that is disclosed.

The inventor has obtained the amino acid sequences of the variable regions of V2-36. Accordingly, the disclosure provides isolated light chain complementarity determining region 1 (CDR1) comprising the amino acid sequence YSNIGTGFD (SEQ ID NO:1); isolated light chain complementarity determining region 2 (CDR2) comprising the amino acid sequence GNN (SEQ ID NO:2); isolated light chain complementarity determining region 3 (CDR3) comprising the amino acid sequence QSFDSSLSGSNV (SEQ ID NO:3); isolated heavy chain CDR1 comprising the amino acid sequence GGSISGGSHY (SEQ ID NO:4); isolated heavy chain CDR2 comprising the amino acid sequence IYYSGST (SEQ ID NO:5); and isolated heavy chain CDR3 comprising the amino acid sequence AKHESDSSSWHTGWNWFDP (SEQ ID NO:6).

The disclosure also includes isolated nucleic acid sequences encoding the light chain complementarity determining region 1 (CDR1) comprising the amino acid sequence YSNIGTGFD (SEQ ID NO:1); the light chain complementarity determining region 2 (CDR2) comprising the amino acid sequence GNN (SEQ ID NO:2); the light chain complementarity determining region 3 (CDR3) comprising the amino acid sequence QSFDSSLSGSNV (SEQ ID NO:3); the heavy chain CDR1 comprising the amino acid sequence GGSISGGSHY (SEQ ID NO:4); the heavy chain CDR2 comprising the amino acid sequence IYYSGST (SEQ ID NO:5); and the heavy chain CDR3 comprising the amino acid sequence AKHESDSSSWHTGWNWFDP (SEQ ID NO:6).

Also provided are isolated light chain variable regions comprising light chain CDR1, CDR2 and/or CDR3 disclosed herein (SEQ ID NOS:1, 2 and/or 3), and isolated heavy chain variable regions comprising heavy chain CDR1, CDR2 and/or CDR3 disclosed herein (SEQ ID NOS:4, 5 and/or 6). In one embodiment, the light chain variable region comprises the amino acid sequence shown in SEQ ID NO:7. In another embodiment, the heavy chain variable region comprises the amino acid sequence shown in SEQ ID NO:8.

The disclosure also includes an isolated nucleic acid sequence encoding the light chain variable region comprising the amino acid sequence shown in SEQ ID NO:7, and an isolated nucleic acid sequence encoding the heavy chain variable region comprising the amino acid sequence shown in SEQ ID NO:8.

The disclosure further provides an antibody or antibody fragment comprising at least one light chain complementarity determining region as shown in SEQ ID NOs:1-3 and/or at least one heavy chain complementarity determining region as shown in SEQ ID NOs:4-6.

In one embodiment, the antibody or antibody fragment comprises the light chain CDR sequences of SEQ ID NOS:1, 2 and 3 and/or the heavy chain CDR sequences of SEQ ID NOS:4, 5 and 6. In another embodiment, the antibody or antibody fragment comprises the amino acid of SEQ ID NO: 7 (light chain variable region) and/or the amino acid of SEQ ID NO:8 (heavy chain variable region).

The inventor has obtained the amino acid sequences of the variable regions of antibody V2-7. Accordingly, the disclosure provides isolated light chain complementarity determining region 1 (CDR1) comprising the amino acid sequence STNIGAGLA (SEQ ID NO:9); isolated light chain complementarity determining region 2 (CDR2) comprising the amino acid sequence GNT (SEQ ID NO:10), isolated light chain complementarity determining region 3 (CDR3) comprising the amino acid sequence QSFDGSLSGSNV (SEQ ID NO:11); isolated heavy chain CDR1 comprising the amino acid sequence GGSIRGGTNY (SEQ ID NO:12); isolated heavy chain CDR2 comprising the amino acid sequence VYYSGST (SEQ ID NO:13); and isolated heavy chain CDR3 comprising the amino acid sequence ARHESDSSSWHTGWNWFDP (SEQ ID NO:14).

The disclosure also includes isolated nucleic acid sequences encoding the light chain complementarity determining region 1 (CDR1) comprising the amino acid sequence STNIGAGLA (SEQ ID NO:9); the light chain complementarity determining region 2 (CDR2) comprising the amino acid sequence GNT (SEQ ID NO:10); the light chain complementarity determining region 3 (CDR3) comprising the amino acid sequence QSFDGSLSGSNV (SEQ ID NO:11); the heavy chain CDR1 comprising the amino acid sequence GGSIRGGTNY (SEQ ID NO:12); the heavy chain CDR2 comprising the amino acid sequence VYYSGST (SEQ ID NO:13); and the heavy chain CDR3 comprising the amino acid sequence ARHESDSSSWHTGWNWFDP (SEQ ID NO:14).

Also provided are isolated light chain variable regions comprising light chain CDR1, CDR2 and/or CDR3 disclosed herein (SEQ ID NOS:9, 10 and/or 11), and isolated heavy chain variable regions comprising heavy chain CDR1, CDR2 and/or CDR3 disclosed herein (SEQ ID NOS:12, 13 and/or 14). In one embodiment, the light chain variable region comprises the amino acid sequence shown in SEQ ID NO:15. In another embodiment, the heavy chain variable region comprises the amino acid sequence shown in SEQ ID NO:16.

The disclosure also includes an isolated nucleic acid sequence encoding the light chain variable region comprising the amino acid sequence shown in SEQ ID NO:15, and an isolated nucleic acid sequence encoding the heavy chain variable region comprising the amino acid sequence shown in SEQ ID NO:16.

The disclosure further provides an antibody or antibody fragment comprising at least one light chain complementarity determining region as shown in SEQ ID NOs:9-11 and/or at least one heavy chain complementarity determining region as shown in SEQ ID NOs:12-14.

In one embodiment, the antibody or antibody fragment comprises the light chain CDR sequences of SEQ ID NOS:9, 10 and 11 and/or the heavy chain CDR sequences of SEQ ID NOS:12, 13 and 14. In another embodiment, the antibody or antibody fragment comprises the amino acid of SEQ ID NO: 15 (light chain variable region) and/or the amino acid of SEQ ID NO:16 (heavy chain variable region).

The inventor has obtained the amino acid sequences of the variable regions of V3-2G6. Accordingly, the disclosure provides isolated light chain complementarity determining region 1 (CDR1) comprising the amino acid sequence QIVSSSQ (SEQ ID NO:17); isolated light chain complementarity determining region 2 (CDR2) comprising the amino acid sequence AAS (SEQ ID NO:18); isolated light chain complementarity determining region 3 (CDR3) comprising the amino acid sequence QQYGTSHA (SEQ ID NO:19); isolated heavy chain CDR1 comprising the amino acid sequence GGTFSSFA (SEQ ID NO:20); isolated heavy chain CDR2 comprising the amino acid sequence IIGMFGTT (SEQ ID NO:21); and isolated heavy chain CDR3 comprising the amino acid sequence ARGKKYYHDTLDY (SEQ ID NO:22).

The disclosure also includes isolated nucleic acid sequences encoding the light chain complementarity determining region 1 (CDR1) comprising the amino acid sequence QIVSSSQ (SEQ ID NO:17); the light chain complementarity determining region 2 (CDR2) comprising the amino acid sequence AAS (SEQ ID NO:18); the light chain complementarity determining region 3 (CDR3) comprising the amino acid sequence QQYGTSHA (SEQ ID NO:19); the heavy chain CDR1 comprising the amino acid sequence GGTFSSFA (SEQ ID NO:20); the heavy chain CDR2 comprising the amino acid sequence IIGMFGTT (SEQ ID NO:21); and the heavy chain CDR3 comprising the amino acid sequence ARGKKYYHDTLDY (SEQ ID NO:22).

Also provided are isolated light chain variable regions comprising light chain CDR1, CDR2 and/or CDR3 disclosed herein (SEQ ID NOS:17, 18 and/or 19), and isolated heavy chain variable regions comprising heavy chain CDR1, CDR2 and/or CDR3 disclosed herein (SEQ ID NOS:20, 21 and/or 22). In one embodiment, the light chain variable region comprises the amino acid sequence shown in SEQ ID NO:23. In another embodiment, the heavy chain variable region comprises the amino acid sequence shown in SEQ ID NO:24.

The disclosure also includes an isolated nucleic acid sequence encoding the light chain variable region comprising the amino acid sequence shown in SEQ ID NO:23, and an isolated nucleic acid sequence encoding the heavy chain variable region comprising the amino acid sequence shown in SEQ ID NO:24.

The disclosure further provides an antibody or antibody fragment comprising at least one light chain complementarity determining region as shown in SEQ ID NOs:17-19 and/or at least one heavy chain complementarity determining region as shown in SEQ ID NOs:20-22.

In one embodiment, the antibody or antibody fragment comprises the light chain CDR sequences of SEQ ID NOS: 17, 18 and 19 and/or the heavy chain CDR sequences of SEQ ID NOS:20, 21 and 22. In another embodiment, the antibody or antibody fragment comprises the amino acid of SEQ ID NO: 23 (light chain variable region) and/or the amino acid of SEQ ID NO:24 (heavy chain variable region).

The inventor has obtained the amino acid sequences of the variable regions of I8-1B6. Accordingly, the disclosure provides isolated light chain complementarity determining region 1 (CDR1) comprising the amino acid sequence NSDVGTYNY (SEQ ID NO:25); isolated light chain complementarity determining region 2 (CDR2) comprising the amino acid sequence DVS (SEQ ID NO:26); isolated light chain complementarity determining region 3 (CDR3) comprising the amino acid sequence SSYTTSNTRV (SEQ ID NO:27); isolated heavy chain CDR1 comprising the amino acid sequence GGIFSNFA (SEQ ID NO:28); isolated heavy chain CDR2 comprising the amino acid sequence ILSIFRTT (SEQ ID NO:29); and isolated heavy chain CDR3 comprising the amino acid sequence ARSITNLYYYYMDV (SEQ ID NO:30).

The disclosure also includes isolated nucleic acid sequences encoding the light chain complementarity determining region 1 (CDR1) comprising the amino acid sequence NSDVGTYNY (SEQ ID NO:25); the light chain complementarity determining region 2 (CDR2) comprising the amino acid sequence DVS (SEQ ID NO:26); the light chain complementarity determining region 3 (CDR3) comprising the amino acid sequence SSYTTSNTRV (SEQ ID NO:27); the heavy chain CDR1 comprising the amino acid sequence GGIFSNFA (SEQ ID NO:28); the heavy chain CDR2 comprising the amino acid sequence ILSIFRTT (SEQ ID NO:29); and the heavy chain CDR3 comprising the amino acid sequence ARSITNLYYYYMDV (SEQ ID NO:30).

Also provided are isolated light chain variable regions comprising light chain CDR1, CDR2 and/or CDR3 disclosed herein (SEQ ID NOS:25, 26 and/or 27), and isolated heavy chain variable regions comprising heavy chain CDR1, CDR2 and/or CDR3 disclosed herein (SEQ ID NOS:28, 29 and/or 30). In one embodiment, the light chain variable region comprises the amino acid sequence shown in SEQ ID NO:31. In another embodiment, the heavy chain variable region comprises the amino acid sequence shown in SEQ ID NO:32.

The disclosure also includes an isolated nucleic acid sequence encoding the light chain variable region comprising the amino acid sequence shown in SEQ ID NO:31, and an isolated nucleic acid sequence encoding the heavy chain variable region comprising the amino acid sequence shown in SEQ ID NO:32.

The disclosure further provides an antibody or antibody fragment comprising at least one light chain complementarity determining region as shown in SEQ ID NOs:25-27 and/or at least one heavy chain complementarity determining region as shown in SEQ ID NOs:28-30.

In one embodiment, the antibody or antibody fragment comprises the light chain CDR sequences of SEQ ID NOS: 25, 26 and 27 and/or the heavy chain CDR sequences of SEQ ID NOS:28, 29 and 30. In another embodiment, the antibody or antibody fragment comprises the amino acid of SEQ ID NO: 31 (light chain variable region) and/or the amino acid of SEQ ID NO:32 (heavy chain variable region).

The inventor has obtained the amino acid sequences of the variable regions of V3-3D2. Accordingly, the disclosure provides isolated light chain complementarity determining region 1 (CDR1) comprising the amino acid sequence QDISNY (SEQ ID NO:33); isolated light chain complementarity determining region 2 (CDR2) comprising the amino acid sequence ATS (SEQ ID NO:34); isolated light chain complementarity determining region 3 (CDR3) comprising the amino acid sequence QQYSRYPPT (SEQ ID NO:35); isolated heavy chain CDR1 comprising the amino acid sequence GVIFNAYA (SEQ ID NO:36); isolated heavy chain CDR2 comprising the amino acid sequence ITGVFHTA (SEQ ID NO:37); and isolated heavy chain CDR3 comprising the amino acid sequence ARGPKYYHSYMDV (SEQ ID NO:38).

The disclosure also includes isolated nucleic acid sequences encoding the light chain complementarity determining region 1 (CDR1) comprising the amino acid sequence QDISNY (SEQ ID NO:33); the light chain complementarity determining region 2 (CDR2) comprising the amino acid sequence ATS (SEQ ID NO:34); the light chain complementarity determining region 3 (CDR3) comprising the amino acid sequence QQYSRYPPT (SEQ ID NO:35); the heavy chain CDR1 comprising the amino acid sequence GVIFNAYA (SEQ ID NO:36); the heavy chain CDR2 comprising the amino acid sequence ITGVFHTA (SEQ ID NO:37); and the heavy chain CDR3 comprising the amino acid sequence ARGPKYYHSYMDV (SEQ ID NO:38).

Also provided are isolated light chain variable regions comprising light chain CDR1, CDR2 and/or CDR3 disclosed herein (SEQ ID NOS:33, 34 and/or 35), and isolated heavy chain variable regions comprising heavy chain CDR1, CDR2 and/or CDR3 disclosed herein (SEQ ID NOS:36, 37 and/or 38). In one embodiment, the light chain variable region comprises the amino acid sequence shown in SEQ ID NO:39. In another embodiment, the heavy chain variable region comprises the amino acid sequence shown in SEQ ID NO:40.

The disclosure also includes an isolated nucleic acid sequence encoding the light chain variable region comprising the amino acid sequence shown in SEQ ID NO:39, and an isolated nucleic acid sequence encoding the heavy chain variable region comprising the amino acid sequence shown in SEQ ID NO:40.

The disclosure further provides an antibody or antibody fragment comprising at least one light chain complementarity determining region as shown in SEQ ID NOs:33-35 and/or at least one heavy chain complementarity determining region as shown in SEQ ID NOs:36-38.

In one embodiment, the antibody or antibody fragment comprises the light chain CDR sequences of SEQ ID NOS: 33, 34 and 35 and/or the heavy chain CDR sequences of SEQ ID NOS:36, 37 and 38. In another embodiment, the antibody or antibody fragment comprises the amino acid of SEQ ID NO:39 (light chain variable region) and/or the amino acid of SEQ ID NO:40 (heavy chain variable region).

The inventor has obtained the amino acid sequences of the variable regions of V3-1G10. Accordingly, the disclosure provides isolated light chain complementarity determining region 1 (CDR1) comprising the amino acid sequence QSVGTN (SEQ ID NO:41); isolated light chain complementarity determining region 2 (CDR2) comprising the amino acid sequence GAS (SEQ ID NO:42); isolated light chain complementarity determining region 3 (CDR3) comprising the amino acid sequence QHYNNWPPYT (SEQ ID NO:43); isolated heavy chain CDR1 comprising the amino acid sequence GVTFNHYT (SEQ ID NO:44); isolated heavy chain CDR2 comprising the amino acid sequence IIPLFGTA (SEQ ID NO:45); and isolated heavy chain CDR3 comprising the amino acid sequence ARSGTTKTRYNWFDP (SEQ ID NO:46).

The disclosure also includes isolated nucleic acid sequences encoding the light chain complementarity determining region 1 (CDR1) comprising the amino acid sequence QSVGTN (SEQ ID NO:41); the light chain complementarity determining region 2 (CDR2) comprising the amino acid sequence GAS (SEQ ID NO:42); the light chain complementarity determining region 3 (CDR3) comprising the amino acid sequence QHYNNWPPYT (SEQ ID NO:43); the heavy chain CDR1 comprising the amino acid sequence GVTFNHYT (SEQ ID NO:44); the heavy chain CDR2 comprising the amino acid sequence IIPLFGTA (SEQ ID NO:45); and the heavy chain CDR3 comprising the amino acid sequence ARSGTTKTRYNWFDP (SEQ ID NO:46).

Also provided are isolated light chain variable regions comprising light chain CDR1, CDR2 and/or CDR3 disclosed herein (SEQ ID NOS:41, 42 and/or 43), and isolated heavy chain variable regions comprising heavy chain CDR1, CDR2 and/or CDR3 disclosed herein (SEQ ID NOS:44, 45 and/or 46). In one embodiment, the light chain variable region comprises the amino acid sequence shown in SEQ ID NO:47. In another embodiment, the heavy chain variable region comprises the amino acid sequence shown in SEQ ID NO:48.

The disclosure also includes an isolated nucleic acid sequence encoding the light chain variable region comprising the amino acid sequence shown in SEQ ID NO:47, and an isolated nucleic acid sequence encoding the heavy chain variable region comprising the amino acid sequence shown in SEQ ID NO:48.

The disclosure further provides an antibody or antibody fragment comprising at least one light chain complementarity determining region as shown in SEQ ID NOs:41-43 and/or at least one heavy chain complementarity determining region as shown in SEQ ID NOs:44-46.

In one embodiment, the antibody or antibody fragment comprises the light chain CDR sequences of SEQ ID NOS: 41, 42 and 43 and/or the heavy chain CDR sequences of SEQ ID NOS:44, 45 and 46. In another embodiment, the antibody or antibody fragment comprises the amino acid of SEQ ID NO:47 (light chain variable region) and/or the amino acid of SEQ ID NO:48 (heavy chain variable region).

The inventor has obtained the amino acid sequences of the variable regions of 15-24. Accordingly, the disclosure provides isolated light chain complementarity determining region 1 (CDR1) comprising the amino acid sequence QSLSSGH (SEQ ID NO:49); isolated light chain complementarity determining region 2 (CDR2) comprising the amino acid sequence GAS (SEQ ID NO:50); isolated light chain complementarity determining region 3 (CDR3) comprising the amino acid sequence QQYAVFLYT (SEQ ID NO:51); isolated heavy chain CDR1 comprising the amino acid sequence GGTFSRYT (SEQ ID NO:52); isolated heavy chain CDR2 comprising the amino acid sequence FIPLLGMT (SEQ ID NO:53); and isolated heavy chain CDR3 comprising the amino acid sequence ARHDSSGYHPLDY (SEQ ID NO:54).

The disclosure also includes isolated nucleic acid sequences encoding the light chain complementarity determining region 1 (CDR1) comprising the amino acid sequence QSLSSGH (SEQ ID NO:49); the light chain complementarity determining region 2 (CDR2) comprising the amino acid sequence GAS (SEQ ID NO:50); the light chain complementarity determining region 3 (CDR3) comprising the amino acid sequence QQYAVFLYT (SEQ ID NO:51); the heavy chain CDR1 comprising the amino acid sequence GGTFSRYT (SEQ ID NO:52); the heavy chain CDR2 comprising the amino acid sequence FIPLLGMT (SEQ ID NO:53); and the heavy chain CDR3 comprising the amino acid sequence ARHDSSGYHPLDY (SEQ ID NO:54).

Also provided are isolated light chain variable regions comprising light chain CDR1, CDR2 and/or CDR3 disclosed herein (SEQ ID NOS:49, 50 and/or 51), and isolated heavy chain variable regions comprising heavy chain CDR1, CDR2 and/or CDR3 disclosed herein (SEQ ID NOS:52, 53 and/or 54). In one embodiment, the light chain variable region comprises the amino acid sequence shown in SEQ ID NO:55. In another embodiment, the heavy chain variable region comprises the amino acid sequence shown in SEQ ID NO:56.

The disclosure also includes an isolated nucleic acid sequence encoding the light chain variable region comprising the amino acid sequence shown in SEQ ID NO:55, and an isolated nucleic acid sequence encoding the heavy chain variable region comprising the amino acid sequence shown in SEQ ID NO:56.

The disclosure further provides an antibody or antibody fragment comprising at least one light chain complementarity determining region as shown in SEQ ID NOs:49-51 and/or at least one heavy chain complementarity determining region as shown in SEQ ID NOs:52-54.

In one embodiment, the antibody or antibody fragment comprises the light chain CDR sequences of SEQ ID NOS: 49, 50 and 51 and/or the heavy chain CDR sequences of SEQ ID NOS:52, 53 and 54. In another embodiment, the antibody or antibody fragment comprises the amino acid of SEQ ID NO:55 (light chain variable region) and/or the amino acid of SEQ ID NO:56 (heavy chain variable region).

The inventor has obtained the amino acid sequences of the variable regions of I4-128. Accordingly, the disclosure provides isolated light chain complementarity determining region 1 (CDR1) comprising the amino acid sequence QTISTY (SEQ ID NO:57); isolated light chain complementarity determining region 2 (CDR2) comprising the amino acid sequence MAS (SEQ ID NO:58); isolated light chain complementarity determining region 3 (CDR3) comprising the amino acid sequence QHYNTYSST (SEQ ID NO:59); isolated heavy chain CDR1 comprising the amino acid sequence GGTFSTYG (SEQ ID NO:60); isolated heavy chain CDR2 comprising the amino acid sequence IIPIFGTA (SEQ ID NO:61); and isolated heavy chain CDR3 comprising the amino acid sequence ARPNTYGYILPVY (SEQ ID NO:62).

The disclosure also includes isolated nucleic acid sequences encoding the light chain complementarity determining region 1 (CDR1) comprising the amino acid sequence QTISTY (SEQ ID NO:57); the light chain complementarity determining region 2 (CDR2) comprising the amino acid sequence MAS (SEQ ID NO:58); the light chain complementarity determining region 3 (CDR3) comprising the amino acid sequence QHYNTYSST (SEQ ID NO:59); the heavy chain CDR1 comprising the amino acid sequence GGTFSTYG (SEQ ID NO:60); the heavy chain CDR2 comprising the amino acid sequence IIPIFGTA (SEQ ID NO:61); and the heavy chain CDR3 comprising the amino acid sequence ARPNTYGYILPVY (SEQ ID NO:62).

Also provided are isolated light chain variable regions comprising light chain CDR1, CDR2 and/or CDR3 disclosed herein (SEQ ID NOS:57, 58 and/or 59), and isolated heavy chain variable regions comprising heavy chain CDR1, CDR2 and/or CDR3 disclosed herein (SEQ ID NOS:60, 61 and/or 62). In one embodiment, the light chain variable region comprises the amino acid sequence shown in SEQ ID NO:63. In another embodiment, the heavy chain variable region comprises the amino acid sequence shown in SEQ ID NO:64.

The disclosure also includes an isolated nucleic acid sequence encoding the light chain variable region comprising the amino acid sequence shown in SEQ ID NO:63, and an isolated nucleic acid sequence encoding the heavy chain variable region comprising the amino acid sequence shown in SEQ ID NO:64.

The disclosure further provides an antibody or antibody fragment comprising at least one light chain complementarity determining region as shown in SEQ ID NOs:57-59 and/or at least one heavy chain complementarity determining region as shown in SEQ ID NOs:60-62.

In one embodiment, the antibody or antibody fragment comprises the light chain CDR sequences of SEQ ID NOS: 57, 58 and 59 and/or the heavy chain CDR sequences of SEQ ID NOS:60, 61 and 62. In another embodiment, the antibody or antibody fragment comprises the amino acid of SEQ ID NO:63 (light chain variable region) and/or the amino acid of SEQ ID NO:64 (heavy chain variable region).

The inventor has obtained the amino acid sequences of the variable regions of V4-17. Accordingly, the disclosure provides isolated light chain complementarity determining region 1 (CDR1) comprising the amino acid sequence SSNIGTYY (SEQ ID NO:65); isolated light chain complementarity determining region 2 (CDR2) comprising the amino acid sequence DNN (SEQ ID NO:66); isolated light chain complementarity determining region 3 (CDR3) comprising the amino acid sequence AAWDDSLSGVV (SEQ ID NO:67); isolated heavy chain CDR1 comprising the amino acid sequence GGSITRNSYF (SEQ ID NO:68); isolated heavy chain CDR2 comprising the amino acid sequence MYYDGTT (SEQ ID NO:69); and isolated heavy chain CDR3 comprising the amino acid sequence ARHHVTELRVLEWLPKSDY (SEQ ID NO:70).

The disclosure also includes isolated nucleic acid sequences encoding the light chain complementarity determining region 1 (CDR1) comprising the amino acid sequence SSNIGTYY (SEQ ID NO:65); the light chain complementarity determining region 2 (CDR2) comprising the amino acid sequence DNN (SEQ ID NO:66); the light chain complementarity determining region 3 (CDR3) comprising the amino acid sequence AAWDDSLSGVV (SEQ ID NO:67); the heavy chain CDR1 comprising the amino acid sequence GGSITRNSYF (SEQ ID NO:68); the heavy chain CDR2 comprising the amino acid sequence MYYDGTT (SEQ ID NO:69); and the heavy chain CDR3 comprising the amino acid sequence ARHHVTELRVLEWLPKSDY (SEQ ID NO:70).

Also provided are isolated light chain variable regions comprising light chain CDR1, CDR2 and/or CDR3 disclosed herein (SEQ ID NOS:65, 66 and/or 67), and isolated heavy chain variable regions comprising heavy chain CDR1, CDR2 and/or CDR3 disclosed herein (SEQ ID NOS:68, 69 and/or 70). In one embodiment, the light chain variable region comprises the amino acid sequence shown in SEQ ID NO:71. In another embodiment, the heavy chain variable region comprises the amino acid sequence shown in SEQ ID NO:72.

The disclosure also includes an isolated nucleic acid sequence encoding the light chain variable region comprising the amino acid sequence shown in SEQ ID NO:71, and an isolated nucleic acid sequence encoding the heavy chain variable region comprising the amino acid sequence shown in SEQ ID NO:72.

The disclosure further provides an antibody or antibody fragment comprising at least one light chain complementarity determining region as shown in SEQ ID NOs:65-67 and/or at least one heavy chain complementarity determining region as shown in SEQ ID NOs:68-70.

In one embodiment, the antibody or antibody fragment comprises the light chain CDR sequences of SEQ ID NOS: 65, 66 and 67 and/or the heavy chain CDR sequences of SEQ ID NOS:68, 69 and 70. In another embodiment, the antibody or antibody fragment comprises the amino acid of SEQ ID NO:71 (light chain variable region) and/or the amino acid of SEQ ID NO:72 (heavy chain variable region).

The inventor has obtained the amino acid sequences of the variable regions of V3-2C3. Accordingly, the disclosure provides isolated light chain complementarity determining region 1 (CDR1) comprising the amino acid sequence QSISSW (SEQ ID NO:73); isolated light chain complementarity determining region 2 (CDR2) comprising the amino acid sequence KAS (SEQ ID NO:74); isolated light chain complementarity determining region 3 (CDR3) comprising the amino acid sequence QHYNSYSQT (SEQ ID NO:75); isolated heavy chain CDR1 comprising the amino acid sequence GGTFNNYA (SEQ ID NO:76); isolated heavy chain CDR2 comprising the amino acid sequence IIPIFGTA (SEQ ID NO:77); and isolated heavy chain CDR3 comprising the amino acid sequence ARVCSFYGSGSYYNVFCY (SEQ ID NO:78).

The disclosure also includes isolated nucleic acid sequences encoding the light chain complementarity determining region 1 (CDR1) comprising the amino acid sequence QSISSW (SEQ ID NO:73); the light chain complementarity determining region 2 (CDR2) comprising the amino acid sequence KAS (SEQ ID NO:74); the light chain complementarity determining region 3 (CDR3) comprising the amino acid sequence QHYNSYSQT (SEQ ID NO:75); the heavy chain CDR1 comprising the amino acid sequence GGTFNNYA (SEQ ID NO:76); the heavy chain CDR2 comprising the amino acid sequence IIPIFGTA (SEQ ID NO:77); and the heavy chain CDR3 comprising the amino acid sequence ARVCSFYGSGSYYNVFCY (SEQ ID NO:78).

Also provided are isolated light chain variable regions comprising light chain CDR1, CDR2 and/or CDR3 disclosed herein (SEQ ID NOS:73, 74 and/or 75), and isolated heavy chain variable regions comprising heavy chain CDR1, CDR2 and/or CDR3 disclosed herein (SEQ ID NOS:76, 77 and/or 78). In one embodiment, the light chain variable region comprises the amino acid sequence shown in SEQ ID NO:79. In another embodiment, the heavy chain variable region comprises the amino acid sequence shown in SEQ ID NO:80.

The disclosure also includes an isolated nucleic acid sequence encoding the light chain variable region comprising the amino acid sequence shown in SEQ ID NO:79, and an isolated nucleic acid sequence encoding the heavy chain variable region comprising the amino acid sequence shown in SEQ ID NO:80.

The disclosure further provides an antibody or antibody fragment comprising at least one light chain complementarity determining region as shown in SEQ ID NOs:73-75 and/or at least one heavy chain complementarity determining region as shown in SEQ ID NOs:76-78.

In one embodiment, the antibody or antibody fragment comprises the light chain CDR sequences of SEQ ID NOS: 73, 74 and 75 and/or the heavy chain CDR sequences of SEQ ID NOS:76, 77 and 78. In another embodiment, the antibody or antibody fragment comprises the amino acid of SEQ ID NO:79 (light chain variable region) and/or the amino acid of SEQ ID NO:80 (heavy chain variable region).

The disclosure also provides variants of the CDR sequences, light chain and heavy chain variable sequences and antibodies comprising said variant sequences. Such variants include proteins that perform substantially the same function as the specific proteins or fragments disclosed herein in substantially the same way. For example, a functional variant of a CDR or light chain or heavy chain variable region or antibody will be able to bind to an antigen or epitope recognized by the native CDR or light chain or heavy chain variable region or antibody.

In one embodiment, the variant amino acid sequences of the light chain CDR1, CDR2 and CDR3, and the heavy chain CDR1, CDR2 and CDR3 have at least 50%, at least 60%, at least 70%, at least 80%, at least 90%, or at least 95% sequence identity to the CDR sequences disclosed herein.

In another embodiment, the variant amino acid sequences of the light chain variable region and the heavy chain variable region have at least 50%, at least 60%, at least 70%, at least 80%, at least 90% or at least 95% sequence identity to the light chain variable region and heavy chain variable region sequences disclosed herein.

The term "sequence identity" as used herein refers to the percentage of sequence identity between two polypeptide sequences or two nucleic acid sequences. To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions.times.100%). In one embodiment, the two sequences are the same length. The determination of percent identity between two sequences can also be accomplished using a mathematical algorithm. An optional, non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules of the present disclosure. BLAST protein searches can be performed with the XBLAST program parameters set, e.g., to score—50, wordlength=3 to obtain amino acid sequences homologous to a protein molecule of the present disclosure. To obtain gapped alignments for comparison purposes, Gapped BLAST can be utilized as described in Altschul et al., 1997, Nucleic Acids Res. 25:3389-3402. Alternatively, PSI-BLAST can be used to perform an iterated search, which detects distant relationships between molecules (Id.). When utilizing BLAST, Gapped BLAST, and PSI-Blast programs, the default parameters of the respective programs (e.g., of XBLAST and NBLAST) can be used (see, e.g., the NCBI website). Another optional, non-limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

The disclosure also provides isolated nucleic acid sequences encoding variants of the CDR sequences and variable region sequences discussed above.

The term "nucleic acid sequence" as used herein refers to a sequence of nucleoside or nucleotide monomers consisting of naturally occurring bases, sugars and intersugar (backbone) linkages. The term also includes modified or substituted sequences comprising non-naturally occurring monomers or portions thereof. The nucleic acid sequences of the present disclosure may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine.

The term "isolated nucleic acid sequences" as used herein refers to a nucleic acid substantially free of cellular material or culture medium when produced by recombinant DNA techniques, or chemical precursors, or other chemicals when chemically synthesized. An isolated nucleic acid is also substantially free of sequences, which naturally flank the nucleic acid (i.e. sequences located at the 5' and 3' ends of the nucleic acid) from which the nucleic acid is derived. The term "nucleic acid" is intended to include DNA and RNA and can be either double stranded or single stranded, and represents the sense or antisense strand. Further, the term "nucleic acid" includes the complementary nucleic acid sequences.

The term "amino acid" includes all of the naturally occurring amino acids as well as modified amino acids.

The term "isolated polypeptides" refers to a polypeptide substantially free of cellular material or culture medium when produced by recombinant DNA techniques, or chemical precursors or other chemicals when chemically synthesized.

Variant nucleic acid sequences include nucleic acid sequences that hybridize to the nucleic acid sequences encoding the amino acid sequences disclosed herein under at least moderately stringent hybridization conditions, or have at least 50%, 60%, 70%, 80%, 90% or 95% sequence identity to the nucleic acid sequences that encode the amino acid sequences disclosed herein.

The term "variant" as used herein includes modifications or chemical equivalents of the amino acid and nucleic acid sequences disclosed herein that perform substantially the same function as the polypeptides or nucleic acid molecules disclosed herein in substantially the same way. For example, variants of polypeptides disclosed herein include, without limitation, conservative amino acid substitutions. Variants of polypeptides also include additions and deletions to the polypeptide sequences disclosed herein. In addition, variant sequences include analogs and derivatives thereof.

The term "antibody" as used herein is intended to include monoclonal antibodies, polyclonal antibodies, and chimeric antibodies. The antibody may be from recombinant sources and/or produced in transgenic animals. The term "antibody fragment" as used herein is intended to include without limitations Fab, Fab', F(ab')2, scFv, dsFv, ds-scFv, dimers, minibodies, diabodies, and multimers thereof, multispecific antibody fragments and Domain Antibodies. Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, dsFv, ds-scFv, dimers, minibodies, diabodies, bispecific antibody fragments and other fragments can also be synthesized by recombinant techniques.

The antibody or antibody fragments described herein also include functional variants of the sequences so that the antibody or antibody fragment can bind to the HA protein.

In certain embodiments, the antibody or antibody fragment comprises all or a portion of a heavy chain constant region, such as an IgG1, IgG2, IgG3, IgG4, IgA1, IgA2, IgE, IgM or IgD constant region. In one embodiment, the heavy chain constant region is an IgG1 heavy chain constant region. Furthermore, the antibody or antibody fragment can comprise all or a portion of a kappa light chain constant region or a lambda light chain constant region. In one embodiment, the light chain constant region is a kappa light chain constant region.

As described herein, to produce human monoclonal antibodies, antibody producing cells (lymphocytes) can be harvested from a human infected with influenza and then used to make monoclonal antibodies. For example they can be fused with myeloma cells by standard somatic cell fusion procedures thus immortalizing these cells and yielding hybridoma cells. Such techniques are well known in the art, (e.g. the hybridoma technique originally developed by Kohler and Milstein (*Nature* 256:495-497 (1975)) as well as other techniques such as the human B-cell hybridoma technique (Kozbor et al., *Immunol. Today* 4:72 (1983)), the EBV-hybridoma technique to produce human monoclonal antibodies (Cole et al., *Methods Enzymol,* 121:140-67 (1986)), and screening of combinatorial antibody libraries (Huse et al., *Science* 246:1275 (1989)). Alternatively methods that copy the genes encoding the antibodies produced by individual B cells for example the selected lymphocyte antibody method (Babcook et al 1996) may be used. These methods can be used to screen for monoclonal antibodies that specifically react with hemagglutinin.

Specific antibodies, or antibody fragments, reactive against hemagglutinin antigen or the stem region thereof may also be generated by screening expression libraries encoding immunoglobulin genes, or portions thereof, expressed in bacteria with cell surface components. For example, complete Fab fragments, VH regions and FV regions can be expressed in bacteria using phage expression libraries (See for example Ward et al., *Nature* 341:544-546 (1989); Huse et al., *Science* 246:1275-1281 (1989); and McCafferty et al., *Nature* 348:552-554 (1990)).

The term "light chain complementarity determining region" as used herein refers to regions of hypervariability within the light chain variable region of an antibody molecule. Light chain variable regions have three complementarity determining regions termed light chain complementarity determining region 1, light chain complementarity determining region 2 and light chain complementarity determining region 3 from the amino terminus to the carboxy terminus.

The term "light chain variable region" as used herein refers to the variable region of a light chain.

The term "heavy chain complementarity determining region" as used herein refers to regions of hypervariability within the heavy chain variable region of an antibody molecule. The heavy chain variable region has three complementarity determining regions termed heavy chain complementarity determining region 1, heavy chain complementarity determining region 2 and heavy chain complementarity determining region 3 from the amino terminus to carboxy terminus.

The term "heavy chain variable region" as used herein refers to the variable region of a heavy chain.

The disclosure also provides compositions comprising the CDRs in an appropriate framework, variable regions and/or antibodies disclosed herein with a pharmaceutically acceptable excipient, carrier, buffer or stabilizer.

Further provided herein are methods and uses of the CDRs in an appropriate framework, variable regions and/or antibodies or antibody fragments thereof disclosed herein for protecting against infection with influenza or treating an infection with influenza in a subject. In one embodiment, the disclosure provides a method for protecting against infection with influenza or treating an infection with influenza in a subject comprising administration of the CDRs in an appropriate framework, variable regions and/or antibodies or antibody fragments described herein to a subject. Also provided is use of the CDRs in an appropriate framework, variable regions and/or antibodies or antibody fragments described herein for protecting against infection with influenza or treating an infection with influenza in a subject. Further provided is use of the CDRs in an appropriate framework, variable regions and/or antibodies or antibody fragments described herein for preparing a medicament for protecting against infection with influenza or treating an infection with influenza in a subject. Even further provided are the CDRs in an appropriate framework, variable regions and/or antibodies or antibody fragments described herein for use in protecting against infection with influenza or treating an infection with influenza in a subject.

The above disclosure generally describes the present disclosure. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Figure 2:
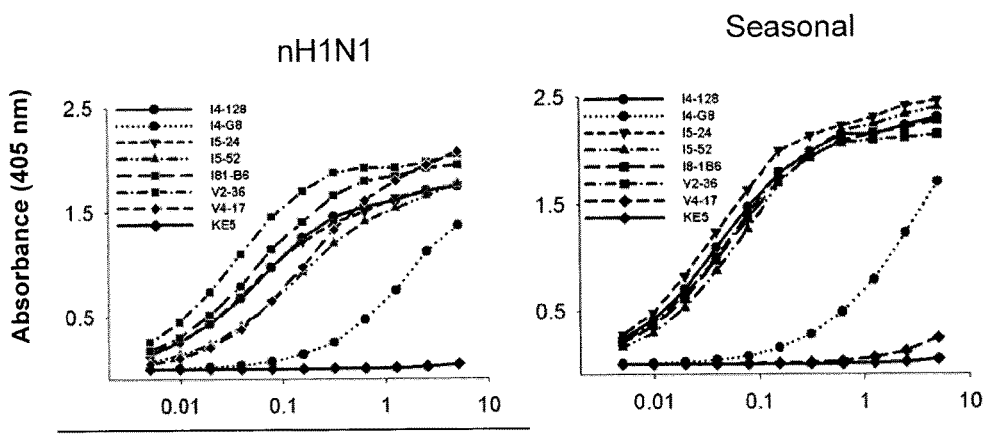
FIG. 2 shows diverse cross-reactive/heterosubtypic anti-HA antibodies are induced by infection or vaccination with nH1N1 and react with conventional vaccines at the HA head or stem and with HA from highly pathogenic avian H5N1 influenza A virus. A, Reactivity with nH1N1 or seasonal influenza vaccine and with purified recombinant ectodomain of H5 HA (A/Vietnam/1203/2004, Clade1). ELISA titrations of selected mAbs on plates coated with the nH1N1 vaccine or the 2009/2010 seasonal influenza vaccine or with purified recombinant H5 HA (A/Vietnam/1203/2004, Clade1). B, IGHV-gene usage in the 48 anti-snH1 HA mAbs. The 95% confidence intervals of IGHV1-69 usage were 38-66%. *8 of 9 mAbs using IGHV4-39 were from a single subject, V2. C, Some cross-reactive/heterosubtypic antibodies bind to the HA stem others to the HA head. Above panel:—competition ELISA of selected mAbs on nH1N1 vaccine showing inhibition of binding of C179, which recognizes an epitope on the HA stem. Circles: I5-24 (open); I4-128 (filled). Triangles: I8-1B6 (upright, open), I5-52 (inverted, filled). Squares: V4-17 (filled); Control mAb, KE5 against HCMV (open). Below panel:—treatment of nH1N1-coated ELISA plates at pH 5 for 1 h prior to mAb incubation causes inhibition of binding by IGHV1-69-encoded mAbs. D, IGHV1-69-using mAbs V3-2G6, I5-24, V3-1G10 and I8-1B6 fail to inhibit hemagglutination by nH1N1 but the IGHV4-39-using mAb V2-36 does and V4-12 does too. The indicated mAbs (40 µg/mL) were titrated and a value of zero means that hemagglutination was not inhibited at a titre of <2 or 20 µg/mL. E,F Cross-reactivity of selected mAbs with the HA of influenza A/Hong Kong/156/197 (H5N1). Indirect immunofluorescence was used to assess the binding of mAbs to H5 HA expressed by adenovirus infection in the A549 human epithelial cell-line using a Cellomics instrument. E, Shows instrument-image of cells stained with either secondary antibodies alone or 5 µg/mL of mAb I4-128. F, Shows the percentage of cells stained with varying concentrations of the indicated mAbs or titres of plasma from an nH1N1-vaccinated subject (V2) or an nH1N1-infected subject (I14). Shown is the average of duplicate measurements from a representative experiment of three.
Figure 2:
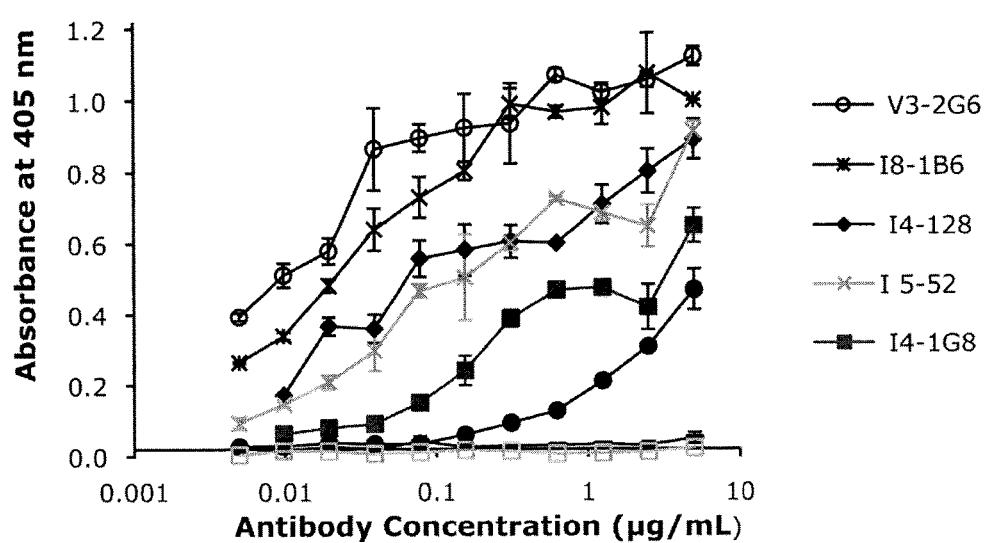
Figure 2:
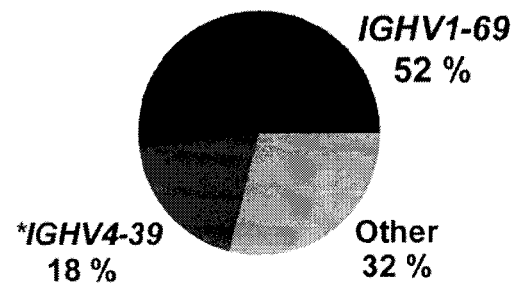
Figure 2:
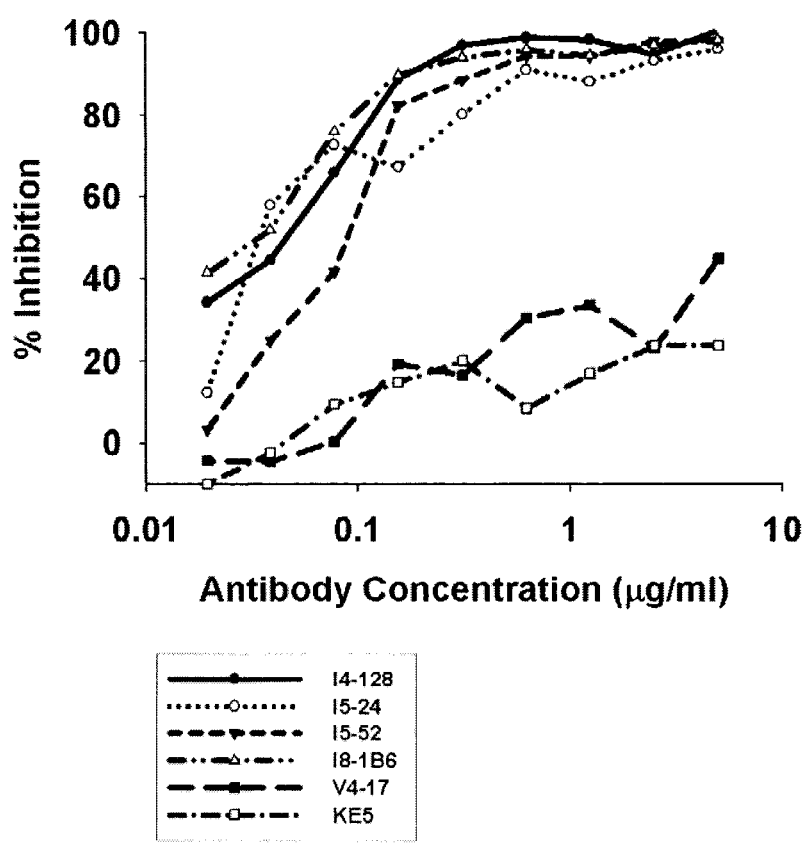
Figure 2:
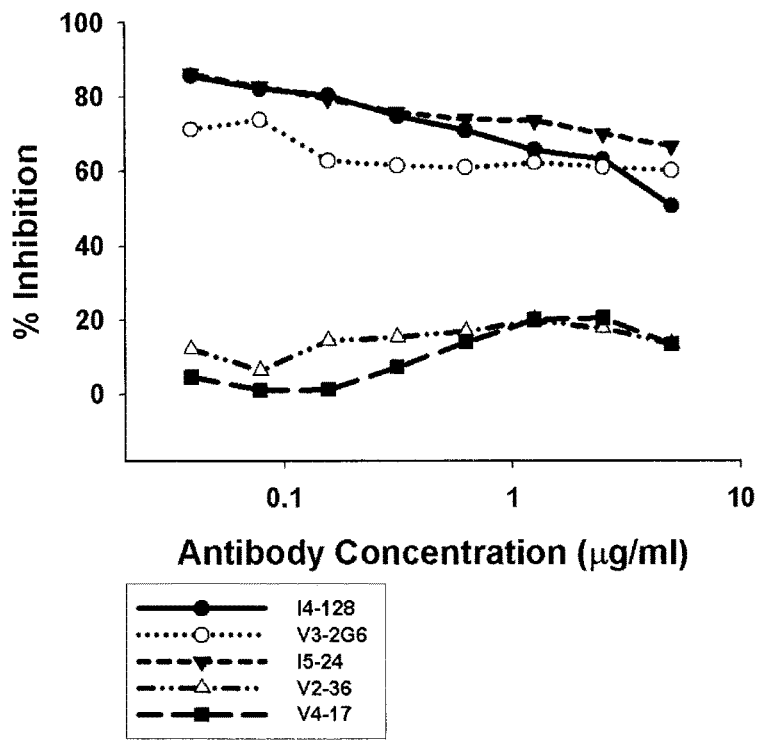
Figure 2:
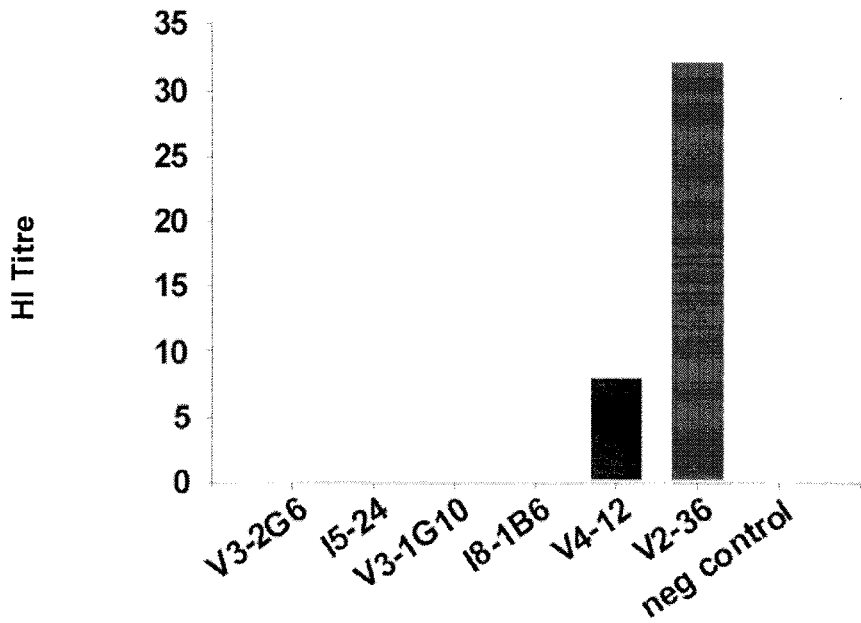

Three approaches were used to generate human monoclonal antibodies (mAbs) that reacted with HA of the soluble ectodomain of the nH1N1 influenza virus (snH1 HA) (FIG. 1). First, antibodies were randomly cloned from newly generated plasmablasts (PB) circulating in the blood of recently infected patients. This approach was based upon observations that ~7 days after vaccination, PB that secrete antibodies specific for the vaccine appear in the blood (Barington et al. 1990; Heilmann et al. 1987) and form a significant fraction of the total PB (Odendahl et al. 2005; Wrammert et al. 2008), and upon techniques that the present inventor had previously used to obtain monoclonal antibodies from blood-borne PB by RT-PCR and cloning and expression of the DNA encoding the antigen-binding site (Babcook et al. 1996). In the absence of data on the kinetics of entry of infection-specific PB into the blood during infections, blood was collected from subjects with laboratory-confirmed nH1N1 infections ~7 days after the onset of symptoms, and fluorescence-activated cell-sorting (FACS) was used to purify individual PB. From these, 8 mAbs were cloned and expressed as IgG1 molecules (Babcook et al. 1996; McLean et al. 2005), finding 4 that bound to a recombinant soluble form of the trimeric ectodomain of the nH1N1 HA (snH1 HA), (Table 1a, and the example of mAb I4-128 in FIG. 2). Strikingly, given the novel or unique antigenic nature of the nH1 HA, all 4 of these antibodies also bound to the current seasonal influenza vaccine (Table 1a, and example of mAb I4-128 in FIG. 2A). In the second approach, using similar blood samples, individual PB expressing antibodies were FACS-purified by using fluorochrome-labelled snH1 HA by exploiting the fact that newly generated PB express their immunoglobulin on their surface (Odendahl et al. 2005; Nossal et al. 1972). Five mAbs were generated that bound to snH1 HA and all 3 also bound to the seasonal influenza vaccine. Thus a total of 9 mAbs against snH1 HA were generated from blood-borne PB from 3 patients (Table 1a), demonstrating that, during an infection, at least some newly generated PB enter the blood and do not all remain in lymphoid tissues near the site of infection. Sixteen more mAbs were also generated from snH1 HA-binding PB from subjects vaccinated with the nH1N1 vaccine. Strikingly, of the total of 25 mAbs generated from PB from infected or vaccinated subjects, all but one, V4-17, cross-reacted with the seasonal influenza vaccine and purified recombinant H5 HA and thus were also cross-reactive or heterosubtypic (Table 1a; FIG. 2A). In a third approach, blood samples were collected 2-8 weeks after recovery from infection or vaccination with pandemic 2009 (H1N1) influenza and FACS was used to purify individual snH1 HA-binding, class-switched memory B cells that were then expanded and differentiated to clones of PB as before (McLean et al. 2005). Of the 23 mAbs against snH1 HA generated from the memory B cells in this way, all cross-reacted with seasonal influenza vaccine and purified recombinant H5 HA and were thus heterosubtypic (Table 1B, representative mAbs in FIGS. 2A and 2E, F).

In total, from 5 infected and 3 vaccinated subjects, 48 recombinant mAbs were generated that bound snH1 HA, and all but one cross-reacted with the current seasonal influenza vaccine and purified recombinant H5 HA (Table 1). The high frequency of heterosubtypic mAbs was not due to the fact that recombinant snH1 HA was used to sort out PB or memory B cells, as all 4 of the snH1 HA-binding mAbs generated from the randomly selected PB also bound to the seasonal influenza vaccine and the purified recombinant H5 HA (Table 1A). Moreover, the epitopes bound by the mAbs were present on the inactivated, detergent-disrupted nH1N1 virus as all 48 mAbs also bound to the nH1N1 vaccine and 47 also bound to the 2009/2010 seasonal influenza vaccine and the purified recombinant H5 HA (Table 1; examples in FIGS. 2A and 2E, F).

Strikingly, 52% of the anti-snH1 HA mAbs, derived from infected (44%) or vaccinated subjects (57%), or PB (40%) or memory B cells (65%), used one V-gene, IGHV1-69 (Table 1; FIG. 2B). IGHV1-69 is normally expressed 3.6% to less than 5% of B cells (de Wildt et al, 1999; Sasso et al. 1996). Where multiple mAbs were obtained from the same subject, the response to infection or vaccination with nH1N1 was clonally diverse, although V4 had two mAbs against the HA stem that were derived from the same B cell clonotype. The striking exception was one subject V2 (Table 1) which did not yield a monoclonal antibody using IGHV1-69, discussed below. In subject V3, 12 out of 14 mAbs derived from memory B cells used IGHV1-69, but these were all different with different IGHD and IGHJ genes and used a variety of L-chain V-genes. IGHV1-69 was used preferentially in recombinant single-chain variable fragments (scFv) selected from phage-display libraries of human immunoglobulin genes using the HA of H5N1 avian influenza (Ekiert et al. 2009; Sui et al. 2009; Throsby et al. 2008; Kashyap et al. 2008). IGHV1-69 encodes major features of a binding site for a site on the HA stem that is highly conserved in a variety of influenza subtypes (Ekiert et al. 2009; Sui et al. 2009). This conservation reflects structural constraints on the HA stem, which undergoes a pH-induced, irreversible conformational change when the virus is endocytosed and encounters the low pH in the endosome (~pH5) (Wiley et al. 1987). This conformation of the HA stem mediates fusion of the viral and endosomal membranes enabling the viral genome to enter the cytosol. Binding of these scFv prevented this conformational change in the HA stem and results in neutralization of infectivity of multiple subtypes of influenza (Ekiert et al. 2009; Sui et al. 2009). This raised the prospect that similar antibodies might be induced by a vaccine that would protect against multiple influenza subtypes.

The present data show that antibodies that bind to the HA of multiple strains or subtypes of influenza viruses, including those using IGHV1-69, can be readily made by humans in response to infection or vaccination by the nH1N1 influenza, which is a unique hemagglutinin to most humans, and can dominate the antibody response. In ongoing work on another subject who was vaccinated with non-adjuvanted nH1N1 vaccine, the first mAb from an snH1 HA-binding PB was generated and it was cross-reactive/heterosubtypic and used IGHV1-69.

The majority of the heterosubtypic mAbs bound to the HA stem but others bound to the HA head. To test whether the epitope was on the HA stem versus the head, 3 approaches were used. To test whether the epitope bound by a mAb was on the HA stem two assays were used. One was inhibition of binding to HA of C179, an antibody that was known to bind to a conserved epitope on the HA stem (Okuno et al. 1993). The second assay was whether the epitope targeted by the mAb was affected by treatment at low pH5, which induces an irreversible conformational change in the stem (Wiley et al. 1987). To test whether the epitope was on the HA head, close to the receptor-binding site, it was tested whether the mAbs could inhibit hemagglutination by nH1N1. That mAbs using IGHV1-69 bound to an epitope on the HA stem was confirmed by showing that they inhibited completely binding of C179 to nH1N1 vaccine (FIG. 2C, upper graph). Another heterosubtypic mAb I5-52, which used IGHV1-18, also inhibited C179-binding and thus bound to the HA stem (FIG. 2C). Additionally, low pH-treatment decreased the binding of mAbs using IGHV1-69 selectively as compared with another heterosubtypic mAb V2-36 that used IGHV4-39 (FIG. 2C, lower graph). The IGHV1-69-using mAbs did not inhibit hemagglutination by the nH1N1 virus (FIG. 2D), consistent with these mAbs binding to the stem rather than the HA head. In contrast, V2-36, which used IGHV4-39 and V4-12 inhibited hemagglutination by nH1N1 (FIG. 2D), indicating that they bound to the head of the nH1N1 HA and not the stem. All of these mAbs against the HA stem, both the 52% using IGHV1-69 and 6% using other IGHV-genes all bound to the conventionally produced pandemic H1N1 vaccine and to the 2009/2010 seasonal influenza vaccine (FIG. 2A and Table 1). Thus conventional influenza vaccines exhibited the conserved epitope on the HA stem to which these heterosubtypic anti-HA stem antibodies bound. It was concluded from these data that the conserved epitope on the HA stem was exhibited by the conventionally prepared influenza vaccines as well as the epitopes on the HA head recognized by mAbs that inhibited hemagglutination such as V2-36. This taught against the prevailing view that the conserved epitope on the HA stem was somehow hidden in infectious influenza virus or vaccines (Chen et al, 2009, Corti et al, 2010, Sui et al 2009, Steel et al 2010).

The present inventor obtained 9 mAbs that used IGHV4-39, and all inhibited hemagglutination, suggesting they bound an epitope on the HA head. Eight of them were obtained from one subject, V2, who exhibited an oligoclonal response with 7 belonging to the same clonotype (comprising V2-36, V2-2, V2-3, V2-4, V2-7, V2-11 and V2-38). Another mAb from this donor, V2-12 also used IGHV4-39 but combined it with different IGHD and IGHJ genes and a different L-chain V-gene. IGHV4-39-using mAbs dominated the response in this donor as the only other mAb obtained from this donor used another IGHV gene. Another mAb that used IGHV4-39, V4-17, was obtained from another donor, V4, and bound to the HA head, as it inhibited hemagglutination and failed to inhibit the binding of C179 (FIG. 2C). Although it did not bind to the 2009/2010 seasonal influenza vaccine, as discussed below, the evidence that V4-17 had 19 mutations in IGHV4-39 indicated that the PB was generated by the HA from nH1N1 stimulating a memory B cell that had previously been induced by infection or vaccination with a seasonal influenza H1N1 virus (that differed in that epitope to the H1N1 influenza virus in the 2009/2010 seasonal influenza vaccine). Thus it is likely that V4-17 is also cross-reactive and will have reactivity with a previously encountered seasonal influenza H1N1 virus.

Given that IGHV1-69 using mAbs had been shown to bind to the HA of H5N1 viruses, the ability of some of the mAbs to bind to cells expressing the full-length H5 HA from the highly pathogenic avian influenza A HongKong 156/97 (H5N1) were tested (FIG. 2E,F). IGHV1-69-using mAbs (FIG. 2E, F), as well as other heterosubtypic mAbs using other IGHV genes such as V3-1E8 and I5-52 bound the H5 HA. In contrast, V2-36 and V4-17, which recognize epitopes on the nH1 HA head, bound only weakly to the H5 HA of HongKong 156/97 (H5N1) (FIG. 2F). Significant levels of antibodies that bound to cells expressing H5 HA were also found in convalescent plasma from nH1N1 infected patients and in vaccinated subjects 7 days after vaccination (FIG. 2F). All mAbs, with the sole exception of V4-17 were reactive in ELISA with purified recombinant H5 HA (A/Vietnam/1203/2004, Clade1) (FIG. 2A), Table 1.

Figure 3:
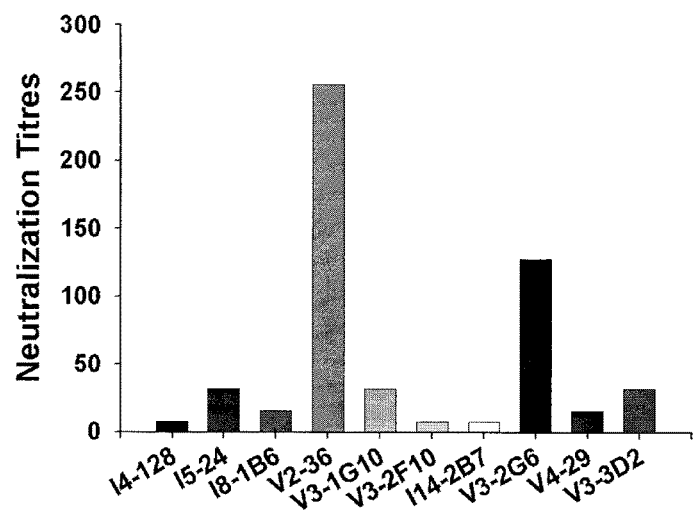
FIG. 3 shows neutralization of multiple subtypes of influenza A viruses by mAbs. A, Neutralization of nH1N1 by the indicated purified mAbs that were present for the entire assay. Titrations commenced at a concentration of 5 µg/mL of each mAb. * indicates titre >256. B, Neutralization of infectivity of highly pathogenic Influenza A/Goose/Ger/R1400/07 (H5N1) avian virus by indicated mAbs and by titrations of plasma from subjects infected (I14) or vaccinated (V2) with nH1N1. Also shown below is a graph of the neutralization of titrations of selected mAbs against highly pathogenic Influenza A/Goose/Ger/R1400/07 (H5N1) avian virus and with below a photograph of the plaques with and without an anti-HA stem mAb I8-1B6 (1 µg/ml). C, Anti-stem mAbs encoded by IGHV1-69 inhibit H5 HA-mediated fusion. Note the decreased syncytia formation in wells treated by the anti-stem mAb, C179, and the IGHV1-69-using mAbs, in comparison to the control with no antibody added (no Ab) and a mAb that binds to the HA head, V2-36, where there are many syncytia.
Figure 3:
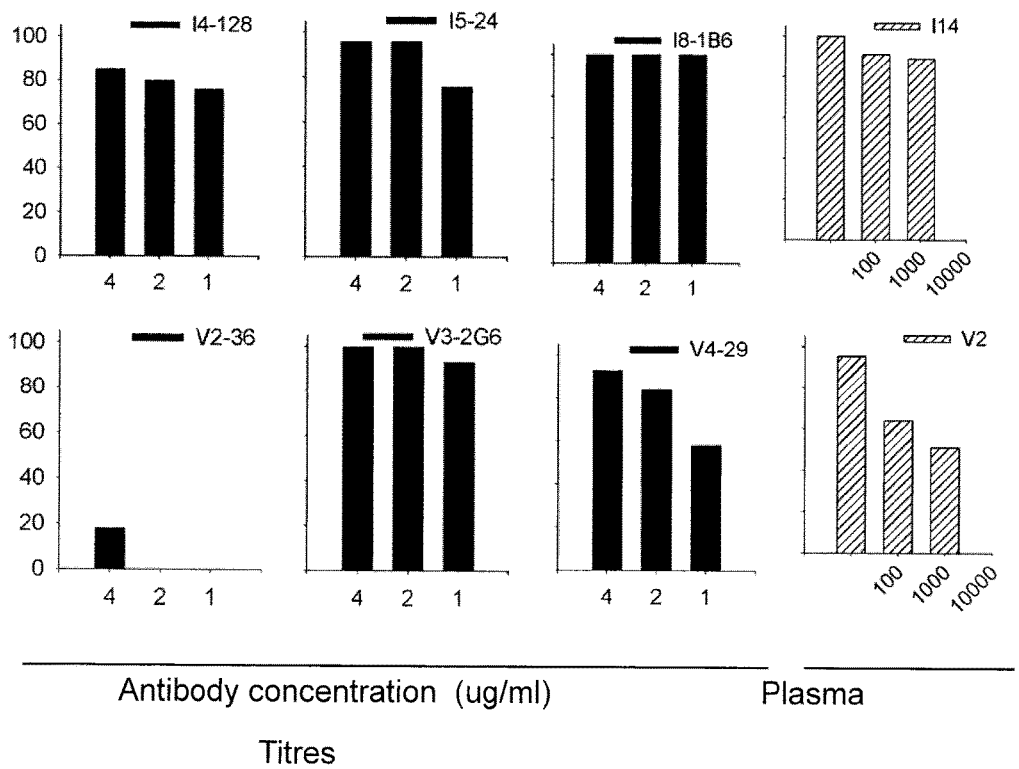

32 of the mAbs were tested for their capacity to neutralize nH1N1 infectivity in the standard WHO microneutralization assay. Only two of the mAbs that were tested (V2-36 and V4-17) neutralized infectivity of nH1N1. Only V2-36 neutralized the seasonal influenza virus A/Brisbane/59/07 (H1N1), consistent with the lack of binding of V4-17 to the seasonal influenza vaccine (FIG. 2A). V2-36 and V4-17 were the only mAbs of the 32 tested that inhibited hemagglutination. It was reasoned that the standard assay was biased to mAbs that bound to epitopes on the HA head because they inhibited viral attachment. Thus in the standard microneutralization assay, mixtures of mAbs and the challenge virus were only in contact with the cells for 2-3 hours, after which they removed. This was because the assay was designed for assessing neutralizing antibodies in human serum and the removal of the serum (but not the purified mAbs) was necessary to allow the TPCK-trypsin included in the medium to activate the virus by cleaving the HA (Klenk et al. 1975). As mAbs that bind to the HA stem will not inhibit viral attachment and are washed away after the 3 hour incubation with the antibody-virus mixture, the assay was modified by leaving the virus and mAbs for the duration of the assay. Under these conditions, which mimic the constant presence of antibodies in an infection in vivo, most of the mAbs that bound to the HA stem exhibited neutralizing activity against the nH1N1 virus (FIG. 3A). All of the 10 IGHV1-69-using mAbs tested in the modified assay completely neutralized nH1N1 at concentrations from 78-2500 ng/ml. Many neutralized seasonal influenza A/Brisbane/59/07(H1N1). V3-1B9 using IGHV3-11, and I14-2B7 using IGHV1-18, also completely neutralized nH1N1 at 625 ng/ml and 1250 ng/ml respectively. However, in this panel of mAbs, the most potent neutralizer was V2-36, which bound to the HA head and inhibited infectivity completely at less than 40 ng/ml. The second was V3-2G6 which neutralized completely at less than 80 ng/ml.

Figure 3B:
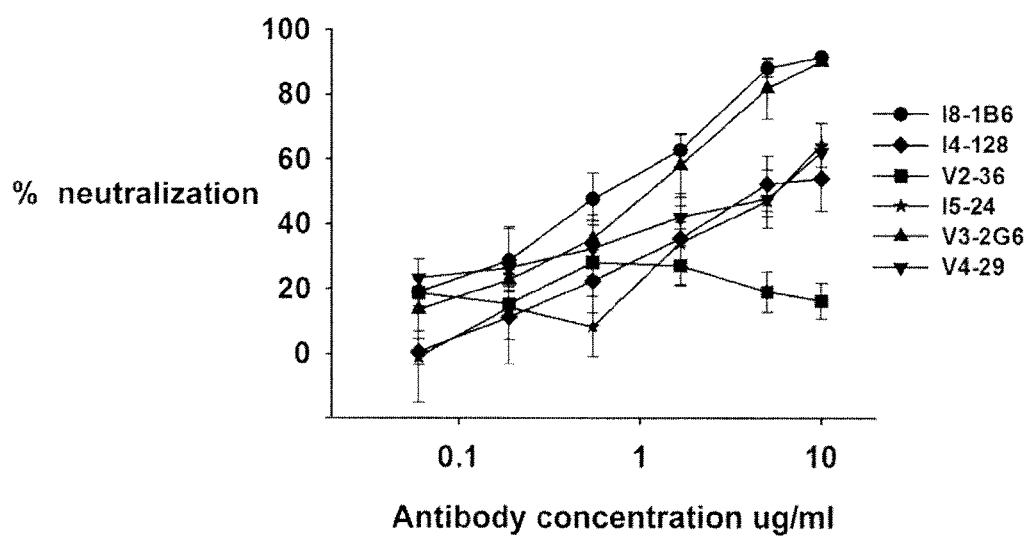
Figure 3B:
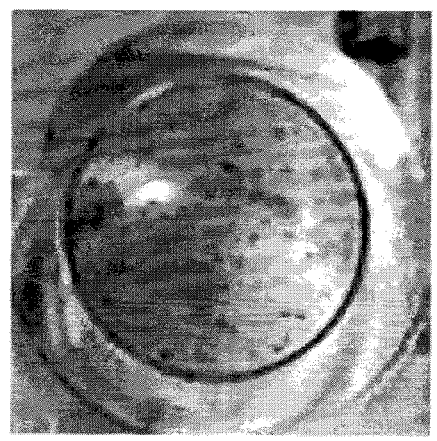
Figure 3B:
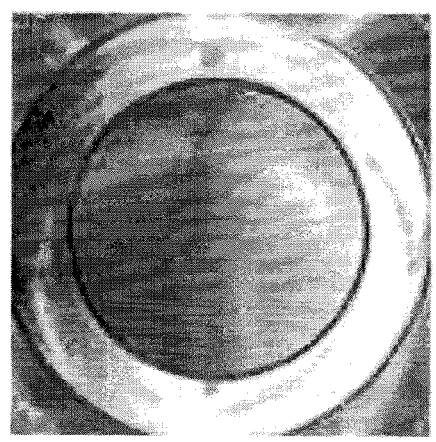
Figure 3:
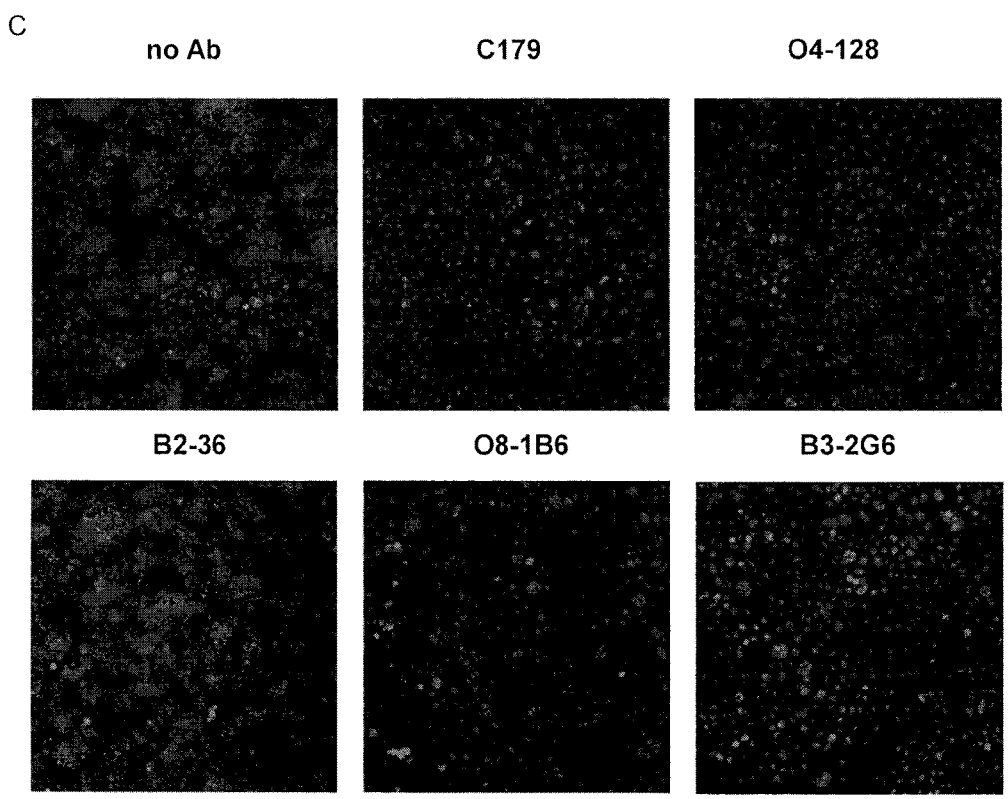
Figure 4:
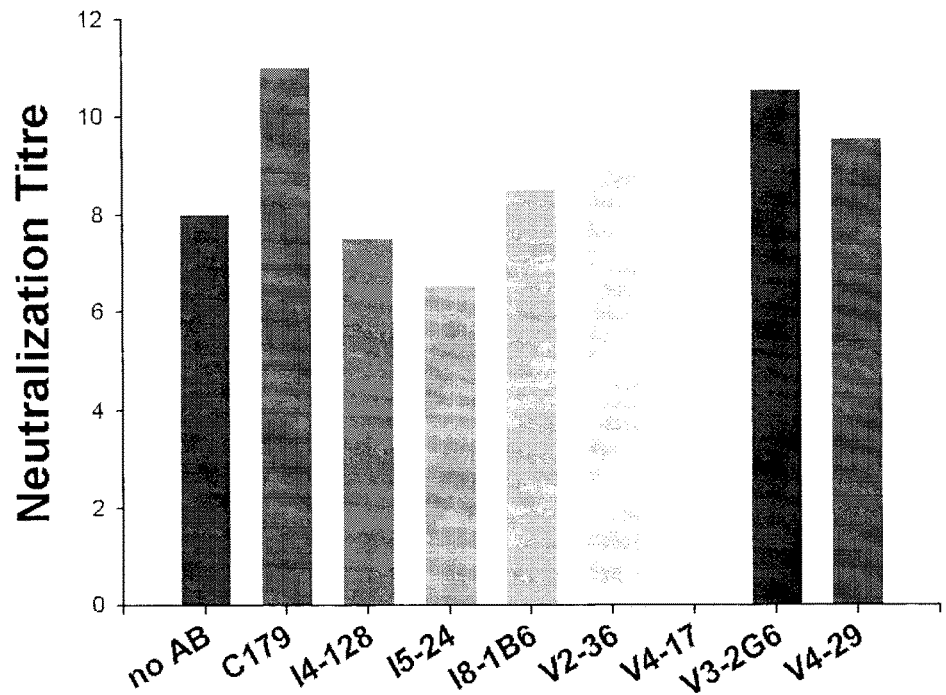
FIG. 4 shows IGHV1-69 encoded monoclonal antibodies do not neutralize plaque formation by A/Ck/Ger/R28/03 (H7N7) influenza A viruses at 4 µg/mL.

The ability of selected mAbs to neutralize the infectivity of the highly pathogenic avian influenza virus A/Goose/Ger/R1400/07 (H5N1) were tested and a good correlation was seen between H5 HA-binding (FIG. 2F) and neutralization of H5N1 infectivity (FIG. 3B), with V2-36 failing to neutralize H5N1 infectivity. As expected (Sui et al. 2009; Throsby et al. 2008), these IGHV1-69-using mAbs did not neutralize infectivity of an H7N7 virus (FIG. 4). Moreover, plasma from subjects infected (I14) or vaccinated (V2) with nH1N1 also neutralized H5N1 infectivity (FIG. 3B). These mAbs inhibited cell-cell fusion mediated by cell-surface expression of full-length HA from influenza A/Hong Kong/156/97 (H5N1) (Sui et al. 2009) (FIG. 3C). Thus it was concluded that humans infected or vaccinated with nH1N1 make cross-protective antibodies that can bind to the HA of different virus subtypes and can neutralize pandemic nH1N1, seasonal H1N1, and highly pathogenic H5N1 avian influenza viruses.

Did the nH1 HA induce the production of these heterosubtypic mAbs by activating a naïve B cell or a memory B cell generated in a previous encounter with influenza viruses? Especially in the case of the mAbs generated from PB collected ~7-10 days after infection or vaccination (e.g. I5-24, V4-29), a large number of somatic mutations would suggest that the nH1 HA cross-activated a pre-existing memory B cell. In fact, an unprecedented 52% of the mAbs generated from PB had IGHV genes with more than 28 mutations, meaning that more than 10% of their nucleotides were mutated. The median number of mutations in mAbs from PB was 29. This compares with the average mutation rate of human germinal centre or memory B cells of 13.6+/−4.8 (Wrammert et al. 2008). Overall, the anti-snH1 HA mAbs from PB had a significantly higher frequency of mutations in IGHV gene than those from memory B cells (median number of mutations of 15.5) (FIG. 5A) and none of the memory B cells had more than 10% of the nucleotides in IGHV mutated. This is consistent with evidence that murine PB make higher affinity antibodies than do memory B cells (Smith et al. 1997). Based on the present findings it was predicted that high-affinity memory B cells do not circulate in the blood until after retained antigen has been cleared from lymph-nodes because this antigen will activate them to PB.

It is likely that those cross-reactive or heterosubtypic antibodies that had accumulated a lot of somatic mutations in the IGHV gene had been generated by activation by the HA of nH1N1 of memory B cells that had been induced by previous contact with seasonal influenza viruses. This notion is supported by a paper showing that vaccination with seasonal influenza expanded in some subjects a small population of memory B cells making heterosubtypic antibodies that used IGHV1-69 (Corti et al. 2010). However, in contrast to the response to a unique HA, as in the infection or vaccination with nH1N1 disclosed herein, the heterosubtypic response reported in Corti et al (2010) was weak and only seen in some individuals. Indeed as commented by Corti et al, their observations raise the question of the effectiveness of heterosubtypic antibodies induced by influenza vaccinations as "even in high-responder individuals, heterosubtypic antibodies hardly reach effective neutralizing concentrations in the serum". Consistent with the induction of low levels of heterosubtypic antibodies by seasonal influenza, a low percentage of European sera (Garcia et al. 2009) or pooled human gamma globulin preparations contain low levels of antibodies against the H5N1 HA (Lynch et al 2009). Human mAbs generated before the 2009 pandemic that bind to the HA stem can neutralize nH1N1 (Burioni et al 2010) and vaccination with seasonal influenza induces increases in neutralizing titres against H5N1 (Gioia et al. 2008), and the numbers of memory B cells making antibodies that bind H5 HA (Corti et al. 2010). Moreover in one subject that was vaccinated with nH1N1, before vaccination there were existing levels of antibodies binding to H5 HA-expressing cells that had increased by 7 days after vaccination (FIG. 5B). A minority of the mAbs that exhibited small numbers of somatic mutations, were probably ultimately derived from naïve B cells that were activated by nH1N1, whether directly generated from PB (I4-112, I5-52, or I4-128 with 5, 11 or 13 mutations) or memory B cells (e.g. I4-1G8, I14-B7, V3-3B3, V3-2C3, or V3-2C2 with 3, 5, 6, 6 and 9 mutations). These mAbs suggest, without wishing to be bound by any theory, that the initial primary response to an unfamiliar antigenically distinct unique influenza hemagglutinin is cross-reactive or heterosubtypic. Given that the memory response to seasonal influenza is dominated by a limited number of clonotypes of subtype-specific antibodies (Wrammert et al. 2008), with subsequent encounters with slightly mutated hemagglutinins ("antigenic drift") these initial cross-reactive or heterosubtypic memory B cells are rapidly outcompeted by higher affinity strain-specific memory B cells generated by affinity maturation.

Figure 6:
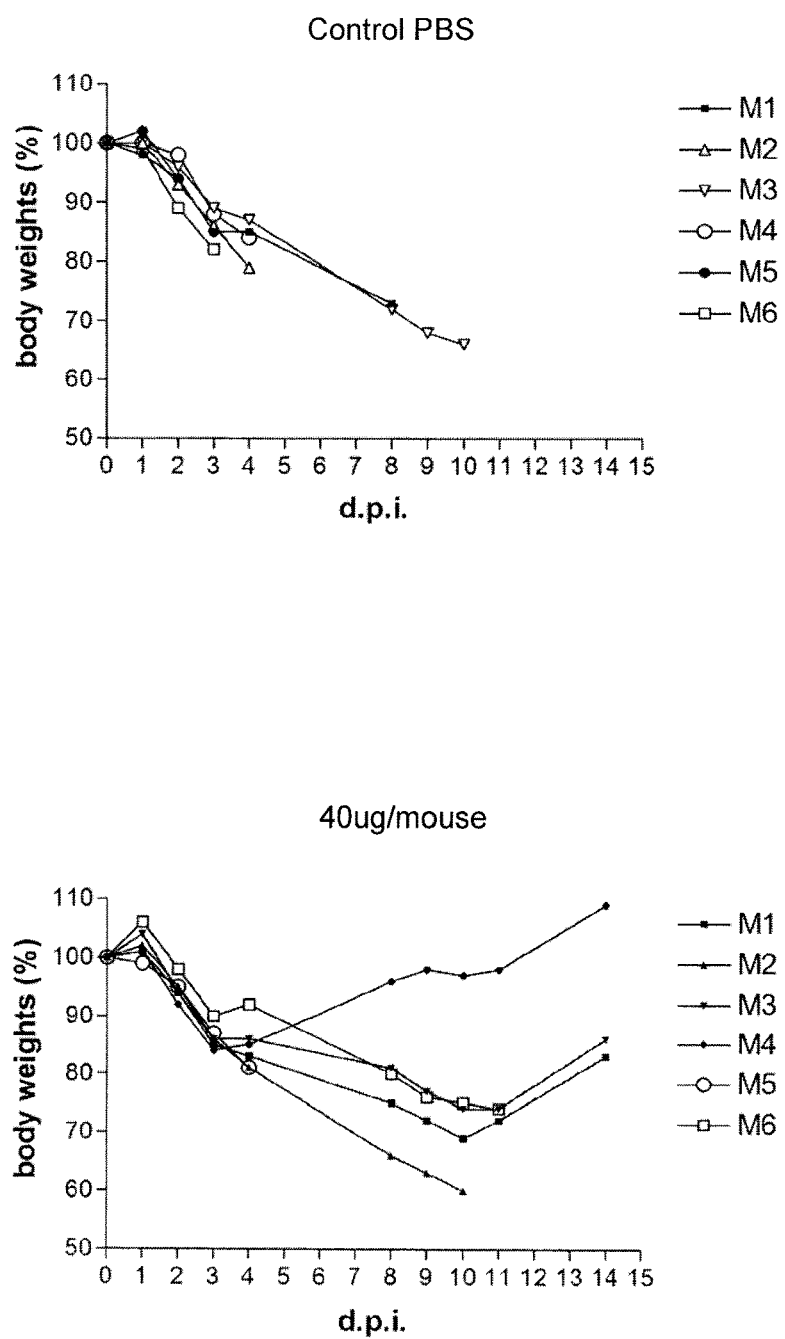
FIG. 6 shows results of treatment of CD-1 mice infected intranasally with a lethal dose ($2 \times 10^5$ plaque-forming units) of the 2009 novel H1N1 influenza A virus (nH1N1) with the indicated doses of the human monoclonal antibody V2-36 expressed as IgG1. The mice were injected once intraperitoneally with the mAb 24 hours after infection intranasally with the pandemic nH1N1 virus. Control mice were injected with diluent alone (phosphate-buffered saline, PBS). The mice were weighed daily.
Figure 6:
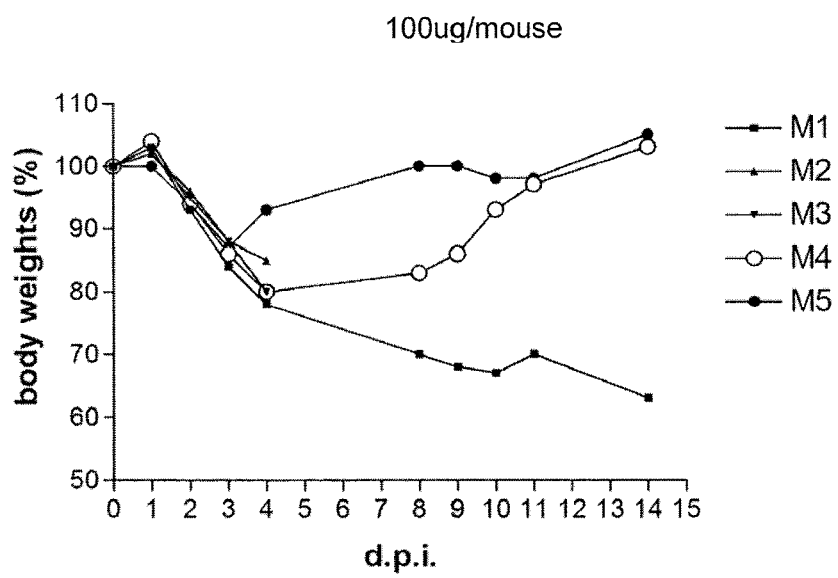
Figure 6:
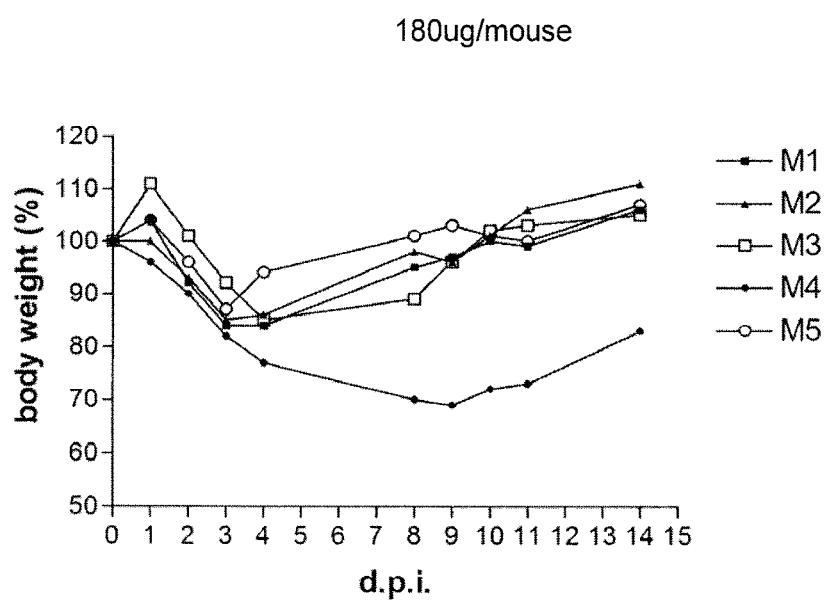
Figure 6:
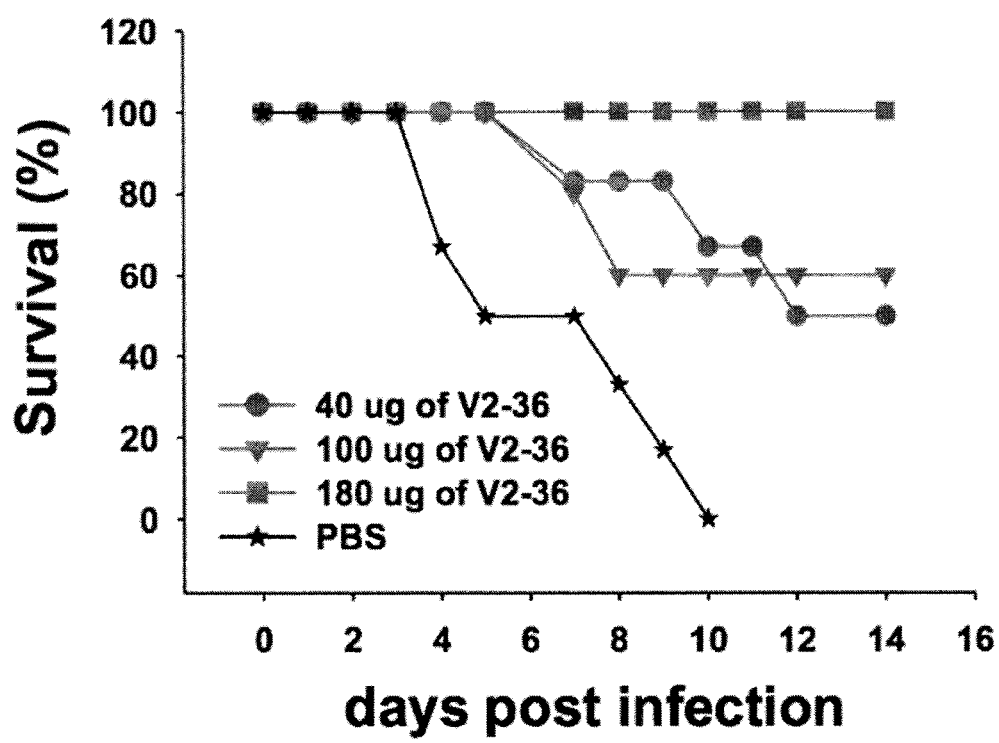
Figure 7:
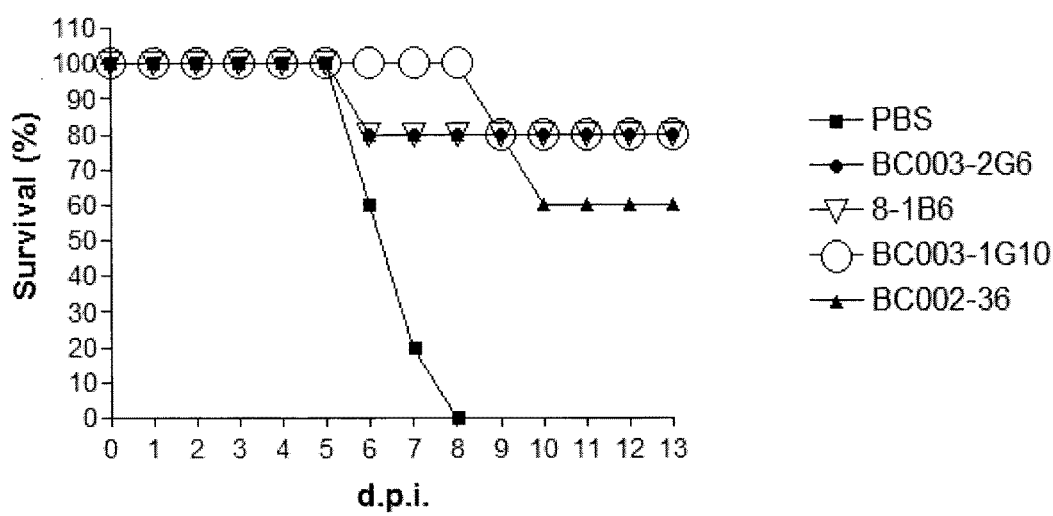
FIG. 7 shows results of treatment of groups of 5 CD-1 mice infected intranasally with a lethal dose ($2 \times 10^5$ plaque-forming units) of the 2009 novel H1N1 influenza A virus with the indicated human monoclonal antibodies expressed as IgG1 molecules. With the exception of V2-36 (labeled in the FIG. 7 as BC002-36, later named V2-36 as it was generated from a subject vaccinated with the pandemic H1N1 vaccine) which was given as a dose of 200 µg intraperitoneally 48 hours after infection, all mAbs were given at a dose of 300 µg intraperitoneally 24 hours after infection. The mAbs labelled in the FIG. 7 as BC003-2G6 and BC003-1G10, were later named V3-2G6 and V3-1G10 as they were generated from a subject vaccinated with the pandemic H1N1 vaccine and 8-1B6, 4-128 and 5-24 were later named I8-1B6, I4-128 and I5-24, as they were all generated from subjects infected with the pandemic H1N1 influenza virus. The mixture of 100 µg of V2-36 and 150 µg of I5-24 was given 24 hours after infection. Controls were injected with vehicle alone (PBS). Results are shown per treated group of 5 as survival rate or in terms of average weight. Shown is the result of one experiment, for clarity split into two panels.
Figure 7:
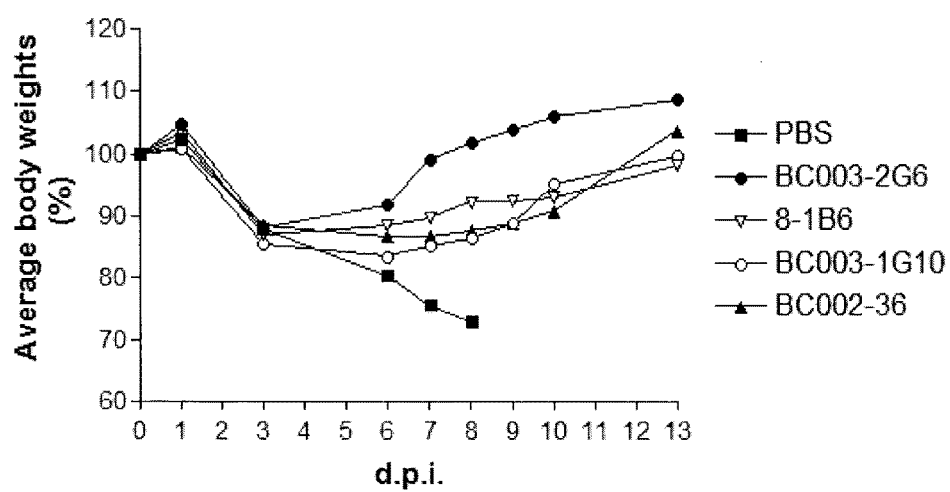
Figure 7:
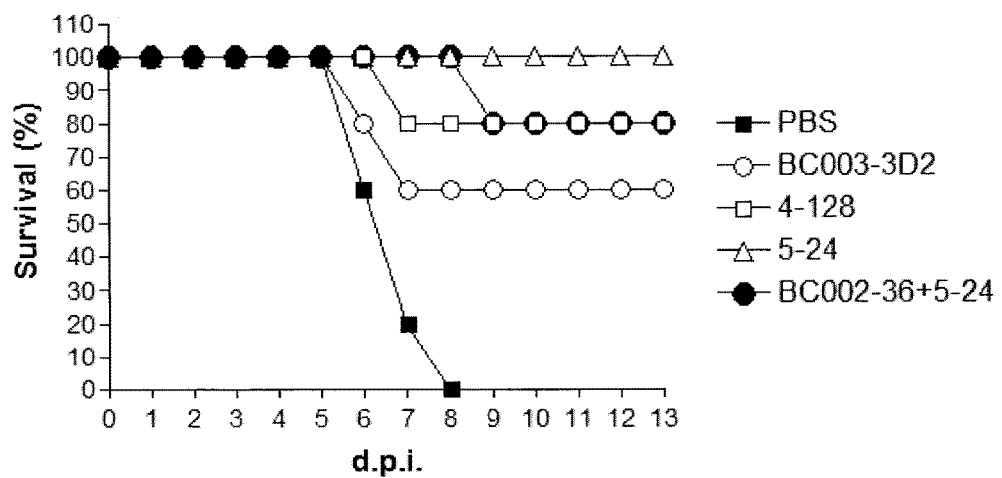
Figure 7:
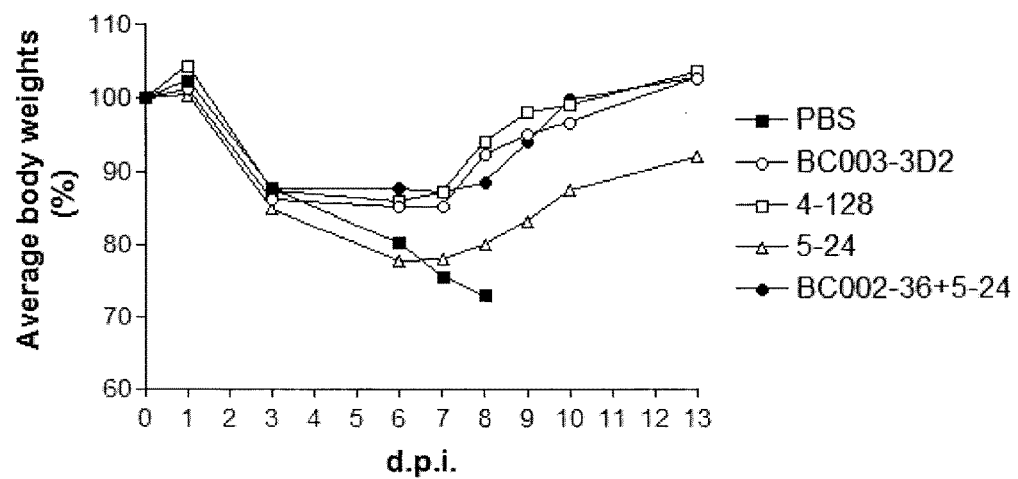

The present inventor tested the therapeutic potential of these mAbs in treating serious infections with nH1N1 in mice given a lethal dose of a human isolate of nH1N1 virus. The mAb V2-36 was given 24 hours after infection of the mice. Whereas 5/5 mice in the control group treated with only saline died, all 5 of the mice treated with a single injection of 180 µg (~6 mg/kg) of V2-36 24 hours after infection of the mice, survived (FIG. 6). A single dose of 200 µg of V2-36 given 48 hours after infection still had a therapeutic effect (FIG. 7). Also shown in FIG. 7 are the therapeutic effects on mice with a lethal influenza infection with 300 µg of V3-2G6, I5-24, I4-128, V3-3D2, V3-1G10 and I8-1B6 and a mixture of V2-36 and I5-24.

To test whether a heterosubtypic mAb against the HA stem generated from a vaccinated subject, V3-2G6, had therapeutic effects on a lethal infection with avian H5N1 influenza, groups of mice were infected with a heterologous H5N1 influenza virus and given a single intraperitoneal injection of 150 µg or 300 µg of V3-2G6 24 hours after intra-nasal infection (FIG. 8A). A $3^{rd}$ and $4^{th}$ group of mice that were treated with V3-2G6 were given single doses of 300 µg or 600 µg 48 hours after infection (FIG. 8A). There was 100% survival in all treatment groups, although the mice treated 48 hrs later were seriously ill, as evidenced by their loss of weight. To test the minimum dose that was necessary for a cross-protective therapeutic effect on lethal H5N1 influenza infections, groups of mice were infected with a heterologous H5N1 influenza virus and given a single intraperitoneal injection of 150 µg or 75 µg or 37.5 µg of V3-2G6 24 hours after intra-nasal infection (FIG. 8B). As can be seen 37.5 µg of V3-2G6 only cured 80% of mice from a lethal infection with H5N1 influenza virus, but the mice treated with 75 ug, although they all survived had a larger weight loss compared with the group treated with 150 µg.

To test whether a heterosubtypic mAb against the HA stem generated from a vaccinated subject, V3-2G6, protected mice from a lethal dose of a heterologous H5N1 influenza virus, groups of mice were treated with graded doses of V3-2G6 and 24 hours later the mice were infected intranasally. V3-2G6 was very potent. Both doses, 15 µg and 5 µg (250 µg/Kg and 750 µg/Kg) protected against death from infection with H5N1, and 750 µg/Kg protected from any weight loss (FIG. 9).

It was next asked whether the dominant cross-protective antibody response in memory B cells induced by vaccination with the pdmH1N1 vaccine correlated with circulating cross-protective antibodies in human plasma. The ability of plasma from donor V3 taken 14 days and one year after vaccination to protect mice against a lethal infection was tested with H5N1 influenza (FIG. 10). As a control, plasma from a young adult donor taken in 2006 was used, to ensure the subject could not have been in contact with the 2009 pandemic H1N1 virus. It was observed that 400 µl of plasma from V3 taken 14 days after vaccination completely protected the mice from a lethal infection with H5N1 influenza. 400 µl of plasma collected a year after the vaccination protected against death but there was a small weight loss with H5N1 infection. However three times the dose of human plasma protected the mice against significant weight loss (FIG. 10). These data showed that, even a year after vaccination, human plasma conferred protection on mice subsequently infected with the H5N1 influenza virus.

Why should cross-protective antibodies dominate the response to HA of a pandemic influenza but not to seasonal influenza (Corti et al 2010)? In the response to a pandemic influenza virus, the only memory B cells that bind the HA with sufficient affinity to differentiate them to a PB or induce them to undergo somatic mutation in a germinal centre, will be those making heterosubtypic antibodies that bind to conserved structural features among viral subtypes. Notably, helper T cells are activated by epitopes shared between viral subtypes (Doherty and Kelso, 2008) and B cells that have been activated by binding HA or viruses will compete to present these epitopes to the T cells (Allen et al. 2007). In this regard, the memory B cells activated by conserved epitopes on the nH1 HA will have multiple competitive advantages over the naïve B cells that recognize the novel or unique strain-specific features on the head of the pandemic HA. Not only are the heterosubtypic memory B cells more numerous, they possess intrinsic advantages, including increased signalling and expression of proteins that co-activate T cells (Tangye et al. 2009). Thus in the response to pandemic influenza, heterosubtypic antibodies will dominate. In contrast, with seasonal influenza, large numbers of memory B cells against strain-specific epitopes on the HA head are activated by low-affinity interactions with the HA of "drifted" seasonal strains and enter germinal centres to undergo affinity maturation (Paus et al. 2006). There they out-compete the less numerous heterosubtypic memory B cells for T-cell help, explaining the rarity and limited level of the heterosubtypic antibody responses to the HA of seasonal influenza (Corti et al. 2010; Garcia et al. 2009).

In only one of the subjects, (V2), from whom 9 mAbs were generated that bound to snH1 HA, did the present inventor fail to find a mAb using IGHV1-69. Clearly B cells from V2 did express IGVH1-69 as other antibodies were cloned using IGVH1-69 in V2. To obtain insight into the mechanism of the dominant anti-HA stem antibody response to the pdmH1N1, the exceptional subject, V2, was analysed in more detail. If a frequency of anti-HA stem mAbs using IGHV1-69 in responses to pdmH1N1 was assumed to be 50%, the probability of obtaining the observed result from V2 by chance alone was 0.002 and thus unlikely (Table 3). Similarities were noted in the antibody response of V2 to the nH1N1 vaccine to that of the typical human antibody response to the seasonal influenza vaccine. Thus 8 of 9 mAbs from V2 blocked hemagglutination and were directed against the HA head and 7 belonged to the same clonotype (Table 1). Moreover these mAbs had many mutations and reacted with seasonal influenza vaccine, indicating they were derived from memory B cells that had been cross-activated by the HA of nH1N1 vaccine. Thus, in V2, the lack of a dominant response of antibodies using IGHV1-69 to the nH1N1 vaccine correlated with an antibody response against the HA head, like that which occurs in seasonal influenza (Wrammert et al, 2008).

In this subject, V2, aged 63, cross-reactive memory B cells using IGHV4-39, were likely elicited by a virus related to nH1N1 (Hancock et al. 2009). Consistent with the notion that cross-reactive antibodies against the HA head of seasonal influenza use IGHV4-39, a heterosubtypic antibody that cross-reacted with the head of some seasonal influenza H1N1 and H5N1 viruses and that also used IGHV4-39, was recently isolated from a subject vaccinated with the seasonal influenza vaccine (Corti et al. 2010). These activated memory B cells against the HA head, as in seasonal influenza, would have physically outcompeted (Schwickert et al, 2011) for T cell help (Allen et al, 2007, Victora et al 2010, Schwickert et al 2011) those rare memory B cells against the HA stem. V2 was over 60 years in age and clearly by his dominant, cross-reactive antibody response to the HA head, with many somatic mutations (Table 1), had been in contact with a related virus, as supported by Hancock et al (2009). In contrast, in other subjects infected or vaccinated with pdmH1N1, who saw the HA head of nH1N1 as unique, there was a paucity of memory B cells activated by the HA head of nH1N1. In them, those rare memory B cells against the HA stem that had endocytosed HA of nH1N1 or nH1N1 virions (Russell et al, 1979), could present T-cell epitopes shared between viral subtypes (Doherty et al, 2008) to memory helper T cells, unimpeded by competition from memory B cells against the HA head (Allen et al, 2007, Victora, et al 2010, Schwickert et al 2011). Even if a few memory B cells had low affinity for the HA of nH1N1, they would not compete for T cell help with memory B cells making higher-affinity antibodies against the HA stem (Victora et al 2010, Schwickert et al 2011). Moreover, memory B cells against the HA stem would have multiple competitive advantages over the naïve B cells (Tangye et al 2009). Therefore antibodies against the HA stem will dominate the antibody response to a novel HA. Moreover, it is unlikely that that the intrinsic nature of the pdmH1N1 antigen or its presentation to the immune system (Wei et al, 2010b) was a factor in the dominance of the anti-HA stem antibody response to pdmH1N1, as this occurred in our studies with subjects with both infections and vaccinations with nH1N1, which involve many differences in the presentation and nature of the antigen, the site of the immune response, and the associated inflammatory responses.

Discussion

The present findings have implications for the rapid preparation of therapeutic agents for emerging pandemics and for the prospect of a broad-spectrum influenza vaccine. In August 2009, only months after the nH1N1 outbreak had started, the present inventor obtained the first therapeutic mAb against nH1N1 (I4-128). Furthermore, in principle, there are no technical or regulatory reasons that therapeutic monoclonal antibodies generated in humans against pandemic influenza virus or other emerging pathogens should not be rapidly developed and deployed.

The conventionally prepared nH1N1 vaccine as well as the seasonal influenza vaccine clearly exhibited the conserved epitope recognized by mAbs against the HA stem, including those mAbs that use IGHV1-69 (FIG. 2A). The anti-HA stem mAbs bound as readily to the conventionally prepared vaccines as did the mAbs that bound to the head and inhibited hemagglutination like V2-36 (FIG. 2A). The nH1N1 vaccine was administered with the AS03 adjuvant system. However, two mAbs were generated against HA of nH1N1 from a subject vaccinated with unadjuvanted nH1N1 vaccine and one of the mAbs used IGHV1-69. Thus it is likely that unadjuvanted nH1N1 vaccine induces a high frequency of anti-HA stem antibodies. Human vaccination with the nH1N1 vaccine, comprising a unique influenza HA to most humans induced circulating heterosubtypic antibodies that, when transferred to mice, protected against a lethal infection with heterologous H5N1 influenza virus (FIG. 10). The present observation of a dominant heterosubtypic antibody response to vaccination with a conventionally prepared pandemic nH1N1 influenza supports a novel, vaccination strategy that deliberately avoids inducing antibodies against the HA head that normally protect against influenza infections. For example, the first vaccination could be with an inactivated influenza virus (or its HA) that has an antigenically unique HA head to that subject, such as that of the pandemic nH1N1. After an interval, this could be followed by vaccination with an inactivated influenza virus (or the HA) that shares a conserved epitope on the HA stem but has another antigenically unique HA head, such as that of a influenza virus circulating in another species like avian influenza H5N1 virus or an artificially mutated HA. By avoiding the cross-activation of memory B cells making antibodies with low or high affinity binding to epitopes on the HA head that will otherwise outcompete the rare heterosubtypic memory B cells making antibodies against the conserved HA stem, this strategy ensures a robust cross-protective heterosubtypic antibody response. This is achieved based on these results with pandemic nH1N1 vaccine, using conventional vaccines based on HA from influenza viruses that have not circulated in humans. One example is the existing approved vaccine for avian influenza H5N1 virus. Boosting should be done with yet another unique HA head, for example the avian H7 HA in the group 2 of subtypes of HA, in order to extend the range of broadly protective antibodies to Group 2 influenza viruses. Thus the presently disclosed method of sequential vaccination with unique hemagglutinins enables the induction of broadly protective heterosubtypic antibodies against other conserved sites on influenza viruses, such as on the stem of the H3 HA (Wang et al. 2010) and also other pathogens.

Recently, Wrammert et al (2011), reported very similar results of monoclonal antibodies (mAbs) generated from humans infected with pandemic H1N1 influenza. Thus 5 of the 15 mAbs against HA (30%) generated from 3 out of 4 people infected with pandemic H1N1 influenza were against the HA-stem and neutralized a broad range of H1N1 influenza viruses. Moreover Wrammert et al. (2011) observed that 4 of the monoclonal antibodies (two of which were a clonal pair) from 2 subjects used IGHV1-69. They found that a total of 11 out of 15 monoclonal antibodies against the hemagglutinin of nH1N1 neutralized the pandemic H1N1 influenza, of which 5 were against the hemagglutinin stem. Only two antibodies specifically neutralized the pandemic H1N1 and did not neutralize seasonal H1N1 influenza viruses. Thus 82% of the 15 monoclonal antibodies that neutralized pandemic influenza also neutralized various seasonal H1N1 influenza viruses. Wrammert et al (2011) also found that there were a high number of somatic mutations in the IGHV gene of the monoclonal antibodies and concluded, most antibodies against the pandemic influenza were cross-reactive and were generated from memory B cells induced by seasonal influenza viruses or vaccines and said if this "is true it will be important to characterize the efficacy of the pandemic H1N1 vaccine to induce a similarly cross-protective response." The news of their findings provoked widespread public and scientific interest in its novel implications for the prospect of a "universal influenza vaccine". Thus Settembre et al. (2011) concluded "It now appears that sequential infection by virus strains that share a conserved neutralizing epitope on a background of significant antigenic change may promote the production of antibodies against that conserved epitope. Such sequential exposures should promote greater breadth of immunity". Recently there has been a report of the isolation of a human monoclonal antibody from a human vaccinated with the seasonal influenza vaccine that cross-protected against most Group 2 hemagglutinin subtype viruses, including H3N2 and H7N7 viruses (Ekiert et al, 2011). This further supports that there are conserved sites on the hemagglutinin stem in Group 2 viruses (Wang et al, 2010) and is further evidence that our invention of vaccination with successive immunizations of "unfamiliar", unique hemagglutinins from Group 2, like avian influenza viruses from Group 2, can result in circulating cross-protective antibodies against Group 2 viruses.

Additionally, the present results show that the standard microneutralization tests and the hemagglutination inhibition assay are inadequate to monitor the degree of protection in serum induced by this vaccination strategy.

To conclude, the present inventor has demonstrated that humans can respond to infection or vaccination with an influenza with a unique hemagglutinin by generating PB and memory B cells making cross-protective antibodies against HA, including those using IGHV1-69 which encodes in the germline, amino acid residues that make key contacts with a conserved epitope on HA of many subtypes of influenza (Ekiert et al. 2009; Sui et al. 2009). Thus, when care is taken to avoid activation of strain-specific memory B cells, most subjects are able to make such cross-reactive or heterosubtypic protective antibodies, providing a broad-spectrum influenza vaccine.

The present disclosure shows that the nH1N1 vaccine, prepared using the template used for the preparation of conventional seasonal influenza vaccines every year and given safely to millions of humans, can induce unprecedented levels of protective heterosubtypic, antibodies against the hemagglutinin stem.

Further, there is among those skilled in the art, much knowledge of the production of gp140 protein or viral vectors expressing gp160 immunogens that are capable of inducing neutralizing antibodies against HIV-1, albeit against a restricted number of isolates of HIV-1 (Karlsson Hedstam et al, 2008, Kwong and Wilson, 2009 and Rerks-Ngarm et al, 2009). The present use of these gp140 proteins or DNA or viral vectors expressing gp160 in HIV-1 vaccines involve repeated immunization with gp140 or gp160 from the same or a similar isolate of HIV-1. The rationale is that broadly neutralizing antibodies are very rare and have many somatic mutations and have unusual structures that prolonged immunization with the same antigen or similar antigens (for example with a protein gp140 and a DNA or viral vector expressing a similar gp160) is necessary (Karlsson Hedstam et al, 2008, Kwong and Wilson, 2009 and Rerks-Ngarm et al, 2009). In contrast, the present disclosure teaches that a dominant broadly neutralizing antibody response against influenza virus can be stimulated in humans with vaccination with a unique antigen, in this case HA. This in striking contrast to the weak and low heterosubtypic antibody response to repeated vaccination with drifted versions of seasonal influenza (Corti et al. 2010 and Wrammert et al. 2011). Thus, existing HIV-1 gp140 or gp160 antigens that are substantially antigenically different and are from different Clades of HIV-1 (for example from Clade A and Clade B) can be re-deployed as unique antigens used according to the presently disclosed methodology, to induce broadly neutralizing antibodies against HIV-1.

Methods

These studies were approved by the Research Ethics Boards of the University of British Columbia and the University of Toronto. Blood was collected from convalescent patients with laboratory-confirmed nH1N1 Infections or from subjects vaccinated with the adjuvanted nH1N1 influenza vaccine (Arepanrix™). Peripheral blood monocytes (PBMC) and plasma samples were prepared and frozen. RT-PCR and cloning of cDNA encoding the variable regions of antibodies (McLean et al. 2005) was performed with three cellular sources, in two cases Individual PB purified by FACS, either randomly chosen or purified by multicolour FACS as binding to fluorescently labelled nH1 HA, and in the third, single clones expanded from FACS-purified single memory B cells that bound to fluorescent nH1 HA as described in PCT/CA2006/001074. PB studied were collected 7-10 days after exposure to nH1N1 antigens and memory B cells 2-8 weeks. IgG1 monoclonal antibodies were transiently expressed and purified as before (McLean et al. 2005), and binding to purified trimeric recombinant snH1 HA was determined through an ELISA. nH1N1 microneutrallzation assays were performed as outlined by the WHO Manual on Animal Influenza Diagnosis and Surveillance (see world wide web at wpro.who.int/internet/resoures.ashx/CSR/Publications/manual+on+animal+ai+diagnosis+and+surveillance.pdf). Briefly, the monoclonal antibody was subjected to 2-fold serial dilutions in a microtitre plate beginning at 1:2 and an equal volume of pdmH1N1 virus containing 100 TCID50 were added to each dilution and incubated for 2 h at 37° C. The mixtures were added to respective wells of a microtitre plate containing monolayers of MDCK cells in serum-free Megavir medium containing TCPK-treated trypsin and incubated for 3 h after which the medium was replaced by fresh Megavir medium containing TCPK-treated trypsin. The monolayers were monitored on days 3, 4 and 5 for the development of cytopathic effect (CPE). The reciprocal of the highest dilution of the antibody that inhibited the development of viral CPE was designated as the titre. A modified form of the assay consisted of eliminating the step of omitting the removal of the virus-antibody mixtures after 3 h of incubation and allowing the mAb and the virus to remain in the medium for the duration of the assay. The standard WHO neutralization assay was performed in two experienced public health laboratories and did not reveal neutralization by anti-HA stem mAbs. We reasoned that in the standard assay the mixture of the viruses and mAb will only be in contact with the host cells for 3 hr and, if the mAb targets the HA stem rather than the head, the viruses will successfully attach to the host cells. After the virus and the mAb are washed away, some of the mAb will dissociate from viruses that are not endocytosed but attached to the cells. When the virus is finally endocytosed there maybe insufficient mAb bound to the virus to Inhibit fusion. Thus the virus will replicate and can infect other cells, unimpeded by the mAb as it is no longer present. In the modified assay, when the anti-HA stem mAbs were left for the full 3-4 days of the assay, neutralization was observed. The standard WHO assay was designed to detect neutralizing antibodies in serum. Therefore the mixture of virus and titrations of sera was washed away after 3 hr incubation with the host cells because serum contained trypsin inhibitors that blocked the trypsin that was an essential component of the assay. The action of the trypsin was necessary to cleave the hemagglutinin on the virus and render it infectious to the host cells in order to see a cytopathic effect. This format worked well with seasonal influenza where the neutralizing antibodies were directed at the HA heed and blocked viral attachment.

H5N1 Plaque Reduction Assay:

~20,000 plaque forming units (PFU)/ml of influenza viruses A/Goose/Ger/R1400/07 (H5N1) and A/Ck/Ger/R28/03 (H7N7) were incubated with the indicated mAbs at three different concentrations (40 μg/mL, 20 μg/mL, and 10 μg/mL) at 37° C. for 1 h. 50 μl of a 1:10 dilution of the virus-antibody mixtures (containing ~100 PFU) were transferred in triplicate onto MDCK cell monolayers in 96 well plates and incubated for 1 h at 37° C. Cells were then washed and overlaid with 1.5% CMC. 30 h later, plaques were visualized by immunostaining using a mouse monoclonal anti-NP antibody (F26NP9-2-1) (Weingartl et al 2010). Plaques were counted and % neutralization was calculated by setting the infection without mAb as 0% neutralization. Data shown are the mean of triplicate measurements with SD.

Binding to Cell-Expressed H5 HA:

Recombinant adenoviruses expressing influenza A HA (AdHA) from A/Hong Kong/156/97 (H5N1) (Hoelscher, M. A., et al, 2008) were provided by Dr. Suryaprakash Sambhara (Centres for Disease Control and Prevention, Atlanta, Ga.). The AdHA proprotein convertase (AdHA-PC) containing the HA multi-basic cleavage site was utilized. The Adenovirus empty (AdEmpty) was used as a negative control (Viraquest Inc). To promote HA stability, $NH_4Cl$ (10 mM) was added to the culture medium during AdHA infection. Monolayers of A549 cells in 96-well plates were infected with AdHA at a MOI of 500 and incubated for 40 h prior to fixation with 4% formaldehyde. Then, cells were incubated with the indicated concentrations of mAb and treated with FITC-labelled anti-human immunoglobulin antibodies. Nuclei were counterstained with Hoechst. Images were recorded and analyzed/counted using the Cellomics instrument (Thermo Scientific). Data shown are the average of duplicate measurements from a representative experiment.

Assay for Inhibition of HA-Mediated Fusion:

A549 cells were seeded and infected with AdHA as described in the method for the binding assay. At 40 h post infection, cells were washed with PBS, and incubated with the indicated antibodies (20 µg/ml) for 30 min at 37° C. Then, cells were washed again and treated with fusion buffer (10 mM HEPES, 10 mM MES, pH 5) for 5 min at room temperature. Media was replaced with normal cell culture media and cells were incubated at 37° C. for a 5 h period to allow for syncytia formation. To monitor syncytia formation, cells were labelled with 10 µM Cell Tracker Green CMFDA (Molecular Probes) for 30 min at 37° C., followed by further incubation for 30 min in fresh media before samples were fixed with 4% formaldehyde. Nuclei were counterstained with Hoechst dye (1 µg/ml). Images were analyzed using the Cellomics system.

Therapeutic and Prophylactic Testing of Antibodies Against Fatal pdmH1N1 and H5N1 Pneumonia in Mice:

The human clinical isolate of pandemic H1N1 influenza, A/Halifax/210/2009 or the H5N1 vaccine strain, A/Hong Kong/213/2003 on the PR8/34 backbone were used to induce fatal viral pneumonia in CD-1 mice or BALB/c mice respectively. Groups of 5 CD-1 or BALB/c mice (19-21 Gm, females) were infected under halothane anaesthesia (3.5% in $O_2$) with 50 µL of $2\times10^5$ PFU of either H5N1 or pmdH1N1 virus in PBS. Mice were either treated with an intraperitoneal injection of 0.5 ml of purified monoclonal antibodies 1 day before or 1-2 days after infection to monitor protective or therapeutic effects. Controls were treated with only PBS. Survival and weight-loss was monitored for 12-14 days to assess the effects against fatal pandemic H1N1 or H5N1 infections in mice. Similarly, mice were either treated with an intraperitoneal injection of 0.4 ml of human plasma 1 day before or 0.4 ml of human plasma for each of 3, 2 or 1 days before infection with H5N1 to monitor protective effects.

Statistical Analysis:

Statistical analyses were carried out in R (Version 2.9.1., The R Foundation for Statistical Computing, (see world wide web at r-project.org) and Sigmaplot 11.2. Continuous variables were compared using the Mann-Whitney rank sum. For estimation of the probability of V-gene usage we used the binomial distribution.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

Human monoclonal antibodies binding recombinant hemagglutinin from nH1N1

| mAb | IGHV | D | J | κ/λ | IGK/LV | J | Mutations |
|---|---|---|---|---|---|---|---|
| (A) mAb generated from plasmablasts | | | | | | | |
| I3-15 | 1-69*01 | 3-10 | 6 | κ | 1-39*01 | 2 | 18 |
| I4-112# | 1-2*02 | 6-19 | 3 | λ | 2-8*01 | 2 | 5 |
| I4-115# | 3-20*01 | 3-10 | 4 | κ | 3-11*01 | 1 | 30 |
| I4-128# | 1-69*01 | 5-5 | 5 | κ | 3-11*01 | 1 | 13 |
| I4-109# | 3-33*01 | 4-17 | 4 | λ | 1-40*01 | 2 | 16 |
| I5-24 | 1-69*02 | 3-22 | 4 | κ | 3-20*01 | 2 | 29 |
| I5-52 | 1-18*01 | 3-16 | 6 | κ | 2-30*01 | 1 | 11 |
| I5-69 | 1-69*02 | 5-24 | 4 | κ | 3-11*01 | 5 | 8 |
| I5-7 | 1-69*12 | 3-10 | 3 | κ | 3-15*01 | 1 | 29 |
| V2-1 | 3-30*18 | 1-26 | 6 | κ | 3-20*01 | 1 | 15 |
| V2-2 | 4-39*01 | 6-13 | 5 | λ | 1-40*01 | 1 | 33 |
| V2-3 | 4-39*01 | 6-13 | 5 | λ | 1-40*01 | 1 | 33 |
| V2-4 | 4-39*01 | 6-13 | 5 | λ | 1-40*01 | 1 | 31 |
| V2-11 | 4-39*01 | 6-13 | 5 | λ | 1-40*01 | 1 | 21 |
| V2-36 | 4-39*01 | 6-13 | 5 | λ | 1-40*01 | 1 | 33 |
| V2-38 | 4-39*01 | 6-13 | 5 | λ | 1-40*01 | 1 | 34 |
| V2-7 | 4-39*01 | 6-13 | 5 | λ | 1-40*01 | 1 | 21 |
| V2-12 | 4-39*01 | 3-22 | 4 | κ | 4-1*01 | 3 | 34 |
| V4-1 | 1-69*06 | 5-12 | 4 | κ | 3-20*01 | 2 | 29 |
| V4-9 | 1-69*02 | 7-27 | 5 | κ | 3-15*01 | 1 | 34 |
| V4-12 | 3-33*02 | 5-24 | 4 | λ | 3-1*01 | 3 | 31 |
| V4-17H | 4-39*01 | 3-3 | 4 | λ | 1-47*02 | 2 | 19 |
| V4-18 | 1-69*06 | 5-12 | 4 | κ | 3-20*01 | 2 | 23 |
| V4-23 | 1-69*02 | 7-27 | 6 | κ | 1-39*01 | 1 | 34 |
| V4-29 | 1-69*01 | 5-5 | 6 | λ | 2-14*01 | 2 | 28 |
| (B) mAb generated from memory B cells | | | | | | | |
| I4-1G8 | 2-70*11 | 2-8 | 6 | λ | 3-1*01 | 1 | 5 |
| I4-1C4 | 1-69*09 | 4-23 | 5 | κ | 3-11*01 | 1 | 23 |
| I4-1F7 | 3-66*01 | 1-26 | 2 | κ | 3-15*01 | 3 | 0 |
| I8-1B6 | 1-69*01 | 3-3 | 4 | λ | 2-14*01 | 1 | 22 |
| I14-2B7 | 1-18*01 | 2-8 | 6 | κ | 2-30*01 | 2 | 3 |
| I14-1F8 | 5-51*01 | 5-12 | 6 | κ | 3-11*01 | 5 | 10 |
| I14-2B6 | 4-59*01 | 2-8 | 3 | κ | 1-39*01 | 1 | 19 |
| I14-2C5 | 3-30*03 | 6-6 | 4 | κ | 1-6*01 | 2 | 22 |
| I14-1D9 | 1-69*04 | 2-15 | 4 | κ | 3-15*01 | 2 | 10 |
| V3-1B9 | 3-11*01 | 3-3 | 3 | κ | 1-12*01 | 4 | 10 |
| V3-1C6 | 1-69*01 | 1-1 | 6 | λ | 7-43*01 | 3 | 18 |
| V3-1E8 | 3-33*01 | 1-26 | 4 | λ | 3-25*03 | 3 | 11 |
| V3-2C10 | 1-69*01 | 5-12 | 5 | κ | 1-39*01 | 4 | 21 |
| V3-2C2 | 1-69*06 | 3-9 | 4 | κ | 1-39*01 | 4 | 9 |
| V3-2C3 | 1-69*01 | 3-10 | 5 | κ | 1-5*03 | 2 | 6 |
| V3-2F10 | 1-69*06 | 3-22 | 4 | κ | 1-5*03 | 1 | 17 |
| V3-2G6 | 1-69*01 | 3-16 | 4 | κ | 3-20*01 | 2 | 18 |
| V3-3B3 | 1-69*01 | 3-10 | 3 | λ | 2-11*01 | 1 | 6 |
| V3-3B6 | 1-69*06 | 2-2 | 6 | κ | 3-20*01 | 1 | 19 |
| V3-2E2 | 1-69*01 | 3-10 | 4 | κ | 1-16*02 | 4 | 14 |
| V3-3C11 | 1-69*01 | 5-12 | 4 | λ | 2-14*01 | 1 | 9 |
| V3-1G10 | 1-69*06 | 1-14 | 5 | κ | 3-15*01 | 2 | 25 |
| V3-3D2 | 1-69*01 | 1-14 | 6 | κ | 1-16*-01 | 4 | 21 | mAbs are named systematically, with the initial letter and number indicating the subject from which it had been generated, with I or V indicating that they were generated from a subject infected (I) or vaccinated (V) with the nH1N1 virus. Mutations listed are in IGHV. All mAbs bound by ELISA to purified recombinant ectodomain of HA of nH1N1 and to the nH1N1 vaccine, and all but V4-17 (*) also bound to the seasonal 2009/2010 vaccine and to H5 HA (A/Vietnam/1203/2004, Clade1). mAbs in section (A) were generated from PB, with # indicating those generated from randomly chosen PB that were not sorted for their ability to bind to HA from nH1N1; other mAbs in section (A) were generated from PB purified by their binding to to HA from nH1N1. mAbs in section (B) were generated from memory B cells purified by their binding to to HA from nH1N1.

TABLE 2

Sequences: The CDRs as defined by IGMT are underlined. Also given (but not underlined) are amino acids in the framework close to the CDRs that are mutated. The latter residues may be replaced in the framework when these CDR's are transplanted into an immunoglobulin framework to recreate the binding site of these antibodies.

1 V2-36
Seq 1H
ELRLHESGPGLVKPSGTLSLTCTVSGGSISGGSHYWAWIRQSPGKGLEWIG
S
IYYSGSTYDSPSLKSRLSMSVDKSKNQFHLTLRSVTAADTAVYFCAKHESDS
SSWHTGWNWFDP (SEQ ID NO: 8)

Seq1L
QSVLTQPSSVSGAPGQRVTISCTGSYS NIGTGFDVHVVYQHLPGKAPKLLIFG
NN NRPSGVPDRFSGSKSGTSASLAITGLQPEDEGDYYCQSFDSSLSGSNV
(SEQ ID NO: 7)

Seq1cdrh1 GGSISGGSHY WA (SEQ ID NO: 4 - underlined, SEQ ID NO: 81)

Seq1cdrh2 IYYSGST YDS (SEQ ID NO: 5 - underlined, SEQ ID NO: 102)

Seq1cdrh3 AKHESDSSSWHTGWNWFDP (SEQ ID NO: 6)

Seq1cdrl1 YSNIGTGFD (SEQ ID NO: 1)

Seq1cdrl2 GNN (SEQ ID NO: 2)

Seq1cdrl3 QSFDSSLSGSNV (SEQ ID NO: 3)

2 V2-7
Seq2h
QLQLQESGPGLVKTSETLSLTCTVSGGSIRGGTNYWAWIRQPPGKGPEWL
GSVYYSGSTYDNPSLKSRVSIYVDTSKNKFSLRLRSVTAADTAIYYCARHES
DSSSWHTGWNWFDPWGQGTLVTVSSAS (SEQ ID NO: 16)

Seq2l
QSMLTQPPSVSGAPGQRVTISCTGSSTNIGAGLAVHVVYQHLPGTAPKLLIY
GNTNRPSGVPDRFSGSKSGTTASLAITGLQADDEADYYCQSFDGSLSGSNV
FGTGTKVTVLTAA
(SEQ ID NO: 15)

Seqcdrh1 GGSIRGGTNY WA (SEQ ID NO: 12 - underlined, SEQ ID NO: 82)

Seqcdrh2 VYYSGSTYD (SEQ ID NO: 13 - underlined, SEQ ID NO: 83)

Seqcdrh3 ARHESDSSSWHTGWNWFDP (SEQ ID NO: 14)

Seqcdrl1 STNIGAGLA (SEQ ID NO: 9)

Seqcdrl2 GNT (SEQ ID NO: 10)

Seqcdrl3 QSFDGSLSGSNV (SEQ ID NO: 11)

3 V3-2G6
Seq3h
QSQVQLEQSGAEVKRPGSSVKVSCQTSGGTFSSFAFSVVVRQAPGQGLEW
VGG IIGMFGTTSYAQKFQGRVTISADESTSTAYMELSSLRSDDTAIYYC
ARGKKYYHDTLDY (SEQ ID NO: 24)

Seq3l
EIVLTQSPGTLSLSPGERATLSCRASQIVSSSQLAVVYQHKPGQAPRLLIYAA
S SRATGIPDRFSGSGSGTDFTLTISRLEPEDFAVYYCQQYGTSHA (SEQ ID
NO: 23)

Seq3cdrh1 GGTFSSFA F (SEQ ID NO: 20 - underlined, SEQ ID NO: 84)

Seq3cdrh2 IIGMFGTT S (SEQ ID NO: 21 - underlined, SEQ ID NO: 85)

Seq3cdrh3 ARGKKYYHDTLDY (SEQ ID NO: 22)

Seq3cdrl1 QIVSSSQ (SEQ ID NO: 17)

Seq3cdrl2 AAS (SEQ ID NO: 18)

Seq3cdrl3 QQYGTSHA (SEQ ID NO: 19)

TABLE 2-continued

Sequences: The CDRs as defined by IGMT are underlined. Also given (but not underlined) are amino acids in the framework close to the CDRs that are mutated. The latter residues may be replaced in the framework when these CDR's are transplanted into an immunoglobulin framework to recreate the binding site of these antibodies.

4. I8-1B6
Seq4h
QAQLEQSGAEVRRPGSSVKVACKTSGGIFSNFAVSVVVRQAPGQGLEWMG
GILSIFRTTNYAQKFQGRVTITADESTSTAYMELNSLRSDDTAVYYCARSITN
LYYYYMDV (SEQ ID NO: 32)

Seq4l
QSALTQPASVSGSPGQSITVSCTGTNSDVGTYNYVSWFQQHPGEAPKVIIF
DVS HRPSGVSNRFSGSKSGNTASLTISGLQTEDEADYYCSSYTTSNTRV
(SEQ ID NO: 31)

Seq4cdrh1 GGIFSNFA V (SEQ ID NO: 28 - underlined, SEQ ID NO: 86)

Seq4cdrh2 ILSIFRTT (SEQ ID NO: 29)

Seq4cdrh3 ARSITNLYYYYMDV (SEQ ID NO: 30)

Seq4cdrl1 NSDVGTYNY (SEQ ID NO: 25)

Seq4cdrl2 DVS H (SEQ ID NO: 26 - underlined, SEQ ID NO: 87)

Seq4cdrl3 SSYTTSNTRV (SEQ ID NO: 27)

5 V3-3D2
Seq5h
QVQLVQSGAEVKKPGSSVKVSCKAPGVIFNAYAMSVVVRQAPGQGLEWMG
GITGVPHTATYAPKFQGRVTITADESTSTAYMELSSLRSDDTAVYYCARGPK
YYHSYMDV (SEQ ID NO: 40)

Seq5l
DIQMTQSPSSLSASVGDRVTITCRASQDISNYVAWFQQKPGKTPKSLMYAT
S KLQNGVPSRFSGSGSGTDFTLTISSLQSEDFATYYCQQYSRYPPT (SEQ
ID NO: 39)

Seq5cdrh1 P GVIFNAYA M (SEQ ID NO: 36 - underlined, SEQ ID NO: 88)

Seq5cdrh2 ITGVFHTA T (SEQ ID NO: 37 - underlined, SEQ ID NO: 89)

Seq5cdrh3 ARGPKYYHSYMDV (SEQ ID NO:38)

Seq5cdrl1 QDISNY V (SEQ ID NO: 33 - underlined, SEQ ID NO: 90)

Seq5cdrl2 MY ATS K (SEQ ID NO: 34 - underlined, SEQ ID NO: 91)

Seq5cdrl3 QQYSRYPPT (SEQ ID NO: 35)

6 V3-1G10
Seq6h
QVQLVQSGAEVKKPGSTVKVSCEASGVTFNHYTVSVVVRQAPGQGLEWMG
G IIPLFGTADYAQKFQDRVTITADRSTGTAYMELSSLRPEDTALYYC
ARSGTTKTRYNWFDP (SEQ ID NO: 48)

Seq6l
EIIMTQSPATLSLSPGERVTLSCRASQSVGTNLAVVYQQKPGQAPRLLIFGAS
TRATGIPARFSGSGSETEFTLSISSLQSEDFAVYYCQHYNNWPPYT (SEQ ID
NO: 47)
Seq6cdrh1 EAS GVTFNHYT V (SEQ ID NO: 44 - underlined, SEQ ID NO: 92)

Seq6cdrh2 IIPLFGTA D (SEQ ID NO: 45 - underlined, SEQ ID NO: 93)

Seq6cdrh3 ARSGTTKTRYNWFDP (SEQ ID NO: 46)

Seq6cdrl1 QSVGTN (SEQ ID NO: 41)

Seq6cdrl2 F GAS (SEQ ID NO: 42 - underlined, SEQ ID NO: 94)

Seq6cdrl3 QHYNNWPPYT (SEQ ID NO: 43)

TABLE 2-continued

Sequences: The CDRs as defined by IGMT are underlined. Also given (but not underlined) are amino acids in the framework close to the CDRs that are mutated. The latter residues may be replaced in the framework when these CDR's are transplanted into an immunoglobulin framework to recreate the binding site of these antibodies.

7 I5-24
Seq7h
QFQLVQSGAEVRKPGSSVKVSCTASGGTFSRYTVNVVVRQAPGQGLQWM
GR FIPLLGMTNYAQRFQGRATITADKSTTTAFLELSSLTSEDTAVYFC
ARHDSSGYHPLDY (SEQ ID NO: 56)

Seq7l
EIVLTQSPGTLSLSPGERATLSCRASQSLSSGHLAVVYQQKPGQAPRLLIY
GASSRATGIPDRFSGSGSGTDFTLTISRLEPEDFAVYYCQQYAVFLYT (SEQ
ID NO: 55)

Seq7cdrh1 TAS GGTFSRYT VN (SEQ ID NO: 52 - underlined, SEQ ID
NO: 95)

Seq7cdrh2 FIPLLGMT (SEQ ID NO: 53)

Seq7cdrh3 ARHDSSGYHPLDY (SEQ ID NO: 54)

Seq7cdrl1 QSLSSGH (SEQ ID NO: 49)

Seq7cdrl2 GAS (SEQ ID NO: 50)

Seq7cdrl3 QQYAVFLYT (SEQ ID NO: 51)

8 I4-128
Seq8h
QVQLVQSGAEVKKPGSSVMVSCKASGGTFSTYGVSVVVRQAPGQGLEVVVG
G IIPIFGTAKYAQKFQGRVTITADESSTTAYMELSRLRSEDTAVYYC
ARPNTYGYILPVY (SEQ ID NO: 64)

Seq8l
DIQMTQSPSTLSASVGDRVTIGCRASQTISTYLAVVYQQVPGKAPKLLIYMAS
TLESGVPSRFSGSGSGTEFTLTISSLQPGDFATYYCQHYNTYSST (SEQ ID
NO: 63)

Seq8cdrh1 GGTFSTYG V (SEQ ID NO: 60 - underlined, SEQ ID NO: 96)

Seq8cdrh IIPIFGTA K (SEQ ID NO: 61 - underlined, SEQ ID NO: 97)

Seq8cdrh3 ARPNTYGYILPVY (SEQ ID NO: 62)

Seq8cdrl1 QTISTY (SEQ ID NO: 57)

Seq8cdrl2 MAS T (SEQ ID NO: 58 - underlined, SEQ ID NO: 98)

Seq8cdrl3 QHYNTYSST (SEQ ID NO: 59)

9 V4-17
Seq9h
QLQLQESGPGLVKPSETLSLTCTVSGGSITRNSYFWGWIRQPPGKGLEWIG
S
MYYDGTTYHNPSLKSRLTLSADTSKNQFSVRLSSVTAADTAVYYCARHHVT
ELRVLEWLPKSDY (SEQ ID NO: 72)

Seq9l
QSVLTQPPSASGTPGQRVTISCSGSSSNIGTYYVHVVYQHLPGTAPKLLIY
DNNQRPSGVPDRFSGSKSGTSASLAISGLRSEDEADYHCAAWDDSLSGVV
(SEQ ID NO: 71)

Seq9cdrh1 GGSITRNSYF (SEQ ID NO: 68)

Seq9cdrh2 MYYDGTT YH (SEQ ID NO: 69 - underlined, SEQ ID NO: 99)

Seq9cdrh3 ARHHVTELRVLEWLPKSDY (SEQ ID NO: 70)

Seq9cdrl1 SSNIGTYY VH (SEQ ID NO: 65 - underlined, SEQ ID NO: 100)

Seq9cdrl2 DNN (SEQ ID NO: 66)

Seq9cdrl3 AAWDDSLSGVV (SEQ ID NO: 67)

TABLE 2-continued

Sequences: The CDRs as defined by IGMT are underlined. Also given (but not underlined) are amino acids in the framework close to the CDRs that are mutated. The latter residues may be replaced in the framework when these CDR's are transplanted into an immunoglobulin framework to recreate the binding site of these antibodies.

10 V3-2C3
Seq10h QVQLVQSGAEVKKPGSSVKVSCKASGGTFNNYA
VSVVVRQAPGQGLEWMGGIIPIFGTANYAHKFQGRVTITVDESTSTAYMELS
SLRSEDTAMYYCARVCSFYGSGSYYNVFCY (SEQ ID NO: 80)

Seq10l
DIQMTQSPSTLSASAGDRVTITCRASQSISSWLAVVYQQKPGKAPKLLIY
KASSLESGVPSRFSGSGSGTEFTLTISSLQPDDFATYYCQHYNSYSQTFGQ
GTKVEIKRTAAA (SEQ ID NO: 79)

Seq10cdrh1 GGTFNNYA V (SEQ ID NO:76 - underlined, SEQ ID NO:101)

Seq10cdrh2 IIPIFGTA (SEQ ID NO: 77)

Seq10cdrh3 ARVCSFYGSGSYYNVFCY (SEQ ID NO: 78)

Seq10cdrl1 QSISSW (SEQ ID NO: 73)

Seq10cdrl2 KAS (SEQ ID NO: 74)

Seq10cdrl3 QHYNSYSQT (SEQ ID NO: 75)

TABLE 3

Expected versus observed IGHV1-69 usage of mAbs binding to snHA per subject

| Subject | # of anti-snHA mAbs | | *Probability of observed result |
|---|---|---|---|
| | Total | Using IGHV1-69 | |
| I3 | 1 | 1 | 0.04 |
| I4 | 8 | 2 | 0.03 |
| I5 | 4 | 3 | 0.0002 |
| I8 | 1 | 1 | 0.04 |
| I14 | 5 | 1 | 0.2 |
| V3 | 14 | 12 | 1.E-15 |
| V4 | 7 | 5 | 2E-6 |
| V2 | 9 | 0 | 0.7 |

*based on the average frequency of usage of IGHV1-69 in human antibodies of 4%.
Note that all but 2 of the 8 subjects (V2 and I14) had a greater than expected frequency of IGHV1-69-using mAbs. The total proportion of mAbs using IGHV1-69 was 52% (95% confidence intervals of 38-66%). If it is hypothesized that in the response to nH1N1, IGHV1-69 is used in 52% of mAbs, the probability that the results obtained with subject V2 occurred by chance was only 0.002, whereas for I14 the chance was 0.16 (i.e. was likely).

REFERENCES

Allen, C. D., Okada, T., Tang, H. L. & Cyster, J. G. Imaging of germinal center selection events during affinity maturation. *Science* 315, 528-531 (2007).

Babcook, J. S., Leslie, K. B., Olsen, O. A., Salmon, R. A. & Schrader, J. W. A novel strategy for generating monoclonal antibodies from single, isolated lymphocytes producing antibodies of defined specificities. *Proceedings of the National Academy of Sciences of the United States of America* 93, 7843-7848 (1996).

Bardiya, N. & Bae, J. H. Influenza vaccines: recent advances in production technologies. *Appl Microbiol Biotechnol* 67, 299-305, doi:10.1007/s00253-004-1874-1 (2005).

Barington, T., Heilmann, C. & Andersen, V. Quantitation of antibody-secreting cells in the blood after vaccination with *Haemophilus influenzae* type b conjugate vaccine [published erratum appears in Scand J Immunol 1990 July; 32(1):59]. *Scand J Immunol* 31, 515-522 (1990).

Burioni, R. et al. Monoclonal antibodies isolated from human B cells neutralize a broad range of H1 subtype influenza A viruses including swine-origin Influenza virus (S-OIV). *Virology* 399, 144-152.

Chen, G. L. & Subbarao, K. Attacking the flu: neutralizing antibodies may lead to 'universal' vaccine. *Nat Med* 15, 1251-1252 (2009).

Corti, D. et al. Heterosubtypic neutralizing antibodies are produced by individuals immunized with a seasonal influenza vaccine *Journal of Clinical Investigation* 120, 1663-1673 (2010).

de Wildt, R. M., Hoet, R. M., van Venrooij, W. J., Tomlinson, I. M. & Winter, G. Analysis of heavy and light chain pairings indicates that receptor editing shapes the human antibody repertoire. *Journal of Molecular Biology* 285, 895-901 (1999).

Ding, N., Wu, N., Xu, Q., Chen, K. & Zhang, C. Molecular evolution of novel swine-origin A/H1N1 influenza viruses among and before human. *Virus Genes* 39, 293-300 (2009).

Doherty, P. C. & Kelso, A. Toward a broadly protective influenza vaccine. *J Clin Invest* 118, 3273-3275 (2008).

Eisenlohr, L. C., Gerhard, W. & Hackett, C. J. Role of receptor-binding activity of the viral hemagglutinin molecule in the presentation of influenza virus antigens to helper T cells. *Journal of Virology* 61, 1375-1383 (1987).

Ekiert, D. C. et al. Antibody recognition of a highly conserved influenza virus epitope. *Science* 324, 246-251 (2009).

Ekiert, D. C., et al. A Highly Conserved Neutralizing Epitope on Group 2 Influenza A Viruses. *Science*. (2011) July 7 Epub ahead of print Garcia, J. M. et al. Heterosubtype neutralizing responses to influenza A (H5N1) viruses are mediated by antibodies to virus haemagglutinin. *PLoS One* 4, e7918, (2009).

Garten, R. J., et al. Antigenic and genetic characteristics of swine-origin 2009 A(H1N1) influenza viruses circulating in humans. *Science* 325, 197-201 (2009).

Gioia, C. et al. Cross-subtype immunity against avian influenza in persons recently vaccinated for influenza. *Emerging Infectious Diseases* 14, 121-128 (2008).

Hancock, K. et al. Cross-Reactive Antibody Responses to the 2009 Pandemic H1N1 Influenza Virus. *N Engl J Med* (2009).

Heilmann, C., Henrichsen, J. & Pedersen, F. K. Vaccination-induced circulation of human B cells secreting type-specific antibodies against pneumococcal polysaccharides. *Scand J Immunol* 25, 61-67 (1987).

Hoelscher, M. A., et al. A Broadly Protective Vaccine against Globally Dispersed Clade 1 and Clade 2 H5N1 Influenza Viruses. *The Journal of Infectious Diseases* 197, 1185-1188 (2008).

Itoh, Y. et al. In vitro and in vivo characterization of new swine-origin H1N1 influenza viruses. *Nature* 460, 1021-1025 (2009).

Karlsson Hedestam, G. B., et al. The challenges of eliciting neutralizing antibodies to HIV-1 and to influenza virus. *Nat Rev Micro* 6, 143-155 (2008).

Kashyap, A. K. et al. Combinatorial antibody libraries from survivors of the Turkish H5N1 avian influenza outbreak reveal virus neutralization strategies. *Proc Natl Acad Sci USA* 105, 5986-5991(2008).

Klenk, H. D., Rott, R., Orlich, M. & Bloedorn, J. Activation of influenza A viruses by trypsin treatment. *Virology* 68, 426-439 (1975).

Kropff, B., Landini, M. P. & Mach, M. An ELISA using recombinant proteins for the detection of neutralizing antibodies against human cytomegalovirus. *J Med Virol* 39, 187-195 (1993).

Lynch, G. W., Selleck, P. & Sullivan, J. S. Acquired heterosubtypic antibodies in human immunity for avian H5N1 influenza. 3, 205-209 (2009).

McLean, G. R. et al. Recognition of human cytomegalovirus by human primary immunoglobulins identifies an innate foundation to an adaptive immune response. *J Immunol* 174, 4768-4778 (2005).

McLean, G. R., Cho, C. W. & Schrader, J. W. Autoreactivity of primary human immunoglobulins ancestral to hypermutated human antibodies that neutralize HCMV. *Mol Immunol* 43, 2012-2022 (2006).

Nossal, G. J. V. & Lewis, H. Variation In Accessible Cell Surface Immunoglobulin Among Antibody-Forming Cells. *The Journal of Experimental Medicine* 135, 1416-1422 (1972).

Ohlin, M., Sundqvist, V. A., Mach, M., Wahren, B. & Borrebaeck, C. A. Fine specificity of the human immune response to the major neutralization epitopes expressed on cytomegalovirus gp58/116 (gB), as determined with human monoclonal antibodies. *J Virol* 67, 703-710 (1993).

Odendahl, M. et al. Generation of migratory antigen-specific plasma blasts and mobilization of resident plasma cells in a secondary immune response. *Blood* 105, 1614-1621 (2005).

Okuno, Y., Isegawa, Y., Sasao, F. & Ueda, S. A common neutralizing epitope conserved between the hemagglutinins of influenza A virus H1 and H2 strains. *J Virol* 67, 2552-2558 (1993).

Paus, D. et al. Antigen recognition strength regulates the choice between extrafollicular plasma cell and germinal center B cell differentiation. The Journal of Experimental Medicine 203, 1081-1091 (2006).

Pinna, D., Corti, D., Jarrossay, D., Sallusto, F. & Lanzavecchia, A. Clonal dissection of the human memory B-cell repertoire following infection and vaccination. *Eur J Immunol* 39, 1260-1270, doi:10.1002/eji.200839129 (2009).

Rerks-Ngarm, S., et al. Vaccination with ALVAC and AIDS-VAX to prevent HIV-1 infection in Thailand. *The New England Journal of Medicine* 361, 2209-2220 (2009).

Russell, S. M. & Liew, F. Y. T cells primed by influenza virion internal components can cooperate in the antibody response to haemagglutinin. *Nature* 280, 147-148 (1979).

Sagawa, H., Ohshima, A., Kato, I., Okuno, Y. & Isegawa, Y. The immunological activity of a deletion mutant of influenza virus haemagglutinin lacking the globular region. *J Gen Virol* 77, 1483-1487 (1996).

Sasso, E. H., Johnson, T. & Kipps, T. J. Expression of the immunoglobulin VH gene 51p1 is proportional to its germline gene copy number. *Journal of Clinical Investigation* 97, 2074-2080 (1996).

Settembre, E. C., Dormitzer, P. R. & Rappuoli, R. Learning from the 2009 H1N1 pandemic: prospects for more broadly effective influenza vaccines. *J Mol Cell Biol* 3, 144-146. (2011).

Schwickert, T. A., et al. A dynamic T cell limited checkpoint regulates affinity-dependent B cell entry into the germinal center *The Journal of Experimental Medicine*. 208, 1243-1252 (2011)

Smith, K. G., Light, A., Nossal, G. J. & Tarlinton, D. M. The extent of affinity maturation differs between the memory and antibody-forming cell compartments in the primary immune response. *Embo J* 16, 2996-3006 (1997).

Steel, J. et al. Influenza Virus Vaccine Based on the Conserved Hemagglutinin Stalk Domain. mBio1, e00018-00010 (2010).

Sui, J. et al. Structural and functional bases for broad-spectrum neutralization of avian and human influenza A viruses. *Nat Struct Mol Biol* 16, 265-273 (2009).

Tangye, S. G. & Tarlinton, D. M. Memory B cells: effectors of long-lived immune responses. *Eur J Immunol* 39, 2065-2075 (2009).

Thomson, C. A. et al. Germline V-genes sculpt the binding site of a family of antibodies neutralizing human cytomegalovirus. *Embo J* (2008).

Throsby, M. et al. Heterosubtypic neutralizing monoclonal antibodies cross-protective against H5N1 and H1N1 recovered from human IgM+ memory B cells. *PLoS One* 3, e3942 (2008).

Victora, G. D., et al. Germinal center dynamics revealed by multiphoton microscopy with a photoactivatable fluorescent reporter. *Cell* 143, 592-605 (2010)

Wagner, B. et al. A continuous sequence of more than 70 amino acids is essential for antibody binding to the dominant antigenic site of glycoprotein gp58 of human cytomegalovirus. *Journal of Virology* 66, 5290-5297 (1992).

Wang, T. T. et al. Broadly protective monoclonal antibodies against H3 influenza viruses following sequential immunization with different hemagglutinins. *PLoS Pathog* 6, e1000796. (2010).

Wei, C.-J., et al. Cross-neutralization of 1918 and 2009 influenza viruses: role of glycans in viral evolution and vaccine design. *Science Translational Medicine* 2, 24ra21 (2010)a Wei, C.-J., et al. Induction of broadly neutralizing H1N1 influenza antibodies by vaccination. *Science (New York, N.Y.)* 329, 1060-1064 (2010)b.

Weingartl, H. M., et al. Genetic and Pathobiologic Characterization of Pandemic H1N1 2009 Influenza Viruses from a Naturally Infected Swine Herd. *J. Virol.* 84, 2245-2256 (2010).

Wen, L., et al. Limiting dilution assay for human B cells based on their activation by mutant EL4 thymoma cells: total and antimalaria responder B cell frequencies. *Eur J Immunol* 17, 887-892 (1987).

Wiley, D. C. & Skehel, J. J. The structure and function of the hemagglutinin membrane glycoprotein of influenza virus. *Annu Rev Biochem* 56, 365-394 (1987).

Wrammert, J. et al. Rapid cloning of high-affinity human monoclonal antibodies against influenza virus. *Nature* 453, 667-671 (2008).

Wrammert, J., et al. Broadly cross-reactive antibodies dominate the human B cell response against 2009 pandemic H1N1 influenza virus infection. *The Journal of Experimental Medicine* 208, 181-193 (2011)

Xu, R. et al. Structural Basis of Preexisting Immunity to the 2009 H1N1 Pandemic Influenza Virus. *Science* 328, 357-360 (2010).

Yen, H.-L. & Webster, R. G. Pandemic influenza as a current threat. *Current Topics in Microbiology and Immunology* 333, 3-24 (2009).

Yoshida, R., et al. Cross-protective potential of a novel monoclonal antibody directed against antigenic site B of the hemagglutinin of influenza A viruses. *PLoS Pathog* 5, e1000350 (2009)

The invention claimed is:

1. A method for inducing a cross-reactive antibody response against an influenza virus in a human subject comprising:
   (a) administering a first hemagglutinin (HA) protein to the human subject; and
   (b) administering a second HA protein to the subject 3-52 weeks after (a);
   wherein the second HA protein comprises a head that is substantially antigenically unrelated to the first HA protein but comprises conserved antigenic sites in the stem or on the head that are the target of protective antibodies that are normally not immunogenic
   wherein the frequency of memory B cells to the first and/or second HA protein in the human subject to be vaccinated is less than 0.01% of IgG-expressing memory B cells circulating in the blood of the human subject or wherein the frequency of memory B cells to the first and/or second HA protein in the human subject to be vaccinated is undetectable or less than 1 per million.

2. The method of claim 1, wherein the first and/or second HA protein is part of an attenuated influenza virus strain or inactivated influenza virus strain.

3. The method of claim 1, wherein the first and/or second HA protein is from a pandemic virus or a virus that normally infects a different host species.

4. The method of claim 1, wherein the first and/or second HA protein is an artificial HA protein having mutations in the head that make it antigenically unrelated to HA that the population to be vaccinated has been exposed to or wherein the first and/or second HA protein is a chimeric HA protein comprising a conserved stem coupled to an antigenically unrelated head.

5. The method of claim 1, further comprising administering an adjuvant with the first and/or second HA protein.

6. The method of claim 1, wherein the second HA antigen is administered at a different anatomical site from the site of the first HA antigen.

7. A method of inducing a cross-reactive antibody response in a human subject comprising:
   (a) administering a first pathogen protein to the human subject; and
   (b) administering a second pathogen protein to the human subject 3-52 weeks after (a),
   wherein the second pathogen is substantially antigenically unrelated to the first pathogen protein but comprises conserved antigenic sites that are the target of protective antibodies that are normally not immunogenic
   wherein the frequency of memory B cells to the first and/or second pathogen protein in the human subject to be vaccinated is less than 0.01% of IgG-expressing memory B cells circulating in the blood of the human subject or wherein the frequency of memory B cells to the first and/or second pathogen protein in the human subject to be vaccinated is undetectable or less than 1 per million.

8. The method of claim 7, wherein the pathogen is influenza, HCMV or HIV-1.

9. The method of claim 1, further comprising:
   (c) administering a third HA protein 3-52 weeks after b), wherein the third HA protein comprises a head that is substantially antigenically unrelated to the heads of the first and second HA proteins but comprises conserved antigenic sites in the stem or on the head that are the target of protective antibodies that are normally not immunogenic.

10. The method of claim 1, further comprising administering one or more additional HA proteins as a mixture or concurrently with the first and/or second HA protein.

* * * * *

SEQUENCE LISTING

```
<160> NUMBER OF SEQ ID NOS: 102

<210> SEQ ID NO 1
<211> LENGTH: 9
<212> TYPE: PRT
<213> ORGANISM: Homo sapiens

<400> SEQUENCE: 1

Tyr Ser Asn Ile Gly Thr Gly Phe Asp
1               5

<210> SEQ ID NO 2
<211> LENGTH: 3
<212> TYPE: PRT
<213> ORGANISM: Homo sapiens

<400> SEQUENCE: 2

Gly Asn Asn
1

<210> SEQ ID NO 3
<211> LENGTH: 12
<212> TYPE: PRT
<213> ORGANISM: Homo sapiens

<400> SEQUENCE: 3

Gln Ser Phe Asp Ser Ser Leu Ser Gly Ser Asn Val
1               5                   10

<210> SEQ ID NO 4
<211> LENGTH: 10
<212> TYPE: PRT
<213> ORGANISM: Homo sapiens

<400> SEQUENCE: 4

Gly Gly Ser Ile Ser Gly Gly Ser His Tyr
1               5                   10

<210> SEQ ID NO 5
<211> LENGTH: 7
<212> TYPE: PRT
<213> ORGANISM: Homo sapiens

<400> SEQUENCE: 5

Ile Tyr Tyr Ser Gly Ser Thr
1               5

<210> SEQ ID NO 6
<211> LENGTH: 19
<212> TYPE: PRT
```

<213> ORGANISM: Homo sapiens

<400> SEQUENCE: 6

Ala Lys His Glu Ser Asp Ser Ser Trp His Thr Gly Trp Asn Trp
1               5                   10                  15

Phe Asp Pro

<210> SEQ ID NO 7
<211> LENGTH: 102
<212> TYPE: PRT
<213> ORGANISM: Homo sapiens

<400> SEQUENCE: 7

Gln Ser Val Leu Thr Gln Pro Ser Ser Val Ser Gly Ala Pro Gly Gln
1               5                   10                  15

Arg Val Thr Ile Ser Cys Thr Gly Ser Tyr Ser Asn Ile Gly Thr Gly
            20                  25                  30

Phe Asp Val His Trp Tyr Gln His Leu Pro Gly Lys Ala Pro Lys Leu
        35                  40                  45

Leu Ile Phe Gly Asn Asn Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Pro Glu Asp Glu Gly Asp Tyr Tyr Cys Gln Ser Phe Asp Ser Ser
                85                  90                  95

Leu Ser Gly Ser Asn Val
            100

<210> SEQ ID NO 8
<211> LENGTH: 116
<212> TYPE: PRT
<213> ORGANISM: Homo sapiens

<400> SEQUENCE: 8

Glu Leu Arg Leu His Glu Ser Gly Pro Gly Leu Val Lys Pro Ser Gly
1               5                   10                  15

Thr Leu Ser Leu Thr Cys Thr Val Ser Gly Gly Ser Ile Ser Gly Gly
            20                  25                  30

Ser His Tyr Trp Ala Trp Ile Arg Gln Ser Pro Gly Lys Gly Leu Glu
        35                  40                  45

Trp Ile Gly Ser Ile Tyr Tyr Ser Gly Ser Thr Tyr Asp Ser Pro Ser
    50                  55                  60

Leu Lys Ser Arg Leu Ser Met Ser Val Asp Lys Ser Lys Asn Gln Phe
65                  70                  75                  80

His Leu Thr Leu Arg Ser Val Thr Ala Ala Asp Thr Ala Val Tyr Phe
                85                  90                  95

Cys Ala Lys His Glu Ser Asp Ser Ser Trp His Thr Gly Trp Asn
                100                 105                 110

Trp Phe Asp Pro
        115

<210> SEQ ID NO 9
<211> LENGTH: 9
<212> TYPE: PRT
<213> ORGANISM: Homo sapiens

<400> SEQUENCE: 9

Ser Thr Asn Ile Gly Ala Gly Leu Ala

<210> SEQ ID NO 10
<211> LENGTH: 3
<212> TYPE: PRT
<213> ORGANISM: Homo sapiens

<400> SEQUENCE: 10

Gly Asn Thr
1

<210> SEQ ID NO 11
<211> LENGTH: 12
<212> TYPE: PRT
<213> ORGANISM: Homo sapiens

<400> SEQUENCE: 11

Gln Ser Phe Asp Gly Ser Leu Ser Gly Ser Asn Val
1               5                   10

<210> SEQ ID NO 12
<211> LENGTH: 10
<212> TYPE: PRT
<213> ORGANISM: Homo sapiens

<400> SEQUENCE: 12

Gly Gly Ser Ile Arg Gly Gly Thr Asn Tyr
1               5                   10

<210> SEQ ID NO 13
<211> LENGTH: 7
<212> TYPE: PRT
<213> ORGANISM: Homo sapiens

<400> SEQUENCE: 13

Val Tyr Tyr Ser Gly Ser Thr
1               5

<210> SEQ ID NO 14
<211> LENGTH: 19
<212> TYPE: PRT
<213> ORGANISM: Homo sapiens

<400> SEQUENCE: 14

Ala Arg His Glu Ser Asp Ser Ser Trp His Thr Gly Trp Asn Trp
1               5                   10                  15

Phe Asp Pro

<210> SEQ ID NO 15
<211> LENGTH: 115
<212> TYPE: PRT
<213> ORGANISM: Homo sapiens

<400> SEQUENCE: 15

Gln Ser Met Leu Thr Gln Pro Pro Ser Val Ser Gly Ala Pro Gly Gln
1               5                   10                  15

Arg Val Thr Ile Ser Cys Thr Gly Ser Ser Thr Asn Ile Gly Ala Gly
            20                  25                  30

Leu Ala Val His Trp Tyr Gln His Leu Pro Gly Thr Ala Pro Lys Leu
        35                  40                  45

Leu Ile Tyr Gly Asn Thr Asn Arg Pro Ser Gly Val Pro Asp Arg Phe
    50                  55                  60

```
Ser Gly Ser Lys Ser Gly Thr Thr Ala Ser Leu Ala Ile Thr Gly Leu
 65                  70                  75                  80

Gln Ala Asp Asp Glu Ala Asp Tyr Tyr Cys Gln Ser Phe Asp Gly Ser
                 85                  90                  95

Leu Ser Gly Ser Asn Val Phe Gly Thr Gly Thr Lys Val Thr Val Leu
            100                 105                 110

Thr Ala Ala
        115
```

<210> SEQ ID NO 16
<211> LENGTH: 129
<212> TYPE: PRT
<213> ORGANISM: Homo sapiens

<400> SEQUENCE: 16

```
Gln Leu Gln Leu Gln Glu Ser Gly Pro Gly Leu Val Lys Thr Ser Glu
 1               5                  10                  15

Thr Leu Ser Leu Thr Cys Thr Val Ser Gly Gly Ser Ile Arg Gly Gly
             20                  25                  30

Thr Asn Tyr Trp Ala Trp Ile Arg Gln Pro Pro Gly Lys Gly Pro Glu
         35                  40                  45

Trp Leu Gly Ser Val Tyr Tyr Ser Gly Ser Thr Tyr Asp Asn Pro Ser
 50                  55                  60

Leu Lys Ser Arg Val Ser Ile Tyr Val Asp Thr Ser Lys Asn Lys Phe
 65                  70                  75                  80

Ser Leu Arg Leu Arg Ser Val Thr Ala Ala Asp Thr Ala Ile Tyr Tyr
                 85                  90                  95

Cys Ala Arg His Glu Ser Asp Ser Ser Ser Trp His Thr Gly Trp Asn
            100                 105                 110

Trp Phe Asp Pro Trp Gly Gln Gly Thr Leu Val Thr Val Ser Ser Ala
            115                 120                 125

Ser
```

<210> SEQ ID NO 17
<211> LENGTH: 7
<212> TYPE: PRT
<213> ORGANISM: Homo sapiens

<400> SEQUENCE: 17

```
Gln Ile Val Ser Ser Ser Gln
 1               5
```

<210> SEQ ID NO 18
<211> LENGTH: 3
<212> TYPE: PRT
<213> ORGANISM: Homo sapiens

<400> SEQUENCE: 18

```
Ala Ala Ser
 1
```

<210> SEQ ID NO 19
<211> LENGTH: 8
<212> TYPE: PRT
<213> ORGANISM: Homo sapiens

<400> SEQUENCE: 19

```
Gln Gln Tyr Gly Thr Ser His Ala
 1               5
```

<210> SEQ ID NO 20
<211> LENGTH: 8
<212> TYPE: PRT
<213> ORGANISM: Homo sapiens

<400> SEQUENCE: 20

Gly Gly Thr Phe Ser Ser Phe Ala
1               5

<210> SEQ ID NO 21
<211> LENGTH: 8
<212> TYPE: PRT
<213> ORGANISM: Homo sapiens

<400> SEQUENCE: 21

Ile Ile Gly Met Phe Gly Thr Thr
1               5

<210> SEQ ID NO 22
<211> LENGTH: 13
<212> TYPE: PRT
<213> ORGANISM: Homo sapiens

<400> SEQUENCE: 22

Ala Arg Gly Lys Lys Tyr Tyr His Asp Thr Leu Asp Tyr
1               5                   10

<210> SEQ ID NO 23
<211> LENGTH: 97
<212> TYPE: PRT
<213> ORGANISM: Homo sapiens

<400> SEQUENCE: 23

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ile Val Ser Ser Ser
            20                  25                  30

Gln Leu Ala Trp Tyr Gln His Lys Pro Gly Gln Ala Pro Arg Leu Leu
        35                  40                  45

Ile Tyr Ala Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Thr Ser His
                85                  90                  95

Ala

<210> SEQ ID NO 24
<211> LENGTH: 111
<212> TYPE: PRT
<213> ORGANISM: Homo sapiens

<400> SEQUENCE: 24

Gln Ser Gln Val Gln Leu Glu Gln Ser Gly Ala Glu Val Lys Arg Pro
1               5                   10                  15

Gly Ser Ser Val Lys Val Ser Cys Gln Thr Ser Gly Gly Thr Phe Ser
            20                  25                  30

Ser Phe Ala Phe Ser Trp Val Arg Gln Ala Pro Gly Gln Gly Leu Glu
        35                  40                  45

Trp Val Gly Gly Ile Ile Gly Met Phe Gly Thr Thr Ser Tyr Ala Gln

```
                   50                    55                    60
Lys Phe Gln Gly Arg Val Thr Ile Ser Ala Asp Glu Ser Thr Ser Thr
 65                  70                  75                  80

Ala Tyr Met Glu Leu Ser Ser Leu Arg Ser Asp Asp Thr Ala Ile Tyr
                 85                  90                  95

Tyr Cys Ala Arg Gly Lys Lys Tyr Tyr His Asp Thr Leu Asp Tyr
                100                 105                 110
```

```
<210> SEQ ID NO 25
<211> LENGTH: 9
<212> TYPE: PRT
<213> ORGANISM: Homo sapiens

<400> SEQUENCE: 25

Asn Ser Asp Val Gly Thr Tyr Asn Tyr
 1               5

<210> SEQ ID NO 26
<211> LENGTH: 3
<212> TYPE: PRT
<213> ORGANISM: Homo sapiens

<400> SEQUENCE: 26

Asp Val Ser
 1

<210> SEQ ID NO 27
<211> LENGTH: 10
<212> TYPE: PRT
<213> ORGANISM: Homo sapiens

<400> SEQUENCE: 27

Ser Ser Tyr Thr Thr Ser Asn Thr Arg Val
 1               5                  10

<210> SEQ ID NO 28
<211> LENGTH: 8
<212> TYPE: PRT
<213> ORGANISM: Homo sapiens

<400> SEQUENCE: 28

Gly Gly Ile Phe Ser Asn Phe Ala
 1               5

<210> SEQ ID NO 29
<211> LENGTH: 8
<212> TYPE: PRT
<213> ORGANISM: Homo sapiens

<400> SEQUENCE: 29

Ile Leu Ser Ile Phe Arg Thr Thr
 1               5

<210> SEQ ID NO 30
<211> LENGTH: 14
<212> TYPE: PRT
<213> ORGANISM: Homo sapiens

<400> SEQUENCE: 30

Ala Arg Ser Ile Thr Asn Leu Tyr Tyr Tyr Tyr Met Asp Val
 1               5                  10

<210> SEQ ID NO 31
```

```
<211> LENGTH: 100
<212> TYPE: PRT
<213> ORGANISM: Homo sapiens

<400> SEQUENCE: 31

Gln Ser Ala Leu Thr Gln Pro Ala Ser Val Ser Gly Ser Pro Gly Gln
1               5                   10                  15

Ser Ile Thr Val Ser Cys Thr Gly Thr Asn Ser Asp Val Gly Thr Tyr
            20                  25                  30

Asn Tyr Val Ser Trp Phe Gln His Pro Gly Glu Ala Pro Lys Val
        35                  40                  45

Ile Ile Phe Asp Val Ser His Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Thr Glu Asp Glu Ala Asp Tyr Tyr Cys Ser Ser Tyr Thr Thr Ser
                85                  90                  95

Asn Thr Arg Val
            100

<210> SEQ ID NO 32
<211> LENGTH: 110
<212> TYPE: PRT
<213> ORGANISM: Homo sapiens

<400> SEQUENCE: 32

Gln Ala Gln Leu Glu Gln Ser Gly Ala Glu Val Arg Arg Pro Gly Ser
1               5                   10                  15

Ser Val Lys Val Ala Cys Lys Thr Ser Gly Gly Ile Phe Ser Asn Phe
            20                  25                  30

Ala Val Ser Trp Val Arg Gln Ala Pro Gly Gln Gly Leu Glu Trp Met
        35                  40                  45

Gly Gly Ile Leu Ser Ile Phe Arg Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Asn Ser Leu Arg Ser Asp Asp Thr Ala Val Tyr Tyr Cys
                85                  90                  95

Ala Arg Ser Ile Thr Asn Leu Tyr Tyr Tyr Met Asp Val
            100                 105                 110

<210> SEQ ID NO 33
<211> LENGTH: 6
<212> TYPE: PRT
<213> ORGANISM: Homo sapiens

<400> SEQUENCE: 33

Gln Asp Ile Ser Asn Tyr
1               5

<210> SEQ ID NO 34
<211> LENGTH: 3
<212> TYPE: PRT
<213> ORGANISM: Homo sapiens

<400> SEQUENCE: 34

Ala Thr Ser
1
```

```
<210> SEQ ID NO 35
<211> LENGTH: 9
<212> TYPE: PRT
<213> ORGANISM: Homo sapiens

<400> SEQUENCE: 35

Gln Gln Tyr Ser Arg Tyr Pro Pro Thr
1               5

<210> SEQ ID NO 36
<211> LENGTH: 8
<212> TYPE: PRT
<213> ORGANISM: Homo sapiens

<400> SEQUENCE: 36

Gly Val Ile Phe Asn Ala Tyr Ala
1               5

<210> SEQ ID NO 37
<211> LENGTH: 8
<212> TYPE: PRT
<213> ORGANISM: Homo sapiens

<400> SEQUENCE: 37

Ile Thr Gly Val Phe His Thr Ala
1               5

<210> SEQ ID NO 38
<211> LENGTH: 13
<212> TYPE: PRT
<213> ORGANISM: Homo sapiens

<400> SEQUENCE: 38

Ala Arg Gly Pro Lys Tyr Tyr His Ser Tyr Met Asp Val
1               5                   10

<210> SEQ ID NO 39
<211> LENGTH: 97
<212> TYPE: PRT
<213> ORGANISM: Homo sapiens

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
                20                  25                  30

Val Ala Trp Phe Gln Gln Lys Pro Gly Lys Thr Pro Lys Ser Leu Met
            35                  40                  45

Tyr Ala Thr Ser Lys Leu Gln Asn Gly Val Pro Ser Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Thr Tyr Tyr Cys Gln Gln Tyr Ser Arg Tyr Pro Pro
                85                  90                  95

Thr

<210> SEQ ID NO 40
<211> LENGTH: 109
<212> TYPE: PRT
<213> ORGANISM: Homo sapiens

<400> SEQUENCE: 40
```

-continued

Gln Val Gln Leu Val Gln Ser Gly Ala Glu Val Lys Lys Pro Gly Ser
1               5                   10                  15

Ser Val Lys Val Ser Cys Lys Ala Pro Gly Val Ile Phe Asn Ala Tyr
            20                  25                  30

Ala Met Ser Trp Val Arg Gln Ala Pro Gly Gln Gly Leu Glu Trp Met
        35                  40                  45

Gly Gly Ile Thr Gly Val Phe His Thr Ala Tyr Ala Pro Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Gly Pro Lys Tyr Tyr His Ser Tyr Met Asp Val
                100                 105

<210> SEQ ID NO 41
<211> LENGTH: 6
<212> TYPE: PRT
<213> ORGANISM: Homo sapiens

<400> SEQUENCE: 41

Gln Ser Val Gly Thr Asn
1               5

<210> SEQ ID NO 42
<211> LENGTH: 3
<212> TYPE: PRT
<213> ORGANISM: Homo sapiens

<400> SEQUENCE: 42

Gly Ala Ser
1

<210> SEQ ID NO 43
<211> LENGTH: 10
<212> TYPE: PRT
<213> ORGANISM: Homo sapiens

<400> SEQUENCE: 43

Gln His Tyr Asn Asn Trp Pro Pro Tyr Thr
1               5                   10

<210> SEQ ID NO 44
<211> LENGTH: 8
<212> TYPE: PRT
<213> ORGANISM: Homo sapiens

<400> SEQUENCE: 44

Gly Val Thr Phe Asn His Tyr Thr
1               5

<210> SEQ ID NO 45
<211> LENGTH: 8
<212> TYPE: PRT
<213> ORGANISM: Homo sapiens

<400> SEQUENCE: 45

Ile Ile Pro Leu Phe Gly Thr Ala
1               5

<210> SEQ ID NO 46
<211> LENGTH: 15

<212> TYPE: PRT
<213> ORGANISM: Homo sapiens

<400> SEQUENCE: 46

Ala Arg Ser Gly Thr Thr Lys Thr Arg Tyr Asn Trp Phe Asp Pro
1               5                   10                  15

<210> SEQ ID NO 47
<211> LENGTH: 98
<212> TYPE: PRT
<213> ORGANISM: Homo sapiens

<400> SEQUENCE: 47

Glu Ile Ile Met Thr Gln Ser Pro Ala Thr Leu Ser Leu Ser Pro Gly
1               5                   10                  15

Glu Arg Val Thr Leu Ser Cys Arg Ala Ser Gln Ser Val Gly Thr Asn
            20                  25                  30

Leu Ala Trp Tyr Gln Gln Lys Pro Gly Gln Ala Pro Arg Leu Leu Ile
        35                  40                  45

Phe Gly Ala Ser Thr Arg Ala Thr Gly Ile Pro Ala Arg Phe Ser Gly
    50                  55                  60

Ser Gly Ser Glu Thr Glu Phe Thr Leu Ser Ile Ser Ser Leu Gln Ser
65                  70                  75                  80

Glu Asp Phe Ala Val Tyr Tyr Cys Gln His Tyr Asn Asn Trp Pro Pro
                85                  90                  95

Tyr Thr

<210> SEQ ID NO 48
<211> LENGTH: 111
<212> TYPE: PRT
<213> ORGANISM: Homo sapiens

<400> SEQUENCE: 48

Gln Val Gln Leu Val Gln Ser Gly Ala Glu Val Lys Lys Pro Gly Ser
1               5                   10                  15

Thr Val Lys Val Ser Cys Glu Ala Ser Gly Val Thr Phe Asn His Tyr
            20                  25                  30

Thr Val Ser Trp Val Arg Gln Ala Pro Gly Gln Gly Leu Glu Trp Met
        35                  40                  45

Gly Gly Ile Ile Pro Leu Phe Gly Thr Ala Asp Tyr Ala Gln Lys Phe
    50                  55                  60

Gln Asp Arg Val Thr Ile Thr Ala Asp Arg Ser Thr Gly Thr Ala Tyr
65                  70                  75                  80

Met Glu Leu Ser Ser Leu Arg Pro Glu Asp Thr Ala Leu Tyr Tyr Cys
                85                  90                  95

Ala Arg Ser Gly Thr Thr Lys Thr Arg Tyr Asn Trp Phe Asp Pro
            100                 105                 110

<210> SEQ ID NO 49
<211> LENGTH: 7
<212> TYPE: PRT
<213> ORGANISM: Homo sapiens

<400> SEQUENCE: 49

Gln Ser Leu Ser Ser Gly His
1               5

<210> SEQ ID NO 50
<211> LENGTH: 3

-continued

```
<212> TYPE: PRT
<213> ORGANISM: Homo sapiens

<400> SEQUENCE: 50

Gly Ala Ser
1

<210> SEQ ID NO 51
<211> LENGTH: 9
<212> TYPE: PRT
<213> ORGANISM: Homo sapiens

<400> SEQUENCE: 51

Gln Gln Tyr Ala Val Phe Leu Tyr Thr
1               5

<210> SEQ ID NO 52
<211> LENGTH: 8
<212> TYPE: PRT
<213> ORGANISM: Homo sapiens

<400> SEQUENCE: 52

Gly Gly Thr Phe Ser Arg Tyr Thr
1               5

<210> SEQ ID NO 53
<211> LENGTH: 8
<212> TYPE: PRT
<213> ORGANISM: Homo sapiens

<400> SEQUENCE: 53

Phe Ile Pro Leu Leu Gly Met Thr
1               5

<210> SEQ ID NO 54
<211> LENGTH: 13
<212> TYPE: PRT
<213> ORGANISM: Homo sapiens

<400> SEQUENCE: 54

Ala Arg His Asp Ser Ser Gly Tyr His Pro Leu Asp Tyr
1               5                   10

<210> SEQ ID NO 55
<211> LENGTH: 98
<212> TYPE: PRT
<213> ORGANISM: Homo sapiens

<400> SEQUENCE: 55

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Ser Ser Gly
                20                  25                  30

His Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ala Val Phe Leu
                85                  90                  95

Tyr Thr
```

<210> SEQ ID NO 56
<211> LENGTH: 109
<212> TYPE: PRT
<213> ORGANISM: Homo sapiens

<400> SEQUENCE: 56

Gln Phe Gln Leu Val Gln Ser Gly Ala Glu Val Arg Lys Pro Gly Ser
1               5                   10                  15
Ser Val Lys Val Ser Cys Thr Ala Ser Gly Gly Thr Phe Ser Arg Tyr
            20                  25                  30
Thr Val Asn Trp Val Arg Gln Ala Pro Gly Gln Gly Leu Gln Trp Met
        35                  40                  45
Gly Arg Phe Ile Pro Leu Leu Gly Met Thr Asn Tyr Ala Gln Arg Phe
    50                  55                  60
Gln Gly Arg Ala Thr Ile Thr Ala Asp Lys Ser Thr Thr Thr Ala Phe
65                  70                  75                  80
Leu Glu Leu Ser Ser Leu Thr Ser Glu Asp Thr Ala Val Tyr Phe Cys
                85                  90                  95
Ala Arg His Asp Ser Ser Gly Tyr His Pro Leu Asp Tyr
            100                 105

<210> SEQ ID NO 57
<211> LENGTH: 6
<212> TYPE: PRT
<213> ORGANISM: Homo sapiens

<400> SEQUENCE: 57

Gln Thr Ile Ser Thr Tyr
1               5

<210> SEQ ID NO 58
<211> LENGTH: 3
<212> TYPE: PRT
<213> ORGANISM: Homo sapiens

<400> SEQUENCE: 58

Met Ala Ser
1

<210> SEQ ID NO 59
<211> LENGTH: 9
<212> TYPE: PRT
<213> ORGANISM: Homo sapiens

<400> SEQUENCE: 59

Gln His Tyr Asn Thr Tyr Ser Ser Thr
1               5

<210> SEQ ID NO 60
<211> LENGTH: 8
<212> TYPE: PRT
<213> ORGANISM: Homo sapiens

<400> SEQUENCE: 60

Gly Gly Thr Phe Ser Thr Tyr Gly
1               5

<210> SEQ ID NO 61
<211> LENGTH: 8
<212> TYPE: PRT
<213> ORGANISM: Homo sapiens

```
<400> SEQUENCE: 61

Ile Ile Pro Ile Phe Gly Thr Ala
1               5

<210> SEQ ID NO 62
<211> LENGTH: 13
<212> TYPE: PRT
<213> ORGANISM: Homo sapiens

<400> SEQUENCE: 62

Ala Arg Pro Asn Thr Tyr Gly Tyr Ile Leu Pro Val Tyr
1               5                   10

<210> SEQ ID NO 63
<211> LENGTH: 97
<212> TYPE: PRT
<213> ORGANISM: Homo sapiens

<400> SEQUENCE: 63

Asp Ile Gln Met Thr Gln Ser Pro Ser Thr Leu Ser Ala Ser Val Gly
1               5                   10                  15

Asp Arg Val Thr Ile Gly Cys Arg Ala Ser Gln Thr Ile Ser Thr Tyr
            20                  25                  30

Leu Ala Trp Tyr Gln Gln Val Pro Gly Lys Ala Pro Lys Leu Leu Ile
        35                  40                  45

Tyr Met Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Gly Asp Phe Ala Thr Tyr Tyr Cys Gln His Tyr Asn Thr Tyr Ser Ser
                85                  90                  95

Thr

<210> SEQ ID NO 64
<211> LENGTH: 109
<212> TYPE: PRT
<213> ORGANISM: Homo sapiens

<400> SEQUENCE: 64

Gln Val Gln Leu Val Gln Ser Gly Ala Glu Val Lys Lys Pro Gly Ser
1               5                   10                  15

Ser Val Met Val Ser Cys Lys Ala Ser Gly Gly Thr Phe Ser Thr Tyr
            20                  25                  30

Gly Val Ser Trp Val Arg Gln Ala Pro Gly Gln Gly Leu Glu Trp Val
        35                  40                  45

Gly Gly Ile Ile Pro Ile Phe Gly Thr Ala Lys Tyr Ala Gln Lys Phe
    50                  55                  60

Gln Gly Arg Val Thr Ile Thr Ala Asp Glu Ser Ser Thr Thr Ala Tyr
65                  70                  75                  80

Met Glu Leu Ser Arg Leu Arg Ser Glu Asp Thr Ala Val Tyr Tyr Cys
                85                  90                  95

Ala Arg Pro Asn Thr Tyr Gly Tyr Ile Leu Pro Val Tyr
            100                 105

<210> SEQ ID NO 65
<211> LENGTH: 8
<212> TYPE: PRT
<213> ORGANISM: Homo sapiens
```

<400> SEQUENCE: 65

Ser Ser Asn Ile Gly Thr Tyr Tyr
1               5

<210> SEQ ID NO 66
<211> LENGTH: 3
<212> TYPE: PRT
<213> ORGANISM: Homo sapiens

<400> SEQUENCE: 66

Asp Asn Asn
1

<210> SEQ ID NO 67
<211> LENGTH: 11
<212> TYPE: PRT
<213> ORGANISM: Homo sapiens

<400> SEQUENCE: 67

Ala Ala Trp Asp Asp Ser Leu Ser Gly Val Val
1               5                   10

<210> SEQ ID NO 68
<211> LENGTH: 10
<212> TYPE: PRT
<213> ORGANISM: Homo sapiens

<400> SEQUENCE: 68

Gly Gly Ser Ile Thr Arg Asn Ser Tyr Phe
1               5                   10

<210> SEQ ID NO 69
<211> LENGTH: 7
<212> TYPE: PRT
<213> ORGANISM: Homo sapiens

<400> SEQUENCE: 69

Met Tyr Tyr Asp Gly Thr Thr
1               5

<210> SEQ ID NO 70
<211> LENGTH: 19
<212> TYPE: PRT
<213> ORGANISM: Homo sapiens

<400> SEQUENCE: 70

Ala Arg His His Val Thr Glu Leu Arg Val Leu Glu Trp Leu Pro Lys
1               5                   10                  15

Ser Asp Tyr

<210> SEQ ID NO 71
<211> LENGTH: 100
<212> TYPE: PRT
<213> ORGANISM: Homo sapiens

<400> SEQUENCE: 71

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Thr Tyr
            20                  25                  30

Tyr Val His Trp Tyr Gln His Leu Pro Gly Thr Ala Pro Lys Leu Leu
        35                  40                  45

Ile Tyr Asp Asn Asn Gln Arg Pro Ser Gly Val Pro Asp Arg Phe Ser
            50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr His Cys Ala Ala Trp Asp Ser Leu
                 85                  90                  95

Ser Gly Val Val
            100

<210> SEQ ID NO 72
<211> LENGTH: 116
<212> TYPE: PRT
<213> ORGANISM: Homo sapiens

<400> SEQUENCE: 72

Gln Leu Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Thr Arg Asn
            20                  25                  30

Ser Tyr Phe Trp Gly Trp Ile Arg Gln Pro Pro Gly Lys Gly Leu Glu
        35                  40                  45

Trp Ile Gly Ser Met Tyr Tyr Asp Gly Thr Thr Tyr His Asn Pro Ser
 50                  55                  60

Leu Lys Ser Arg Leu Thr Leu Ser Ala Asp Thr Ser Lys Asn Gln Phe
 65                  70                  75                  80

Ser Val Arg Leu Ser Ser Val Thr Ala Ala Asp Thr Ala Val Tyr Tyr
                 85                  90                  95

Cys Ala Arg His His Val Thr Glu Leu Arg Val Leu Glu Trp Leu Pro
            100                 105                 110

Lys Ser Asp Tyr
            115

<210> SEQ ID NO 73
<211> LENGTH: 6
<212> TYPE: PRT
<213> ORGANISM: Homo sapiens

<400> SEQUENCE: 73

Gln Ser Ile Ser Ser Trp
 1               5

<210> SEQ ID NO 74
<211> LENGTH: 3
<212> TYPE: PRT
<213> ORGANISM: Homo sapiens

<400> SEQUENCE: 74

Lys Ala Ser
 1

<210> SEQ ID NO 75
<211> LENGTH: 9
<212> TYPE: PRT
<213> ORGANISM: Homo sapiens

<400> SEQUENCE: 75

Gln His Tyr Asn Ser Tyr Ser Gln Thr
 1               5

-continued

```
<210> SEQ ID NO 76
<211> LENGTH: 8
<212> TYPE: PRT
<213> ORGANISM: Homo sapiens

<400> SEQUENCE: 76

Gly Gly Thr Phe Asn Asn Tyr Ala
1               5

<210> SEQ ID NO 77
<211> LENGTH: 8
<212> TYPE: PRT
<213> ORGANISM: Homo sapiens

<400> SEQUENCE: 77

Ile Ile Pro Ile Phe Gly Thr Ala
1               5

<210> SEQ ID NO 78
<211> LENGTH: 18
<212> TYPE: PRT
<213> ORGANISM: Homo sapiens

<400> SEQUENCE: 78

Ala Arg Val Cys Ser Phe Tyr Gly Ser Gly Ser Tyr Tyr Asn Val Phe
1               5                   10                  15

Cys Tyr

<210> SEQ ID NO 79
<211> LENGTH: 112
<212> TYPE: PRT
<213> ORGANISM: Homo sapiens

<400> SEQUENCE: 79

Asp Ile Gln Met Thr Gln Ser Pro Ser Thr Leu Ser Ala Ser Ala Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln His Tyr Asn Ser Tyr Ser Gln
                85                  90                  95

Thr Phe Gly Gln Gly Thr Lys Val Glu Ile Lys Arg Thr Ala Ala Ala
            100                 105                 110

<210> SEQ ID NO 80
<211> LENGTH: 114
<212> TYPE: PRT
<213> ORGANISM: Homo sapiens

<400> SEQUENCE: 80

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Asn Tyr
                20                  25                  30

Ala Val Ser Trp Val Arg Gln Ala Pro Gly Gln Gly Leu Glu Trp Met
            35                  40                  45
```

```
Gly Gly Ile Ile Pro Ile Phe Gly Thr Ala Asn Tyr Ala His Lys Phe
        50                  55                  60
Gln Gly Arg Val Thr Ile Thr Val Asp Glu Ser Thr Ser Thr Ala Tyr
 65                  70                  75                  80
Met Glu Leu Ser Ser Leu Arg Ser Glu Asp Thr Ala Met Tyr Tyr Cys
                 85                  90                  95
Ala Arg Val Cys Ser Phe Tyr Gly Ser Gly Ser Tyr Tyr Asn Val Phe
            100                 105                 110
Cys Tyr
```

<210> SEQ ID NO 81
<211> LENGTH: 12
<212> TYPE: PRT
<213> ORGANISM: Homo sapiens

<400> SEQUENCE: 81

```
Gly Gly Ser Ile Ser Gly Gly Ser His Tyr Trp Ala
 1               5                  10
```

<210> SEQ ID NO 82
<211> LENGTH: 12
<212> TYPE: PRT
<213> ORGANISM: Homo sapiens

<400> SEQUENCE: 82

```
Gly Gly Ser Ile Arg Gly Gly Thr Asn Tyr Trp Ala
 1               5                  10
```

<210> SEQ ID NO 83
<211> LENGTH: 9
<212> TYPE: PRT
<213> ORGANISM: Homo sapiens

<400> SEQUENCE: 83

```
Val Tyr Tyr Ser Gly Ser Thr Tyr Asp
 1               5
```

<210> SEQ ID NO 84
<211> LENGTH: 9
<212> TYPE: PRT
<213> ORGANISM: Homo sapiens

<400> SEQUENCE: 84

```
Gly Gly Thr Phe Ser Ser Phe Ala Phe
 1               5
```

<210> SEQ ID NO 85
<211> LENGTH: 9
<212> TYPE: PRT
<213> ORGANISM: Homo sapiens

<400> SEQUENCE: 85

```
Ile Ile Gly Met Phe Gly Thr Thr Ser
 1               5
```

<210> SEQ ID NO 86
<211> LENGTH: 9
<212> TYPE: PRT
<213> ORGANISM: Homo sapiens

<400> SEQUENCE: 86

```
Gly Gly Ile Phe Ser Asn Phe Ala Val
```

```
1               5

<210> SEQ ID NO 87
<211> LENGTH: 4
<212> TYPE: PRT
<213> ORGANISM: Homo sapiens

<400> SEQUENCE: 87

Asp Val Ser His
1

<210> SEQ ID NO 88
<211> LENGTH: 10
<212> TYPE: PRT
<213> ORGANISM: Homo sapiens

<400> SEQUENCE: 88

Pro Gly Val Ile Phe Asn Ala Tyr Ala Met
1               5                   10

<210> SEQ ID NO 89
<211> LENGTH: 9
<212> TYPE: PRT
<213> ORGANISM: Homo sapiens

<400> SEQUENCE: 89

Ile Thr Gly Val Phe His Thr Ala Thr
1               5

<210> SEQ ID NO 90
<211> LENGTH: 7
<212> TYPE: PRT
<213> ORGANISM: Homo sapiens

<400> SEQUENCE: 90

Gln Asp Ile Ser Asn Tyr Val
1               5

<210> SEQ ID NO 91
<211> LENGTH: 6
<212> TYPE: PRT
<213> ORGANISM: Homo sapiens

<400> SEQUENCE: 91

Met Tyr Ala Thr Ser Lys
1               5

<210> SEQ ID NO 92
<211> LENGTH: 12
<212> TYPE: PRT
<213> ORGANISM: Homo sapiens

<400> SEQUENCE: 92

Glu Ala Ser Gly Val Thr Phe Asn His Tyr Thr Val
1               5                   10

<210> SEQ ID NO 93
<211> LENGTH: 9
<212> TYPE: PRT
<213> ORGANISM: Homo sapiens

<400> SEQUENCE: 93

Ile Ile Pro Leu Phe Gly Thr Ala Asp
1               5
```

<210> SEQ ID NO 94
<211> LENGTH: 4
<212> TYPE: PRT
<213> ORGANISM: Homo sapiens

<400> SEQUENCE: 94

Phe Gly Ala Ser
1

<210> SEQ ID NO 95
<211> LENGTH: 13
<212> TYPE: PRT
<213> ORGANISM: Homo sapiens

<400> SEQUENCE: 95

Thr Ala Ser Gly Gly Thr Phe Ser Arg Tyr Thr Val Asn
1               5                   10

<210> SEQ ID NO 96
<211> LENGTH: 9
<212> TYPE: PRT
<213> ORGANISM: Homo sapiens

<400> SEQUENCE: 96

Gly Gly Thr Phe Ser Thr Tyr Gly Val
1               5

<210> SEQ ID NO 97
<211> LENGTH: 9
<212> TYPE: PRT
<213> ORGANISM: Homo sapiens

<400> SEQUENCE: 97

Ile Ile Pro Ile Phe Gly Thr Ala Lys
1               5

<210> SEQ ID NO 98
<211> LENGTH: 4
<212> TYPE: PRT
<213> ORGANISM: Homo sapiens

<400> SEQUENCE: 98

Met Ala Ser Thr
1

<210> SEQ ID NO 99
<211> LENGTH: 9
<212> TYPE: PRT
<213> ORGANISM: Homo sapiens

<400> SEQUENCE: 99

Met Tyr Tyr Asp Gly Thr Thr Tyr His
1               5

<210> SEQ ID NO 100
<211> LENGTH: 10
<212> TYPE: PRT
<213> ORGANISM: Homo sapiens

<400> SEQUENCE: 100

Ser Ser Asn Ile Gly Thr Tyr Tyr Val His
1               5                   10

<210> SEQ ID NO 101

```
<211> LENGTH: 9
<212> TYPE: PRT
<213> ORGANISM: Homo sapiens

<400> SEQUENCE: 101

Gly Gly Thr Phe Asn Asn Tyr Ala Val
1               5

<210> SEQ ID NO 102
<211> LENGTH: 10
<212> TYPE: PRT
<213> ORGANISM: Homo sapiens

<400> SEQUENCE: 102

Ile Tyr Tyr Ser Gly Ser Thr Tyr Asp Ser
1               5                   10
```